United States Patent
Monson et al.

(10) Patent No.: US 9,421,060 B2
(45) Date of Patent: Aug. 23, 2016

(54) LITZ WIRE BATTERY POWERED DEVICE

(71) Applicant: Ethicon Endo-Surgery, Inc., Cincinnati, OH (US)

(72) Inventors: Gavin M. Monson, Oxford, OH (US); Gordon J. Leather, White Roding (GB); David J. Stocks, Royston (GB); John Hefin Bowen Evans, Boncath (GB); David I. Ruddenklau, Christchurch (NZ); Alan E. Green, Fulbourn (GB); Robin M. Lee, Linton (GB); Paul C. Roberts, Cambridge (GB)

(73) Assignee: Ethicon Endo-Surgery, LLC, Guaynabo, PR (US)

( * ) Notice: Subject to any disclaimer, the term of this patent is extended or adjusted under 35 U.S.C. 154(b) by 499 days.

(21) Appl. No.: 13/658,784

(22) Filed: Oct. 23, 2012

(65) Prior Publication Data
US 2013/0103023 A1  Apr. 25, 2013

Related U.S. Application Data

(60) Provisional application No. 61/550,768, filed on Oct. 24, 2011.

(51) Int. Cl.
*A61B 18/12* (2006.01)
*H02J 7/00* (2006.01)
(Continued)

(52) U.S. Cl.
CPC ......... *A61B 18/1206* (2013.01); *A61B 18/1233* (2013.01); *A61B 18/1445* (2013.01); *A61B 18/18* (2013.01); *F16B 2/20* (2013.01); *H02J 7/00* (2013.01); *A61B 2018/0072* (2013.01); *A61B 2018/00196* (2013.01); *A61B 2018/00595* (2013.01); *A61B 2018/00642* (2013.01);
(Continued)

(58) Field of Classification Search
CPC ........... A61B 18/1206; A61B 18/1233; A61B 18/1445; A61B 18/18; H02J 7/00
See application file for complete search history.

(56) References Cited

U.S. PATENT DOCUMENTS 2,366,274 A   1/1945   Luth et al.
2,458,152 A   1/1949   Eakins
(Continued)

FOREIGN PATENT DOCUMENTS

DE   29623113 U1   10/1997
DE   20004812 U1    9/2000
(Continued)

OTHER PUBLICATIONS

Sullivan, "Cost-Constrained Selection of Strand Diameter and Number in a Litz-Wire Transformer Winding," IEEE Transactions on Power Electronics, vol. 16, No. 2, Mar. 2001, pp. 281-288.
(Continued)

*Primary Examiner* — Daniel Fowler

(57) ABSTRACT

A medical instrument is disclosed. The medical instrument includes a housing and a handle for gripping by a user, an end effector coupled to the handle and having at least one electrical contact, a battery, and a radio frequency (RF) generation circuit coupled to and operated by the battery. The RF generation circuit is operable to generate an RF drive signal and to provide the RF drive signal to the at least one electrical contact, wherein the RF generation circuit is supported by the housing. The RF generation circuit includes a resonant circuit that includes at least one inductive element constructed of litz wire.

23 Claims, 39 Drawing Sheets

(51) Int. Cl.
*A61B 18/18* (2006.01)
*F16B 2/20* (2006.01)
*A61B 18/14* (2006.01)
*A61B 18/00* (2006.01)

(52) U.S. Cl.
CPC ............... *A61B2018/00702* (2013.01); *A61B 2018/00726* (2013.01); *A61B 2018/00732* (2013.01); *A61B 2018/00767* (2013.01); *A61B 2018/00827* (2013.01); *A61B 2018/00875* (2013.01); *A61B 2018/00892* (2013.01); *A61B 2018/00916* (2013.01); *A61B 2018/00922* (2013.01); *A61B 2018/1226* (2013.01); *A61B 2018/1286* (2013.01); *A61B 2018/1455* (2013.01); *Y10T 74/20666* (2015.01)

(56) References Cited

U.S. PATENT DOCUMENTS

| | | | |
|---|---|---|---|
| 2,510,693 A | 6/1950 | Green | |
| 3,166,971 A | 1/1965 | Stoecker | |
| 3,580,841 A | 5/1971 | Cadotte et al. | |
| 3,703,651 A | 11/1972 | Blowers | |
| 3,777,760 A | 12/1973 | Essner | |
| 4,005,714 A | 2/1977 | Hiltebrandt | |
| 4,034,762 A | 7/1977 | Cosens et al. | |
| 4,058,126 A | 11/1977 | Leveen | |
| 4,220,154 A | 9/1980 | Semm | |
| 4,237,441 A | 12/1980 | van Konynenburg et al. | |
| 4,281,785 A | 8/1981 | Brooks | |
| 4,304,987 A | 12/1981 | van Konynenburg | |
| 4,463,759 A | 8/1984 | Garito et al. | |
| 4,492,231 A | 1/1985 | Auth | |
| 4,535,773 A | 8/1985 | Yoon | |
| 4,545,926 A | 10/1985 | Fouts, Jr. et al. | |
| 4,550,870 A | 11/1985 | Krumme et al. | |
| 4,582,236 A | 4/1986 | Hirose | |
| 4,617,927 A | 10/1986 | Manes | |
| 4,735,603 A | 4/1988 | Goodson et al. | |
| 4,761,871 A | 8/1988 | O'Connor et al. | |
| 4,830,462 A | 5/1989 | Karny et al. | |
| 4,849,133 A | 7/1989 | Yoshida et al. | |
| 4,860,745 A | 8/1989 | Farin et al. | |
| 4,878,493 A * | 11/1989 | Pasternak et al. | 607/99 |
| 4,910,389 A | 3/1990 | Sherman et al. | |
| 4,920,978 A | 5/1990 | Colvin | |
| 4,936,842 A | 6/1990 | D'Amelio et al. | |
| 5,061,269 A | 10/1991 | Muller | |
| 5,099,840 A * | 3/1992 | Goble et al. | 607/71 |
| 5,104,025 A | 4/1992 | Main et al. | |
| 5,106,538 A | 4/1992 | Barma et al. | |
| 5,108,383 A | 4/1992 | White | |
| 5,160,334 A | 11/1992 | Billings et al. | |
| 5,190,541 A | 3/1993 | Abele et al. | |
| 5,196,007 A | 3/1993 | Ellman et al. | |
| 5,205,459 A | 4/1993 | Brinkerhoff et al. | |
| 5,217,460 A | 6/1993 | Knoepfler | |
| 5,234,428 A | 8/1993 | Kaufman | |
| 5,258,006 A | 11/1993 | Rydell et al. | |
| 5,285,945 A | 2/1994 | Brinkerhoff et al. | |
| 5,290,286 A | 3/1994 | Parins | |
| 5,309,927 A | 5/1994 | Welch | |
| 5,318,564 A | 6/1994 | Eggers | |
| 5,318,589 A | 6/1994 | Lichtman | |
| 5,330,471 A | 7/1994 | Eggers | |
| 5,339,723 A | 8/1994 | Huitema | |
| 5,342,359 A | 8/1994 | Rydell | |
| 5,361,583 A | 11/1994 | Huitema | |
| 5,383,874 A | 1/1995 | Jackson et al. | |
| 5,387,207 A | 2/1995 | Dyer et al. | |
| 5,389,098 A | 2/1995 | Tsuruta et al. | |
| 5,395,312 A | 3/1995 | Desai | |
| 5,395,363 A | 3/1995 | Billings et al. | |
| 5,395,364 A | 3/1995 | Anderhub et al. | |
| 5,396,900 A | 3/1995 | Slater et al. | |
| 5,403,312 A | 4/1995 | Yates et al. | |
| 5,417,709 A | 5/1995 | Slater | |
| 5,428,504 A | 6/1995 | Bhatla | |
| 5,429,131 A | 7/1995 | Scheinman et al. | |
| 5,443,463 A | 8/1995 | Stern et al. | |
| 5,445,638 A | 8/1995 | Rydell et al. | |
| 5,451,227 A | 9/1995 | Michaelson | |
| 5,458,598 A | 10/1995 | Feinberg et al. | |
| 5,465,895 A | 11/1995 | Knodel et al. | |
| 5,472,443 A | 12/1995 | Cordis et al. | |
| 5,476,479 A | 12/1995 | Green et al. | |
| 5,480,409 A | 1/1996 | Riza | |
| 5,484,436 A | 1/1996 | Eggers et al. | |
| 5,486,189 A | 1/1996 | Mudry et al. | |
| 5,496,317 A | 3/1996 | Goble et al. | |
| 5,504,650 A | 4/1996 | Katsui et al. | |
| 5,509,922 A | 4/1996 | Aranyi et al. | |
| 5,511,556 A | 4/1996 | DeSantis | |
| 5,520,704 A | 5/1996 | Castro et al. | |
| 5,522,839 A | 6/1996 | Pilling | |
| 5,531,744 A | 7/1996 | Nardella et al. | |
| 5,542,916 A | 8/1996 | Hirsch et al. | |
| 5,558,671 A | 9/1996 | Yates | |
| 5,563,179 A | 10/1996 | Stone et al. | |
| 5,571,121 A | 11/1996 | Heifetz | |
| 5,573,534 A | 11/1996 | Stone | |
| 5,584,830 A | 12/1996 | Ladd et al. | |
| 5,599,350 A | 2/1997 | Schulze et al. | |
| 5,611,813 A | 3/1997 | Lichtman | |
| 5,618,307 A | 4/1997 | Donlon et al. | |
| 5,624,452 A | 4/1997 | Yates | |
| 5,647,871 A | 7/1997 | Levine et al. | |
| 5,658,281 A | 8/1997 | Heard | |
| 5,662,667 A | 9/1997 | Knodel | |
| 5,665,085 A | 9/1997 | Nardella | |
| 5,665,100 A | 9/1997 | Yoon | |
| 5,674,219 A | 10/1997 | Monson et al. | |
| 5,674,220 A | 10/1997 | Fox et al. | |
| 5,688,270 A | 11/1997 | Yates et al. | |
| 5,693,051 A | 12/1997 | Schulze et al. | |
| 5,709,680 A | 1/1998 | Yates et al. | |
| 5,713,896 A | 2/1998 | Nardella | |
| 5,716,366 A | 2/1998 | Yates | |
| 5,735,848 A | 4/1998 | Yates et al. | |
| 5,743,906 A | 4/1998 | Parins et al. | |
| 5,752,973 A | 5/1998 | Kieturakis | |
| 5,755,717 A | 5/1998 | Yates et al. | |
| 5,762,255 A | 6/1998 | Chrisman et al. | |
| 5,779,701 A | 7/1998 | McBrayer et al. | |
| 5,782,834 A | 7/1998 | Lucey et al. | |
| 5,792,138 A * | 8/1998 | Shipp | 606/38 |
| 5,797,941 A | 8/1998 | Schulze et al. | |
| 5,800,432 A | 9/1998 | Swanson | |
| 5,800,449 A | 9/1998 | Wales | |
| 5,807,393 A | 9/1998 | Williamson, IV et al. | |
| 5,810,811 A | 9/1998 | Yates et al. | |
| 5,817,033 A | 10/1998 | DeSantis et al. | |
| 5,817,093 A | 10/1998 | Williamson, IV et al. | |
| 5,836,909 A | 11/1998 | Cosmescu | |
| 5,836,943 A * | 11/1998 | Miller, III | 606/34 |
| 5,853,412 A | 12/1998 | Mayenberger | |
| 5,876,401 A | 3/1999 | Schulze et al. | |
| 5,880,668 A | 3/1999 | Hall | |
| 5,891,142 A | 4/1999 | Eggers et al. | |
| 5,906,625 A | 5/1999 | Bito et al. | |
| 5,984,938 A | 11/1999 | Yoon | |
| 6,003,517 A | 12/1999 | Sheffield et al. | |
| 6,013,052 A | 1/2000 | Durman et al. | |
| 6,024,741 A | 2/2000 | Williamson, IV et al. | |
| 6,024,744 A | 2/2000 | Kese et al. | |
| 6,033,399 A | 3/2000 | Gines | |
| 6,039,734 A * | 3/2000 | Goble | 606/41 |
| 6,050,996 A | 4/2000 | Schmaltz et al. | |
| 6,063,098 A | 5/2000 | Houser et al. | |
| 6,068,629 A | 5/2000 | Haissaguerre et al. | |
| 6,074,389 A | 6/2000 | Levine et al. | |
| 6,091,995 A | 7/2000 | Ingle et al. | |
| 6,099,483 A | 8/2000 | Palmer et al. | |

(56) References Cited

U.S. PATENT DOCUMENTS

| | | |
|---|---|---|
| 6,099,550 A | 8/2000 | Yoon |
| H1904 H | 10/2000 | Yates et al. |
| 6,144,402 A | 11/2000 | Norsworthy et al. |
| 6,152,923 A | 11/2000 | Ryan |
| 6,174,309 B1 | 1/2001 | Wrublewski et al. |
| 6,206,876 B1 | 3/2001 | Levine et al. |
| 6,228,080 B1 | 5/2001 | Gines |
| 6,259,230 B1 | 7/2001 | Chou |
| 6,277,117 B1 | 8/2001 | Tetzlaff et al. |
| 6,292,700 B1 | 9/2001 | Morrison et al. |
| 6,325,799 B1 | 12/2001 | Goble |
| 6,340,878 B1 | 1/2002 | Oglesbee |
| 6,391,026 B1 | 5/2002 | Hung et al. |
| 6,398,779 B1 | 6/2002 | Buysse et al. |
| H2037 H | 7/2002 | Yates et al. |
| 6,419,675 B1 | 7/2002 | Gallo, Sr. |
| 6,430,446 B1 * | 8/2002 | Knowlton ............... 607/101 |
| 6,443,968 B1 | 9/2002 | Holthaus et al. |
| 6,458,128 B1 | 10/2002 | Schulze |
| 6,464,702 B2 | 10/2002 | Schulze et al. |
| 6,491,690 B1 | 12/2002 | Goble et al. |
| 6,500,112 B1 | 12/2002 | Khouri |
| 6,500,176 B1 | 12/2002 | Truckai et al. |
| 6,503,248 B1 | 1/2003 | Levine |
| 6,511,480 B1 | 1/2003 | Tetzlaff et al. |
| 6,514,252 B2 | 2/2003 | Nezhat et al. |
| 6,517,565 B1 | 2/2003 | Whitman et al. |
| 6,531,846 B1 | 3/2003 | Smith |
| 6,533,784 B2 | 3/2003 | Truckai et al. |
| 6,537,272 B2 | 3/2003 | Christopherson et al. |
| 6,554,829 B2 | 4/2003 | Schulze et al. |
| 6,558,376 B2 | 5/2003 | Bishop |
| 6,572,639 B1 | 6/2003 | Ingle et al. |
| 6,575,969 B1 | 6/2003 | Rittman, III et al. |
| 6,584,360 B2 | 6/2003 | Francischelli et al. |
| 6,585,735 B1 | 7/2003 | Frazier et al. |
| 6,589,200 B1 | 7/2003 | Schwemberger et al. |
| 6,602,252 B2 | 8/2003 | Mollenauer |
| 6,620,161 B2 | 9/2003 | Schulze et al. |
| 6,622,731 B2 | 9/2003 | Daniel et al. |
| 6,623,482 B2 | 9/2003 | Pendekanti et al. |
| 6,635,057 B2 | 10/2003 | Harano et al. |
| 6,651,669 B1 | 11/2003 | Burnside |
| 6,656,177 B2 | 12/2003 | Truckai et al. |
| 6,656,198 B2 | 12/2003 | Tsonton et al. |
| 6,673,248 B2 | 1/2004 | Chowdhury |
| 6,679,882 B1 | 1/2004 | Kornerup |
| 6,695,840 B2 | 2/2004 | Schulze |
| 6,722,552 B2 | 4/2004 | Fenton, Jr. |
| 6,770,072 B1 | 8/2004 | Truckai et al. |
| 6,773,409 B2 | 8/2004 | Truckai et al. |
| 6,773,435 B2 | 8/2004 | Schulze et al. |
| 6,775,575 B2 | 8/2004 | Bommannan et al. |
| 6,789,939 B2 | 9/2004 | Schrödinger et al. |
| 6,796,981 B2 | 9/2004 | Wham et al. |
| 6,800,085 B2 | 10/2004 | Selmon et al. |
| 6,802,843 B2 | 10/2004 | Truckai et al. |
| 6,811,842 B1 | 11/2004 | Ehrnsperger et al. |
| 6,821,273 B2 | 11/2004 | Mollenauer |
| 6,835,199 B2 | 12/2004 | McGuckin, Jr. et al. |
| 6,840,938 B1 | 1/2005 | Morley et al. |
| 6,860,880 B2 | 3/2005 | Treat et al. |
| 6,905,497 B2 | 6/2005 | Truckai et al. |
| 6,908,463 B2 | 6/2005 | Treat et al. |
| 6,913,579 B2 | 7/2005 | Truckai et al. |
| 6,926,716 B2 | 8/2005 | Baker et al. |
| 6,929,622 B2 | 8/2005 | Chian |
| 6,929,644 B2 | 8/2005 | Truckai et al. |
| 6,953,461 B2 | 10/2005 | McClurken et al. |
| 7,000,818 B2 | 2/2006 | Shelton, IV et al. |
| 7,011,657 B2 | 3/2006 | Truckai et al. |
| 7,041,102 B2 | 5/2006 | Truckai et al. |
| 7,052,496 B2 | 5/2006 | Yamauchi |
| 7,055,731 B2 | 6/2006 | Shelton, IV et al. |
| 7,063,699 B2 | 6/2006 | Hess et al. |
| 7,066,936 B2 | 6/2006 | Ryan |
| 7,070,597 B2 | 7/2006 | Truckai et al. |
| 7,083,618 B2 | 8/2006 | Couture et al. |
| 7,083,619 B2 | 8/2006 | Truckai et al. |
| 7,087,054 B2 | 8/2006 | Truckai et al. |
| 7,094,235 B2 | 8/2006 | Francischelli et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,112,201 B2 | 9/2006 | Truckai et al. |
| 7,118,570 B2 | 10/2006 | Tetzlaff et al. |
| 7,125,409 B2 | 10/2006 | Truckai et al. |
| 7,131,970 B2 | 11/2006 | Moses et al. |
| 7,137,980 B2 | 11/2006 | Buysse et al. |
| 7,143,925 B2 | 12/2006 | Shelton, IV et al. |
| 7,147,138 B2 | 12/2006 | Shelton, IV |
| 7,156,846 B2 | 1/2007 | Dycus et al. |
| 7,160,296 B2 | 1/2007 | Pearson et al. |
| 7,169,146 B2 | 1/2007 | Truckai et al. |
| 7,169,156 B2 | 1/2007 | Hart |
| 7,186,253 B2 | 3/2007 | Truckai et al. |
| 7,189,233 B2 | 3/2007 | Truckai et al. |
| 7,195,631 B2 | 3/2007 | Dumbauld |
| 7,207,471 B2 | 4/2007 | Heinrich et al. |
| 7,220,951 B2 | 5/2007 | Truckai et al. |
| 7,225,964 B2 | 6/2007 | Mastri et al. |
| 7,226,448 B2 | 6/2007 | Bertolero et al. |
| 7,232,440 B2 | 6/2007 | Dumbauld et al. |
| 7,235,073 B2 | 6/2007 | Levine et al. |
| 7,241,294 B2 | 7/2007 | Reschke |
| 7,251,531 B2 | 7/2007 | Mosher et al. |
| 7,252,667 B2 | 8/2007 | Moses et al. |
| 7,267,677 B2 | 9/2007 | Johnson et al. |
| 7,267,685 B2 | 9/2007 | Butaric et al. |
| 7,287,682 B1 | 10/2007 | Ezzat et al. |
| 7,300,450 B2 | 11/2007 | Vleugels et al. |
| 7,303,557 B2 | 12/2007 | Wham et al. |
| 7,307,313 B2 | 12/2007 | Ohyanagi et al. |
| 7,309,849 B2 | 12/2007 | Truckai et al. |
| 7,311,709 B2 | 12/2007 | Truckai et al. |
| 7,329,257 B2 | 2/2008 | Kanehira et al. |
| 7,354,440 B2 | 4/2008 | Truckal et al. |
| 7,357,287 B2 | 4/2008 | Shelton, IV et al. |
| 7,364,577 B2 | 4/2008 | Wham et al. |
| 7,367,976 B2 | 5/2008 | Lawes et al. |
| 7,371,227 B2 | 5/2008 | Zeiner |
| RE40,388 E | 6/2008 | Gines |
| 7,381,209 B2 | 6/2008 | Truckai et al. |
| 7,384,420 B2 | 6/2008 | Dycus et al. |
| 7,396,356 B2 | 7/2008 | Mollenauer |
| 7,403,224 B2 | 7/2008 | Fuller et al. |
| 7,404,508 B2 | 7/2008 | Smith et al. |
| 7,407,077 B2 | 8/2008 | Ortiz et al. |
| 7,422,139 B2 | 9/2008 | Shelton, IV et al. |
| 7,435,582 B2 | 10/2008 | Zimmermann et al. |
| 7,442,193 B2 | 10/2008 | Shields et al. |
| 7,445,621 B2 | 11/2008 | Dumbauld et al. |
| 7,464,846 B2 | 12/2008 | Shelton, IV et al. |
| 7,473,253 B2 | 1/2009 | Dycus et al. |
| 7,488,319 B2 | 2/2009 | Yates |
| 7,491,201 B2 | 2/2009 | Shields et al. |
| 7,494,501 B2 | 2/2009 | Ahlberg et al. |
| 7,510,107 B2 | 3/2009 | Timm et al. |
| 7,513,025 B2 | 4/2009 | Fischer |
| 7,517,349 B2 | 4/2009 | Truckai et al. |
| 7,540,872 B2 | 6/2009 | Schechter et al. |
| 7,550,216 B2 | 6/2009 | Ofer et al. |
| 7,559,452 B2 | 7/2009 | Wales et al. |
| 7,582,086 B2 | 9/2009 | Privitera et al. |
| 7,586,289 B2 | 9/2009 | Andruk et al. |
| 7,588,176 B2 | 9/2009 | Timm et al. |
| 7,594,925 B2 | 9/2009 | Danek et al. |
| 7,597,693 B2 | 10/2009 | Garrison |
| 7,604,150 B2 | 10/2009 | Boudreaux |
| 7,628,791 B2 | 12/2009 | Garrison et al. |
| 7,628,792 B2 | 12/2009 | Guerra |
| 7,632,267 B2 | 12/2009 | Dahla |
| 7,632,269 B2 | 12/2009 | Truckai et al. |
| 7,641,653 B2 | 1/2010 | Dalla Betta et al. |

(56) References Cited

U.S. PATENT DOCUMENTS

| | | |
|---|---|---|
| 7,641,671 B2 | 1/2010 | Crainich |
| 7,644,848 B2 | 1/2010 | Swayze et al. |
| 7,645,277 B2 | 1/2010 | McClurken et al. |
| 7,658,311 B2 | 2/2010 | Boudreaux |
| 7,665,647 B2 | 2/2010 | Shelton, IV et al. |
| 7,666,206 B2 | 2/2010 | Taniguchi et al. |
| 7,703,459 B2 | 4/2010 | Saadat et al. |
| 7,708,751 B2 | 5/2010 | Hughes et al. |
| 7,722,607 B2 | 5/2010 | Dumbauld et al. |
| 7,753,904 B2 | 7/2010 | Shelton, IV et al. |
| 7,753,908 B2 | 7/2010 | Swanson |
| 7,762,445 B2 | 7/2010 | Heinrich et al. |
| 7,766,910 B2 | 8/2010 | Hixson et al. |
| 7,776,037 B2 | 8/2010 | Odom |
| 7,780,663 B2 | 8/2010 | Yates et al. |
| 7,784,663 B2 | 8/2010 | Shelton, IV |
| 7,803,156 B2 | 9/2010 | Eder et al. |
| 7,815,641 B2 | 10/2010 | Dodde et al. |
| 7,819,298 B2 | 10/2010 | Hall et al. |
| 7,819,299 B2 | 10/2010 | Shelton, IV et al. |
| 7,819,872 B2 | 10/2010 | Johnson et al. |
| 7,832,408 B2 | 11/2010 | Shelton, IV et al. |
| 7,832,612 B2 | 11/2010 | Baxter, III et al. |
| 7,846,159 B2 | 12/2010 | Morrison et al. |
| 7,846,160 B2 | 12/2010 | Payne et al. |
| 7,879,035 B2 | 2/2011 | Garrison et al. |
| 7,879,070 B2 | 2/2011 | Ortiz et al. |
| 7,901,400 B2 | 3/2011 | Wham et al. |
| 7,931,649 B2 | 4/2011 | Couture et al. |
| 7,935,114 B2 | 5/2011 | Takashino et al. |
| 7,955,331 B2 | 6/2011 | Truckai et al. |
| 7,963,963 B2 | 6/2011 | Francischelli et al. |
| 7,967,602 B2 | 6/2011 | Lindquist |
| 7,981,113 B2 | 7/2011 | Truckai et al. |
| 8,020,743 B2 | 9/2011 | Shelton, IV |
| 8,058,771 B2 | 11/2011 | Giordano et al. |
| 8,070,036 B1 | 12/2011 | Knodel et al. |
| 8,105,323 B2 | 1/2012 | Buysse et al. |
| 8,128,624 B2 | 3/2012 | Couture et al. |
| 8,136,712 B2 | 3/2012 | Zingman |
| 8,141,762 B2 | 3/2012 | Bedi et al. |
| 8,157,145 B2 | 4/2012 | Shelton, IV et al. |
| 8,197,472 B2 | 6/2012 | Lau et al. |
| 8,197,479 B2 | 6/2012 | Olson et al. |
| 8,221,415 B2 | 7/2012 | Francischelli |
| 8,246,615 B2 | 8/2012 | Behnke |
| 8,246,618 B2 | 8/2012 | Bucciaglia et al. |
| 8,251,994 B2 | 8/2012 | McKenna et al. |
| 8,262,563 B2 | 9/2012 | Bakos et al. |
| 8,277,446 B2 | 10/2012 | Heard |
| 8,277,447 B2 | 10/2012 | Garrison et al. |
| 8,282,669 B2 | 10/2012 | Gerber et al. |
| 8,287,528 B2 | 10/2012 | Wham et al. |
| 8,292,886 B2 | 10/2012 | Kerr et al. |
| 8,298,232 B2 | 10/2012 | Unger |
| 8,323,310 B2 | 12/2012 | Kingsley |
| 8,377,059 B2 | 2/2013 | Deville et al. |
| 8,397,971 B2 | 3/2013 | Yates et al. |
| 8,414,577 B2 | 4/2013 | Boudreaux et al. |
| 8,430,876 B2 | 4/2013 | Kappus et al. |
| 8,453,906 B2 | 6/2013 | Huang et al. |
| 8,460,288 B2 | 6/2013 | Tamai et al. |
| 8,460,292 B2 | 6/2013 | Truckai et al. |
| 8,486,057 B2 | 7/2013 | Behnke, II |
| 8,496,682 B2 | 7/2013 | Guerra et al. |
| 8,535,311 B2 | 9/2013 | Schall |
| 8,562,598 B2 | 10/2013 | Falkenstein et al. |
| 8,562,604 B2 | 10/2013 | Nishimura |
| 8,568,412 B2 | 10/2013 | Brandt et al. |
| 8,569,997 B2 | 10/2013 | Lee |
| 8,574,231 B2 | 11/2013 | Boudreaux et al. |
| 8,591,506 B2 | 11/2013 | Wham et al. |
| 8,613,383 B2 | 12/2013 | Beckman et al. |
| 8,623,044 B2 | 1/2014 | Timm et al. |
| 8,628,529 B2 | 1/2014 | Aldridge et al. |
| 8,632,461 B2 | 1/2014 | Glossop |
| 8,647,350 B2 | 2/2014 | Mohan et al. |
| 8,663,222 B2 | 3/2014 | Anderson et al. |
| 8,685,020 B2 | 4/2014 | Weizman et al. |
| 8,696,665 B2 | 4/2014 | Hunt et al. |
| 8,702,609 B2 | 4/2014 | Hadjicostis |
| 8,702,704 B2 | 4/2014 | Shelton, IV et al. |
| 8,709,035 B2 | 4/2014 | Johnson et al. |
| 8,715,270 B2 | 5/2014 | Weitzner et al. |
| 8,715,277 B2 | 5/2014 | Weizman |
| 8,734,443 B2 | 5/2014 | Hixson et al. |
| 8,747,404 B2 | 6/2014 | Boudreaux et al. |
| 8,753,338 B2 | 6/2014 | Widenhouse et al. |
| 8,764,747 B2 | 7/2014 | Cummings et al. |
| 8,790,342 B2 | 7/2014 | Stulen et al. |
| 8,795,276 B2 | 8/2014 | Dietz et al. |
| 8,795,327 B2 | 8/2014 | Dietz et al. |
| 8,834,466 B2 | 9/2014 | Cummings et al. |
| 8,834,518 B2 | 9/2014 | Faller et al. |
| 8,888,776 B2 | 11/2014 | Dietz et al. |
| 8,906,016 B2 | 12/2014 | Boudreaux et al. |
| 8,926,607 B2 | 1/2015 | Norvell et al. |
| 8,926,608 B2 | 1/2015 | Bacher et al. |
| 8,939,974 B2 | 1/2015 | Boudreaux et al. |
| 8,979,843 B2 | 3/2015 | Timm et al. |
| 8,979,844 B2 | 3/2015 | White et al. |
| 9,005,199 B2 | 4/2015 | Beckman et al. |
| 9,011,437 B2 | 4/2015 | Woodruff et al. |
| 9,044,243 B2 | 6/2015 | Johnson et al. |
| 2002/0022836 A1* | 2/2002 | Goble et al. ............ 606/34 |
| 2002/0165541 A1 | 11/2002 | Whitman |
| 2003/0014053 A1 | 1/2003 | Nguyen et al. |
| 2003/0105474 A1 | 6/2003 | Bonutti |
| 2003/0114851 A1 | 6/2003 | Truckai et al. |
| 2003/0130693 A1 | 7/2003 | Levin et al. |
| 2003/0139741 A1 | 7/2003 | Goble et al. |
| 2003/0158548 A1 | 8/2003 | Phan et al. |
| 2003/0216722 A1 | 11/2003 | Swanson |
| 2003/0229344 A1 | 12/2003 | Dycus et al. |
| 2004/0019350 A1 | 1/2004 | O'Brien et al. |
| 2004/0092992 A1 | 5/2004 | Adams et al. |
| 2004/0138621 A1 | 7/2004 | Jahns et al. |
| 2004/0167508 A1 | 8/2004 | Wham et al. |
| 2004/0193150 A1 | 9/2004 | Sharkey et al. |
| 2004/0232196 A1 | 11/2004 | Shelton, IV et al. |
| 2004/0249374 A1 | 12/2004 | Tetzlaff et al. |
| 2004/0260273 A1 | 12/2004 | Wan |
| 2005/0015125 A1 | 1/2005 | Mioduski et al. |
| 2005/0033278 A1 | 2/2005 | McClurken et al. |
| 2005/0085809 A1 | 4/2005 | Mucko et al. |
| 2005/0090817 A1 | 4/2005 | Phan |
| 2005/0165429 A1 | 7/2005 | Douglas et al. |
| 2005/0171522 A1 | 8/2005 | Christopherson |
| 2005/0203507 A1 | 9/2005 | Truckai et al. |
| 2005/0261581 A1 | 11/2005 | Hughes et al. |
| 2005/0267464 A1 | 12/2005 | Truckai et al. |
| 2006/0052778 A1 | 3/2006 | Chapman et al. |
| 2006/0064086 A1 | 3/2006 | Odom |
| 2006/0069388 A1 | 3/2006 | Truckai et al. |
| 2006/0159731 A1 | 7/2006 | Shoshan |
| 2006/0270916 A1 | 11/2006 | Skwarek et al. |
| 2006/0280916 A1* | 12/2006 | Tung et al. ............ 428/403 |
| 2006/0293656 A1 | 12/2006 | Shadduck et al. |
| 2007/0027469 A1 | 2/2007 | Smith et al. |
| 2007/0073185 A1 | 3/2007 | Nakao |
| 2007/0073341 A1 | 3/2007 | Smith et al. |
| 2007/0106158 A1 | 5/2007 | Madan et al. |
| 2007/0118106 A1* | 5/2007 | Utley et al. ............ 606/41 |
| 2007/0146113 A1 | 6/2007 | Truckai et al. |
| 2007/0173803 A1 | 7/2007 | Wham et al. |
| 2007/0173813 A1 | 7/2007 | Odom |
| 2007/0185474 A1 | 8/2007 | Nahen |
| 2007/0191713 A1 | 8/2007 | Eichmann et al. |
| 2007/0191830 A1 | 8/2007 | Crompton, Jr. et al. |
| 2007/0203483 A1 | 8/2007 | Kim et al. |
| 2007/0208312 A1 | 9/2007 | Norton et al. |
| 2007/0225698 A1* | 9/2007 | Orszulak et al. ............ 606/34 |
| 2007/0232920 A1 | 10/2007 | Kowalski et al. |
| 2007/0232926 A1 | 10/2007 | Stulen et al. |

(56) References Cited

U.S. PATENT DOCUMENTS

| | | |
|---|---|---|
| 2007/0232927 A1 | 10/2007 | Madan et al. |
| 2007/0232928 A1 | 10/2007 | Wiener et al. |
| 2007/0236213 A1 | 10/2007 | Paden et al. |
| 2007/0239025 A1 | 10/2007 | Wiener et al. |
| 2007/0260242 A1 | 11/2007 | Dycus et al. |
| 2007/0265613 A1 | 11/2007 | Edelstein et al. |
| 2008/0015575 A1 | 1/2008 | Odom et al. |
| 2008/0071269 A1 | 3/2008 | Hilario et al. |
| 2008/0114355 A1 | 5/2008 | Whayne et al. |
| 2008/0147058 A1 | 6/2008 | Horrell et al. |
| 2008/0147062 A1 | 6/2008 | Truckai et al. |
| 2008/0167522 A1 | 7/2008 | Giordano et al. |
| 2008/0188755 A1 | 8/2008 | Hart |
| 2008/0188851 A1 | 8/2008 | Truckai et al. |
| 2008/0188912 A1 | 8/2008 | Stone et al. |
| 2008/0221565 A1 | 9/2008 | Eder et al. |
| 2008/0262491 A1 | 10/2008 | Swoyer et al. |
| 2008/0269862 A1 | 10/2008 | Elmouelhi et al. |
| 2008/0281315 A1 | 11/2008 | Gines |
| 2008/0294158 A1 | 11/2008 | Pappone et al. |
| 2009/0012516 A1 | 1/2009 | Curtis et al. |
| 2009/0048589 A1 | 2/2009 | Takashino et al. |
| 2009/0076506 A1 | 3/2009 | Baker |
| 2009/0076534 A1 | 3/2009 | Shelton, IV et al. |
| 2009/0099582 A1 | 4/2009 | Isaacs et al. |
| 2009/0125026 A1 | 5/2009 | Rioux et al. |
| 2009/0125027 A1 | 5/2009 | Fischer |
| 2009/0138003 A1 | 5/2009 | Deville et al. |
| 2009/0138006 A1 | 5/2009 | Bales et al. |
| 2009/0182332 A1 | 7/2009 | Long et al. |
| 2009/0206140 A1 | 8/2009 | Scheib et al. |
| 2009/0209979 A1 | 8/2009 | Yates et al. |
| 2009/0248002 A1 | 10/2009 | Takashino et al. |
| 2009/0248021 A1 | 10/2009 | McKenna |
| 2009/0318915 A1* | 12/2009 | Hosier et al. .................. 606/33 |
| 2009/0320268 A1 | 12/2009 | Cunningham et al. |
| 2009/0326530 A1 | 12/2009 | Orban, III et al. |
| 2010/0032470 A1 | 2/2010 | Hess et al. |
| 2010/0036370 A1 | 2/2010 | Mirel et al. |
| 2010/0036380 A1 | 2/2010 | Taylor et al. |
| 2010/0076433 A1 | 3/2010 | Taylor et al. |
| 2010/0081863 A1 | 4/2010 | Hess et al. |
| 2010/0081864 A1 | 4/2010 | Hess et al. |
| 2010/0081880 A1 | 4/2010 | Widenhouse et al. |
| 2010/0081881 A1 | 4/2010 | Murray et al. |
| 2010/0081882 A1 | 4/2010 | Hess et al. |
| 2010/0081883 A1 | 4/2010 | Murray et al. |
| 2010/0081995 A1 | 4/2010 | Widenhouse et al. |
| 2010/0094323 A1 | 4/2010 | Isaacs et al. |
| 2010/0168620 A1 | 7/2010 | Klimovitch et al. |
| 2010/0222752 A1 | 9/2010 | Collins, Jr. et al. |
| 2010/0237132 A1 | 9/2010 | Measamer et al. |
| 2010/0264194 A1 | 10/2010 | Huang et al. |
| 2010/0274278 A1 | 10/2010 | Fleenor et al. |
| 2011/0015627 A1 | 1/2011 | DiNardo et al. |
| 2011/0082486 A1 | 4/2011 | Messerly et al. |
| 2011/0087212 A1 | 4/2011 | Aldridge et al. |
| 2011/0087213 A1 | 4/2011 | Messerly et al. |
| 2011/0087214 A1 | 4/2011 | Giordano et al. |
| 2011/0087215 A1 | 4/2011 | Aldridge et al. |
| 2011/0087216 A1 | 4/2011 | Aldridge et al. |
| 2011/0087217 A1 | 4/2011 | Yates et al. |
| 2011/0087220 A1 | 4/2011 | Felder et al. |
| 2011/0155781 A1 | 6/2011 | Swensgard et al. |
| 2011/0224668 A1 | 9/2011 | Johnson et al. |
| 2011/0276049 A1 | 11/2011 | Gerhardt |
| 2011/0276057 A1 | 11/2011 | Conlon et al. |
| 2011/0301605 A1 | 12/2011 | Horner |
| 2011/0306967 A1 | 12/2011 | Payne et al. |
| 2012/0010616 A1 | 1/2012 | Huang et al. |
| 2012/0016413 A1 | 1/2012 | Timm et al. |
| 2012/0022519 A1 | 1/2012 | Huang et al. |
| 2012/0022526 A1 | 1/2012 | Aldridge et al. |
| 2012/0022527 A1 | 1/2012 | Woodruff et al. |
| 2012/0078248 A1 | 3/2012 | Worrell et al. |
| 2012/0083783 A1 | 4/2012 | Davison et al. |
| 2012/0109186 A1 | 5/2012 | Parrott et al. |
| 2012/0116379 A1 | 5/2012 | Yates et al. |
| 2012/0116391 A1 | 5/2012 | Houser et al. |
| 2012/0130256 A1 | 5/2012 | Buysse et al. |
| 2012/0136353 A1 | 5/2012 | Romero |
| 2012/0150170 A1 | 6/2012 | Buysse et al. |
| 2012/0172859 A1 | 7/2012 | Condie et al. |
| 2012/0265196 A1 | 10/2012 | Turner et al. |
| 2013/0023875 A1 | 1/2013 | Harris et al. |
| 2013/0030433 A1 | 1/2013 | Heard |
| 2013/0079762 A1 | 3/2013 | Twomey et al. |
| 2013/0085496 A1 | 4/2013 | Unger et al. |
| 2013/0103024 A1 | 4/2013 | Monson et al. |
| 2013/0123776 A1 | 5/2013 | Monson et al. |
| 2013/0123777 A1 | 5/2013 | Monson et al. |
| 2013/0123782 A1 | 5/2013 | Trees et al. |
| 2013/0131660 A1 | 5/2013 | Monson et al. |
| 2013/0253502 A1 | 9/2013 | Aronow et al. |
| 2013/0338661 A1 | 12/2013 | Behnke, II |
| 2014/0005680 A1 | 1/2014 | Shelton, IV et al. |
| 2014/0094801 A1 | 4/2014 | Boudreaux et al. |
| 2014/0148806 A1 | 5/2014 | Witt et al. |
| 2014/0194914 A1 | 7/2014 | Hunt et al. |
| 2014/0194915 A1 | 7/2014 | Johnson et al. |
| 2014/0257284 A1 | 9/2014 | Artale |
| 2014/0330271 A1 | 11/2014 | Dietz et al. |
| 2014/0343550 A1 | 11/2014 | Faller et al. |
| 2015/0018826 A1 | 1/2015 | Boudreaux |
| 2015/0066022 A1 | 3/2015 | Shelton, IV et al. |
| 2015/0080876 A1 | 3/2015 | Worrell et al. |
| 2015/0080879 A1 | 3/2015 | Trees et al. |
| 2015/0080891 A1 | 3/2015 | Shelton, IV et al. |
| 2015/0133915 A1 | 5/2015 | Strobl et al. |
| 2015/0133921 A1 | 5/2015 | Strobl et al. |
| 2015/0190189 A1 | 7/2015 | Yates et al. |
| 2015/0196352 A1 | 7/2015 | Beckman et al. |
| 2015/0201953 A1 | 7/2015 | Strobl et al. |
| 2015/0230853 A1 | 8/2015 | Johnson et al. |
| 2015/0265347 A1 | 9/2015 | Yates et al. |

FOREIGN PATENT DOCUMENTS

| | | |
|---|---|---|
| DE | 10201569 A1 | 7/2003 |
| EP | 0340803 B1 | 8/1993 |
| EP | 0630612 A1 | 12/1994 |
| EP | 0705571 A1 | 4/1996 |
| EP | 0640317 B1 | 9/1999 |
| EP | 0722696 B1 | 12/2002 |
| EP | 1293172 B1 | 4/2006 |
| EP | 1749479 A1 | 2/2007 |
| EP | 1767157 A1 | 3/2007 |
| EP | 1878399 A1 | 1/2008 |
| EP | 1915953 A1 | 4/2008 |
| EP | 1532933 B1 | 5/2008 |
| EP | 1707143 B1 | 6/2008 |
| EP | 1943957 A2 | 7/2008 |
| EP | 1849424 B1 | 4/2009 |
| EP | 2042117 A1 | 4/2009 |
| EP | 2060238 A1 | 5/2009 |
| EP | 1810625 B1 | 8/2009 |
| EP | 2090238 A1 | 8/2009 |
| EP | 2090256 A2 | 8/2009 |
| EP | 2092905 A1 | 8/2009 |
| EP | 2105104 A2 | 9/2009 |
| EP | 1747761 B1 | 10/2009 |
| EP | 1769766 B1 | 2/2010 |
| EP | 2151204 A1 | 2/2010 |
| EP | 2153791 A1 | 2/2010 |
| EP | 2243439 A1 | 10/2010 |
| EP | 1728475 B1 | 8/2011 |
| EP | 2353518 A1 | 8/2011 |
| EP | 2508143 B1 | 2/2014 |
| GB | 2472216 A | 2/2011 |
| JP | H 08-229050 A | 9/1996 |
| JP | 2008-018226 A | 1/2008 |
| WO | WO 81/03272 A1 | 11/1981 |
| WO | WO 93/07817 | 4/1993 |
| WO | WO 93/22973 A1 | 11/1993 |

(56) References Cited

FOREIGN PATENT DOCUMENTS

| WO | WO 95/10978 A1 | 4/1995 |
|---|---|---|
| WO | WO 96/35382 A1 | 11/1996 |
| WO | WO 97/10764 A1 | 3/1997 |
| WO | WO 98/00069 A1 | 1/1998 |
| WO | WO 98/40020 A1 | 9/1998 |
| WO | WO 98/57588 A1 | 12/1998 |
| WO | WO 99/23960 A1 | 5/1999 |
| WO | WO 99/40861 A1 | 8/1999 |
| WO | WO 00/24330 A1 | 5/2000 |
| WO | WO 00/24331 A1 | 5/2000 |
| WO | WO 00/25691 A1 | 5/2000 |
| WO | WO 01/28444 A1 | 4/2001 |
| WO | WO 02/080797 A1 | 10/2002 |
| WO | WO 03/001986 A2 | 1/2003 |
| WO | WO 03/013374 A1 | 2/2003 |
| WO | WO 03/020339 A2 | 3/2003 |
| WO | WO 03/028541 A2 | 4/2003 |
| WO | WO 03/030708 A2 | 4/2003 |
| WO | WO 03/068046 A2 | 8/2003 |
| WO | WO 2004/011037 A2 | 2/2004 |
| WO | WO 2004/078051 A2 | 9/2004 |
| WO | WO 2005/052959 A2 | 6/2005 |
| WO | WO 2006/021269 A1 | 3/2006 |
| WO | WO 2006/036706 A1 | 4/2006 |
| WO | WO 2006/055166 A2 | 5/2006 |
| WO | WO 2008/020964 A2 | 2/2008 |
| WO | WO 2008/045348 A2 | 4/2008 |
| WO | WO 2008/099529 A1 | 8/2008 |
| WO | WO 2008/101356 A1 | 8/2008 |
| WO | WO 2009/022614 A1 | 2/2009 |
| WO | WO 2009/036818 A1 | 3/2009 |
| WO | WO 2009/039179 A1 | 3/2009 |
| WO | WO 2009/059741 A1 | 5/2009 |
| WO | WO 2009/082477 A2 | 7/2009 |
| WO | WO 2009/149234 A1 | 12/2009 |
| WO | WO 2010/017266 A1 | 2/2010 |
| WO | WO 2010/104755 A1 | 9/2010 |
| WO | WO 2011/084768 A1 | 7/2011 |
| WO | WO 2011/089717 A1 | 7/2011 |
| WO | WO 2011/144911 A1 | 11/2011 |
| WO | WO 2013/034629 A1 | 3/2013 |
| WO | WO 2013/062978 A2 | 5/2013 |

OTHER PUBLICATIONS

Sullivan, "Optimal Choice for Number of Strands in a Litz-Wire Transformer Winding," IEEE Transactions on Power Electronics, vol. 14, No. 2, Mar. 1999, pp. 283-291.
International Search Report for PCT/US2012/061504, dated May 2, 2013 (6 pages).
Written Opinion for PCT/US2012/061504, dated May 2, 2013 (11 pages).
Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).
Hörmann et al., "Reversible and irreversible denaturation of collagen fibers." Biochemistry, 10, pp. 932-937 (1971).
Henriques. F.C., "Studies in thermal injury V. The predictability and the significance of thermally induced rate processes leading to irreversible epidermal injury." Archives of Pathology, 434, pp. 489-502 (1947).
Arnoczky et al., "Thermal Modification of Conective Tissues: Basic Science Considerations and Clinical Implications," J. Am Acad Orthop Surg. vol. 8, No. 5, pp. 305-313 (Sep./Oct. 2000).
Chen et al., "Heat-induced changes in the mechanics of a collagenous tissue: pseudoelastic behavior at 37° C.," Journal of Biomechanics, 31, pp. 211-216 (1998).

Chen et al., "Heat-Induced Changes in the Mechanics of a Collagenous Tissue: Isothermal Free Shrinkage," Transactions of the ASME, vol. 119, pp. 372-378 (Nov. 1997).
Chen et al., "Heat-Induced Changes in the Mechanics of a Collagenous Tissue: Isothermal, Isotonic Shrinkage," Transactions of the ASME, vol. 120, pp. 382-388 (Jun. 1998).
Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).
Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).
Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).
Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=MI&sp=1 . . . , accessed Aug. 25, 2009.
Lee et al., "A multi-sample denaturation temperature tester for collagenous biomaterials," Med. Eng. Phy., vol. 17, No. 2, pp. 115-121 (Mar. 1995).
Moran et al., "Thermally Induced Shrinkage of Joint Capsule," Clinical Orthopaedics and Related Research, No. 281, pp. 248-255 (Dec. 2000).
Wall et al., "Thermal modification of collagen," J Shoulder Elbow Surg, No. 8, pp. 339-344 (Jul./Aug. 1999).
Wells et al., "Altered Mechanical Behavior of Epicardium Under Isothermal Biaxial Loading," Transactions of the ASME, Journal of Biomedical Engineering, vol. 126, pp. 492-497 (Aug. 2004).
Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).
Humphrey, J.D., "Continuum Thermomechanics and the Clinical Treatment of Disease and Injury," Appl. Mech. Rev., vol. 56, No. 2 pp. 231-260 (Mar. 2003).
Kurt Gieck & Reiner Gieck, *Engineering Formulas* § Z.7 (7th ed. 1997).
National Semiconductors Temperature Sensor Handbook—http://www.national.com/appinfo/tempsensors/files/temphb.pdf; accessed online: Apr. 1, 2011.
Glaser and Subak-Sharpe, *Integrated Circuit Engineering*, Addison-Wesley Publishing, Reading, MA (1979). (book—not attached).
Wright, et al., "Time-Temperature Equivalence of Heat-Induced Changes in Cells and Proteins," Feb. 1998. ASME Journal of Biomechanical Engineering, vol. 120, pp. 22-26.
Covidien Brochure, [Value Analysis Brief], LigaSure Advance™ Pistol Grip, dated Rev. Apr. 2010 (7 pages).
Covidien Brochure, LigaSure Impact™ Instrument LF4318, dated Feb. 2013 (3 pages).
Covidien Brochure, LigaSure Atlas™ Hand Switching Instruments, dated Dec. 2008 (2 pages).
Covidien Brochure, The LigaSure™ 5 mm Blunt Tip Sealer/Divider Family, dated Apr. 2013 (2 pages).
Covidien Brochure, The LigaSure Precise™ Instrument, dated Mar. 2011 (2 pages).
Erbe Electrosurgery VIO® S, (2012), p. 7, 12 pages, accessed Mar. 31, 2014 at http://www.erbe-med.com/erbe/media/Marketingmaterialien/85140-170_ERBE_EN_VIO_200_S_D027541.
Jang, J. et al. "Neuro-fuzzy and Soft Computing." Prentice Hall, 1997, pp. 13-89, 199-293, 335-393, 453-496, 535-549.
Douglas, S.C. "Introduction to Adaptive Filter". Digital Signal Processing Handbook. Ed. Vijay K. Madisetti and Douglas B. Williams. Boca Raton: CRC Press LLC, 1999.
U.S. Appl. No. 14/227,699, filed Mar. 27, 2014.
U.S. Appl. No. 14/227,708, filed Mar. 27, 2014.

\* cited by examiner

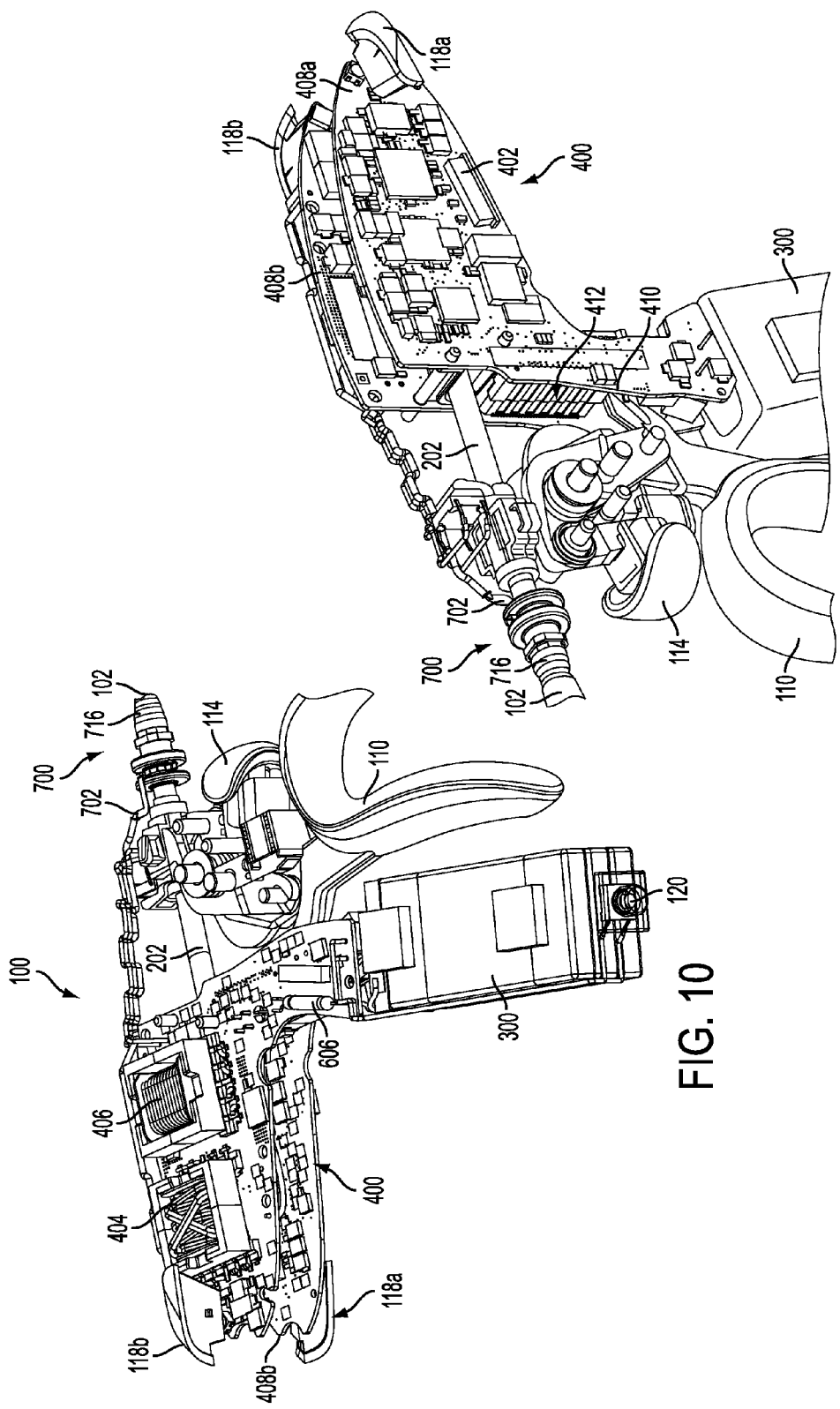

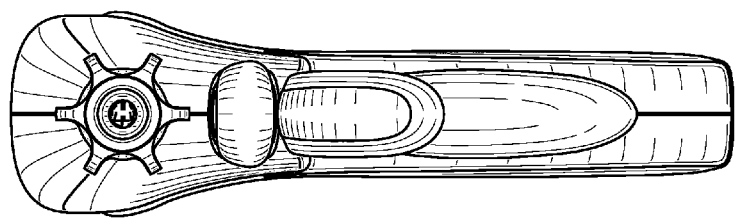
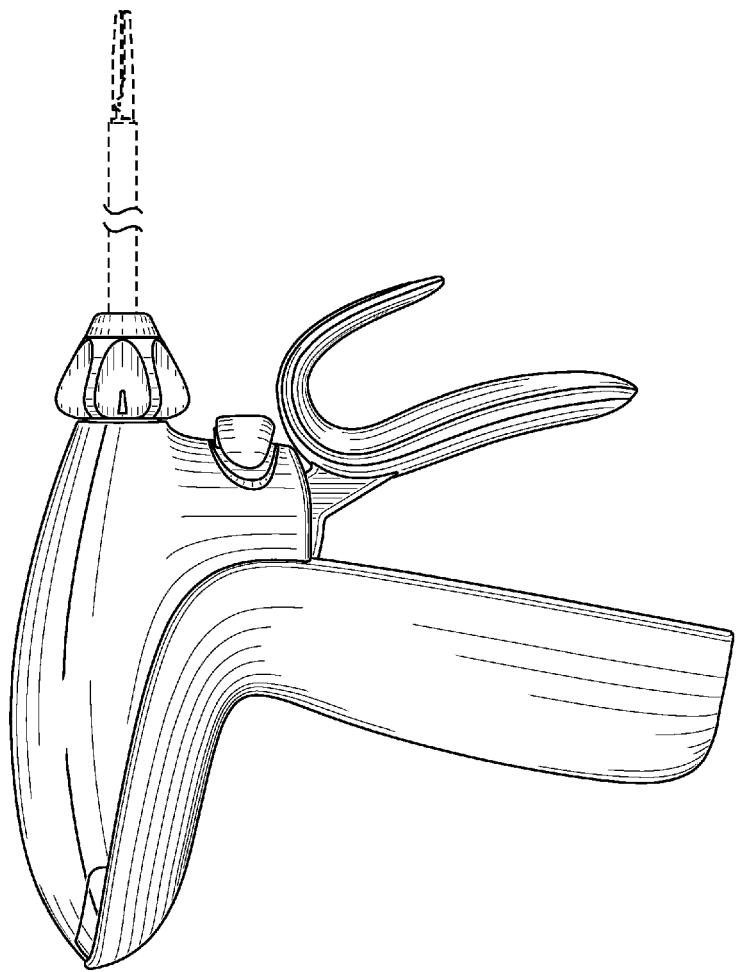
FIG. 52
FIG. 53

LITZ WIRE BATTERY POWERED DEVICE

CROSS-REFERENCE TO RELATED APPLICATIONS

This application claims the benefit of U.S. Provisional Patent Application Ser. No. 61/550,768, entitled "MEDICAL INSTRUMENT," filed on Oct. 24, 2011, which is incorporated herein by reference in its entirety.

This application is related to the following commonly assigned U.S. and PCT International Patent Applications:

U.S. patent application Ser. No. 13/658,786, entitled "BATTERY SHUT-OFF ALGORITHIM IN A BATTERY POWERED DEVICE," now published as U.S. Patent Application Publication No. 2013-0123776, which is incorporated herein by reference in its entirety.

U.S. patent application Ser. No. 13/658,787, entitled "USER INTERFACE IN A BATTERY POWERED DEVICE," now published as U.S. Patent Application Publication No. 2013-0103024, which is incorporated herein by reference in its entirety.

U.S. patent application Ser. No. 13/658,790, entitled "BATTERY INITIALIZATION CLIP," now published as U.S. Patent Application Publication No. 2013-0131660, which is incorporated herein by reference in its entirety.

U.S. patent application Ser. No. 13/658,791, entitled "BATTERY DRAIN KILL FEATURE IN A BATTERY POWERED DEVICE," now published as U.S. Patent Application Publication No. 2013-0123777, which is incorporated herein by reference in its entirety.

U.S. patent application Ser. No. 13/658,792, entitled "TRIGGER LOCKOUT MECHANISM," now published as U.S. Patent Application Publication No. 2013-0123782, which is incorporated herein by reference in its entirety.

PCT International Patent Application Serial No. PCT/US2012/061504, entitled "MEDICAL INSTRUMENT," now published as International Application Publication No. WO 2013/062978, which is incorporated herein by reference in its entirety.

BACKGROUND

The present disclosure relates to the field of medical instruments and in particular, although not exclusively, to electrosurgical instruments. The present disclosure also relates to drive circuits and methods for driving such medical instruments. Additionally, the present disclosure is directed to lockout mechanisms, user interfaces, initialization techniques, and battery power conservation circuits and methods for such medical instruments.

Many surgical procedures require cutting or ligating blood vessels or other internal tissue. Many surgical procedures are performed using minimally invasive techniques where a handheld instrument is used by the surgeon to perform the cutting or ligating. Conventional hand-held electrosurgical instruments are generally large and bulky and require large power supplies and control electronics that are connected to the instrument through an electrical supply line.

Conventional corded electrosurgical instruments are large in size, have large power supplies and control electronics, and take up a lot of space in the operating room. Corded electrosurgical instruments are particularly cumbersome and difficult to use during a surgical procedure in part due to tethering of the hand-held electrosurgical instrument to the power supply and control electronics and the potential for cord entanglement. Some of these deficiencies have been overcome by providing battery powered hand-held electrosurgical instruments in which the power and control electronics are mounted within the instrument itself, such as within the handle of the instrument, to reduce the size of the electrosurgical instrument and make such instruments easier to use during surgical procedures.

Electrosurgical medical instruments generally include an end effector having an electrical contact, a radio frequency (RF) generation circuit for generating an RF drive signal and to provide the RF drive signal to the at least one electrical contact where the RF generation circuit also includes a resonant circuit. The RF circuit includes circuitry to generate a cyclically varying signal, such as a square wave signal, from a direct current (DC) energy source and the resonant circuit is configured to receive the cyclically varying signal from the switching circuitry. The DC energy source is generally provided by one or more batteries that can be mounted in a handle portion of the housing of the instrument, for example.

The design of battery powered hand-held electrosurgical instruments requires the electronics in the power supply and RF amplifier sections to have the highest efficiency possible in order to minimize the heat rejected into the relatively small handheld package. Increased efficiency also improves the storage and operational life of the battery. Increased efficiency also minimizes the size of the required battery or extends the life of a battery of a given size. Thus, there is a need for battery powered hand-held electrosurgical instruments having higher efficiency power supply and RF amplifier sections.

SUMMARY

In one embodiment, a medical instrument includes a housing and a handle for gripping by a user, an end effector coupled to the handle and having at least one electrical contact, a battery, and a radio frequency (RF) generation circuit coupled to and operated by the battery. The RF drive circuit is operable to generate an RF drive signal and to provide the RF drive signal to the at least one electrical contact. The RF generation circuit is supported by the housing. The RF generation circuit comprises a resonant circuit comprising at least one inductive element constructed of litz wire.

FIGURES

FIG. 10 illustrates a second electronic substrate comprising an inductor and a transformer that form a part of the RF energy circuit, according to one embodiment.

FIG. 11 illustrates two separate substrates provided where the digital circuit elements are located on a first substrate and the RF amplifier section and other analog circuit elements are located on a second substrate, according to one embodiment.

FIGS. 49-57 illustrates the ornamental design for a surgical instrument handle assembly as shown and described, according to one embedment, where:

FIG. 49 is a left perspective view of a handle assembly for a surgical instrument.

FIG. 50 is a right perspective view thereof.

FIG. 51 is a left perspective view thereof.

FIG. 52 is a left view thereof.

FIG. 53 is a front view thereof.

FIG. 54 is a right view thereof.

FIG. 55 is a rear view thereof.

FIG. 56 is a top view thereof.

FIG. 57 is a bottom view thereof.

DESCRIPTION

Before explaining various embodiments of medical instruments in detail, it should be noted that the illustrative embodiments are not limited in application or use to the details of construction and arrangement of parts illustrated in the accompanying drawings and description. The illustrative embodiments may be implemented or incorporated in other embodiments, variations and modifications, and may be practiced or carried out in various ways. Further, unless otherwise indicated, the terms and expressions employed herein have been chosen for the purpose of describing the illustrative embodiments for the convenience of the reader and are not for the purpose of limitation thereof.

Further, it is understood that any one or more of the following-described embodiments, expressions of embodiments, examples, can be combined with any one or more of the other following-described embodiments, expressions of embodiments, and examples.

The present disclosure is directed generally to medical instruments and in particular, although not exclusively, to electrosurgical instruments. The present disclosure also is directed to drive circuits and methods for driving such medical instruments. Additionally, the present disclosure is directed to lockout mechanisms, user interfaces, initialization techniques, and battery power conservation circuits and methods for such surgical instruments.

For clarity of disclosure, the terms "proximal" and "distal" are defined herein relative to a surgeon grasping the electrosurgical instrument. The term 'proximal" refers the position of an element closer to the surgeon and the term "distal" refers to the position of an element further away from the surgeon.

Many surgical procedures require cutting or ligating blood vessels or other vascular tissue. With minimally invasive surgery, surgeons perform surgical operations through a small incision in the patient's body. As a result of the limited space, surgeons often have difficulty controlling bleeding by clamping and/or tying-off transected blood vessels. By utilizing electrosurgical forceps, a surgeon can cauterize, coagulate/desiccate, and/or simply reduce or slow bleeding by controlling the electrosurgical energy applied through jaw members of the electrosurgical forceps, otherwise referred to as clamp arms.

Figure 1:
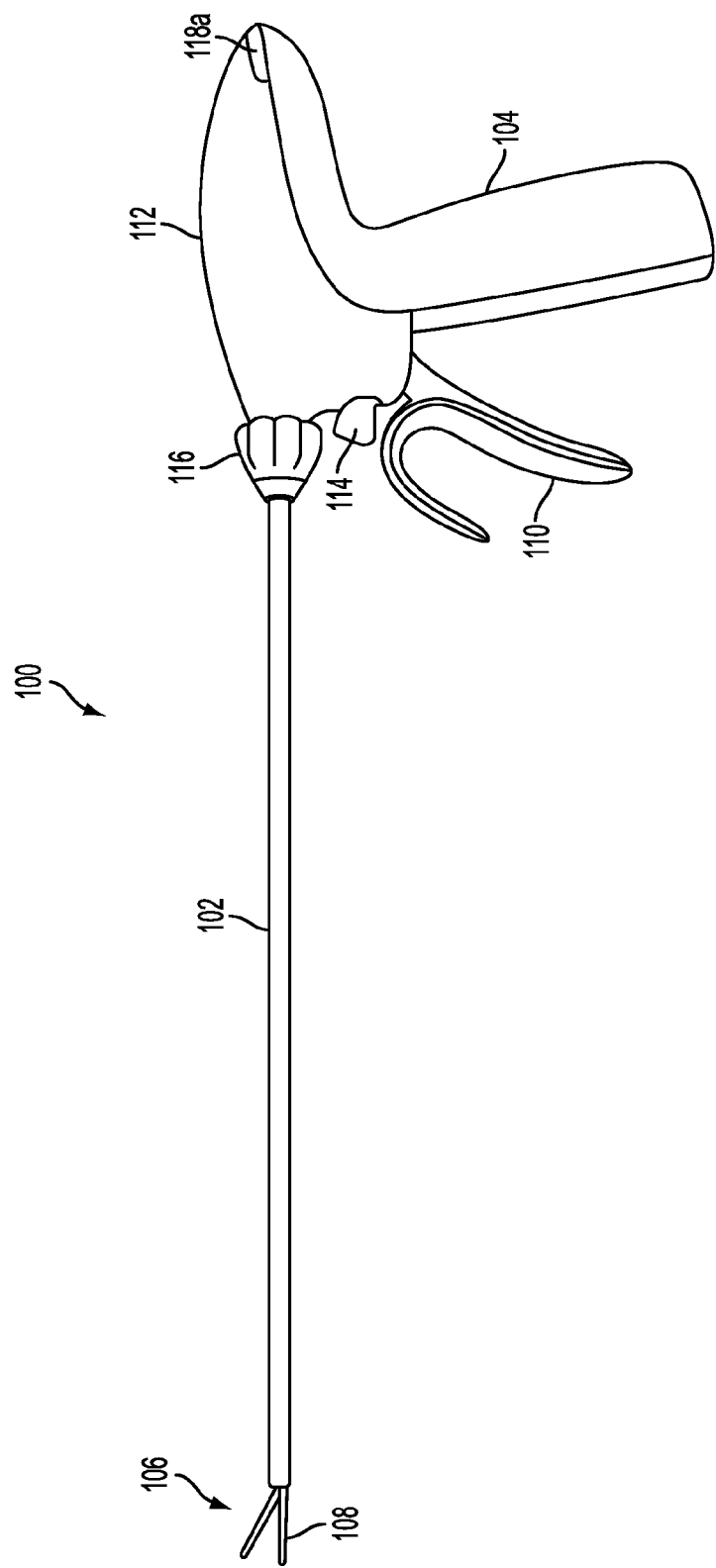
FIG. 1 illustrates the form of an electrosurgical medical instrument that is designed for minimally invasive medical procedures, according to one embodiment.

FIG. 1 illustrates the form of an electrosurgical medical instrument 100 that is designed for minimally invasive medical procedures, according to one embodiment. As shown, the instrument 100 is a self contained device, having an elongate shaft 102 that has a housing 112 with a handle 104 connected to the proximal end of the shaft 102 and an end effector 106 connected to the distal end of the shaft 102. In this embodiment, the end effector 106 comprises medical forceps 108 having a movable jaw member and a cutting blade or knife (not shown) coupled to an inner sheath (not shown) located within the shaft 102 that are controlled by the user manipulating a control lever 110 (e.g., hand trigger) portion of the handle 104. In the illustrated embodiment, the control lever 110 (e.g., hand trigger) is in the form of a hook (e.g., shepherd's hook) having a curved front portion and a rear portion where the rear portion extends below the front portion. The curved front portion and the rear portion define an aperture therebetween to receive the user's hand to operate the control lever 110. During a surgical procedure, the shaft 102 is inserted through a trocar to gain access to the patient's interior and the operating site.

The surgeon will manipulate the forceps 108 using the handle 104, the control lever 110, and rotation knob 116 until the forceps 108 are located around the vessel to be cauterized. The rotation knob 116 is coupled to the shaft 102 and the end effector 106. Rotation of the rotation knob 116 causes rotation of the shaft 102 and the end effector 106. In one embodiment, the shaft 102 is continuously rotatable greater than 360° using the rotation knob 116. To perform the desired cauterization Electrical energy at an RF frequency (it has been found that frequencies above about 50 kHz (e.g., ~100 kHz and higher) do not affect the human nervous system) is then applied by, in a controlled manner, to the forceps 108 by actuating an activation button 114. The activation button 114 has a partial activation position and a full activation position.

As shown in FIG. 1, in this embodiment, the handle 104 houses batteries and the housing houses control electronics for generating and controlling the electrical energy required to perform the cauterization. In this way, the instrument 100 is self contained in the sense that it does not need a separate control box and supply wire to provide the electrical energy to the forceps 108. The instrument 100 also comprises a first visual feedback element 118a on the proximal end of the housing 112 to indicate that the device is ready for use and functioning normally, that there are a limited number of transections remaining, that RF energy is being delivered, that an alert condition or fault exists, that the initialization clip was removed, among other indications. In one embodiment, the first visual feedback element 118a is a light emitting diode (LED), without limitation. In one embodiment, the first visual feedback element 118a is a tri-color LED. In one embodiment, the instrument 100 comprises an integral generator and a non-reusable battery.

Figure 2:
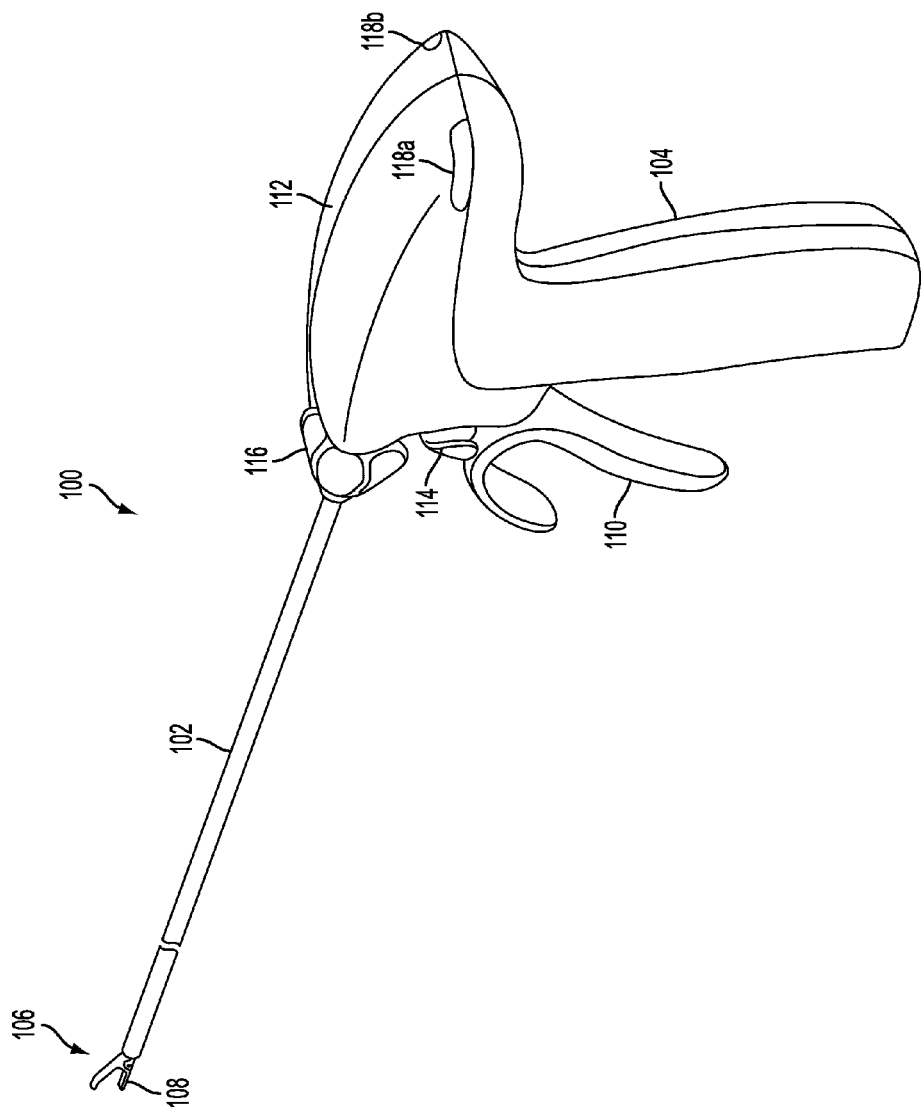
FIG. 2 illustrates another view of the electrosurgical medical instrument shown in FIG. 1.

FIG. 2 illustrates another view of the electrosurgical medical instrument 100 shown in FIG. 1. In one embodiment, the instrument 100 comprises a second visual feedback element 118b located on the proximal end of the housing 112. In one embodiment, the second visual feedback element 118b performs the same function as the first visual feedback element 118a. In one embodiment, the second visual feedback element 118b is an LED, without limitation. In one embodiment, the second visual feedback element 118b is a tri-color LED.

Figure 3:
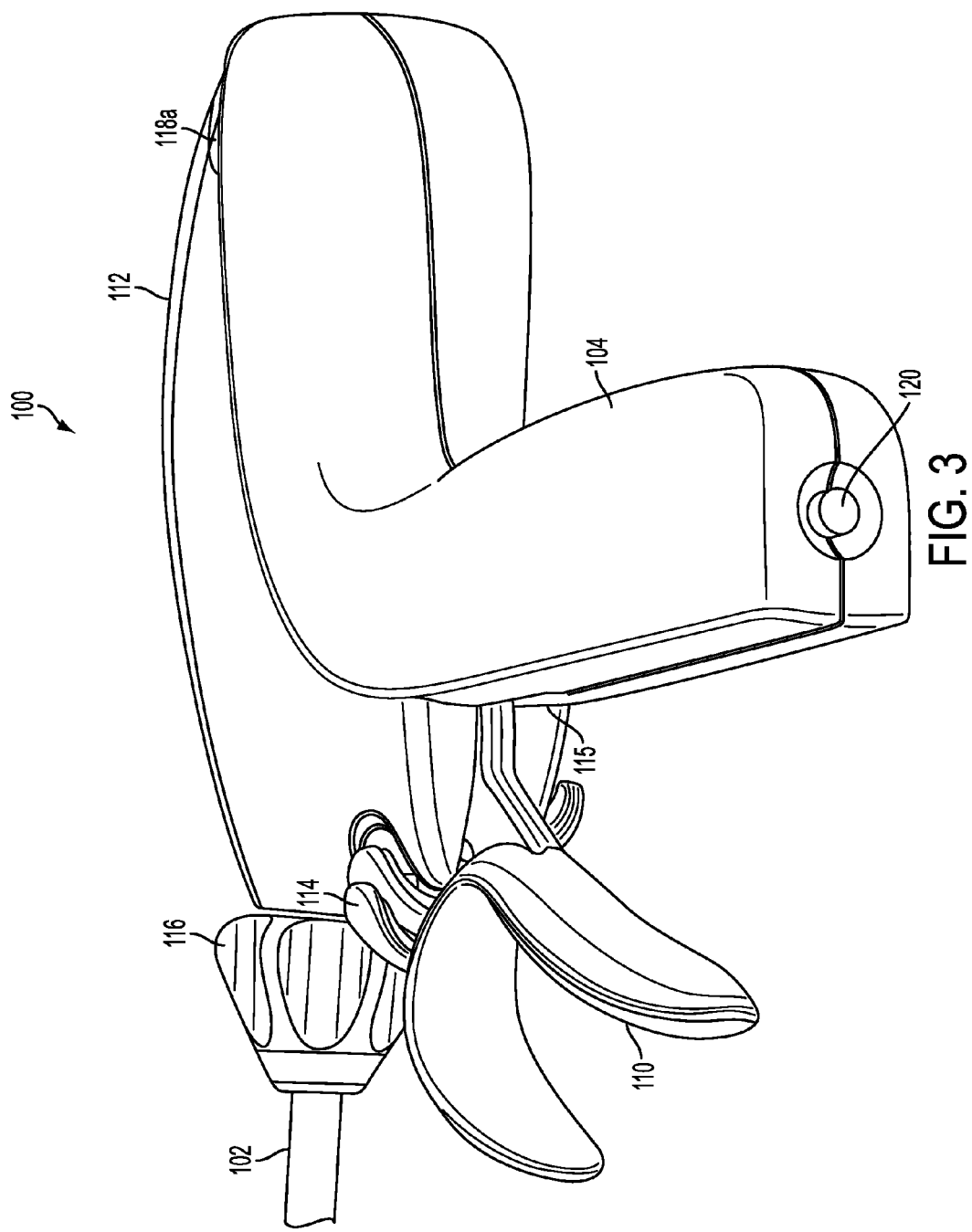
FIG. 3 illustrates another view of the electrosurgical medical instrument shown in FIG. 1.

FIG. 3 illustrates another view of the electrosurgical medical instrument 100 shown in FIG. 1. In one embodiment, the instrument 100 comprises a disposal button 120 located on the bottom of the handle 104, for example. The disposal button 120 is used to deactivate the instrument 100. In one embodiment, the instrument 100 may be deactivated by pushing and holding the disposal button 120 for a predetermined period. For example, the instrument 100 may be deactivated by pushing and holding the disposal button 120 for about four seconds. In one embodiment, the instrument 100 will automatically deactivate after a predetermined period. For example, the instrument 100 will automatically deactivate either eight or 10 hours after completion of the first cycle. An aperture 115 formed in the handle 104 provides a path for audio waves or a means for sound generated by an audio feedback element such as a piezoelectric buzzer to escape, for example, from within the handle 104. In one embodiment, the piezoelectric buzzer operates at 65 dBa at one meter at a frequency between about 2.605 kHz to 2.800 kHz, for example. The aperture 115 enables the sound to escape the handle 104 so that it is comfortably audible to the surgeon while operating the medical instrument 100.

Figure 4:
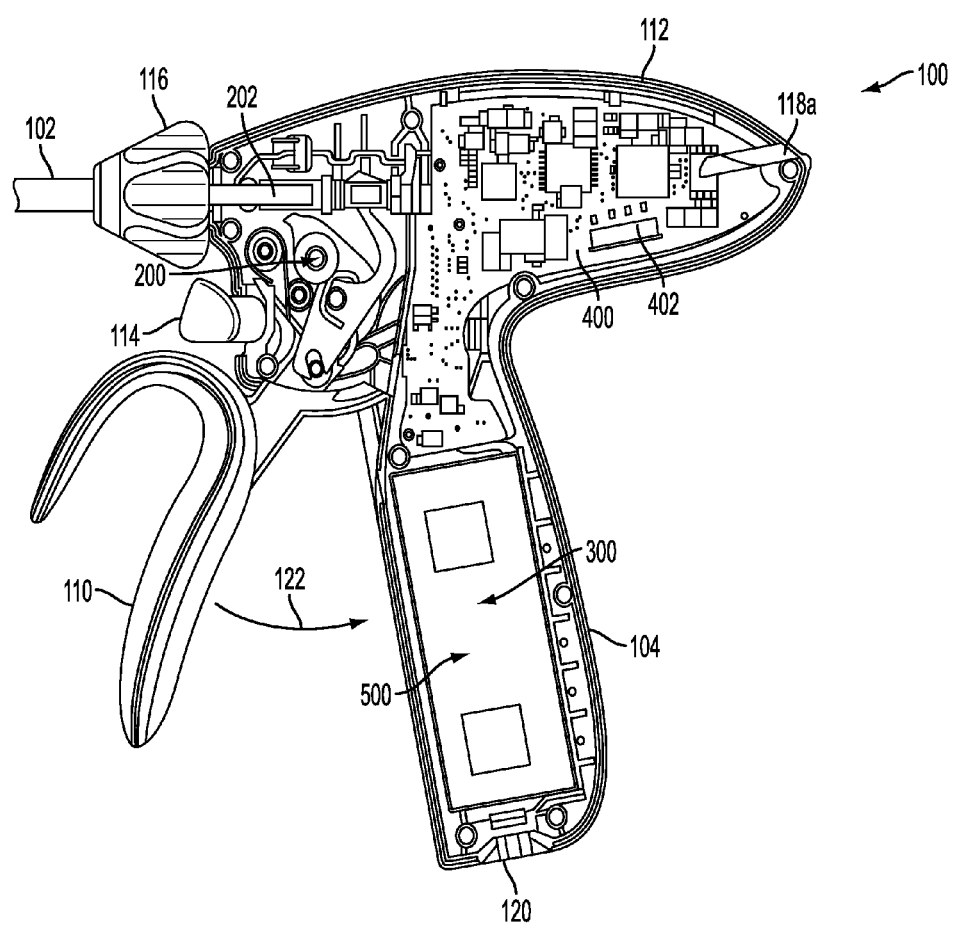
FIG. 4 illustrates a sectional view of the electrosurgical medical instrument illustrating elements thereof contained within a housing, according to one embodiment.

FIG. 4 illustrates a sectional view of the electrosurgical medical instrument 100 illustrating elements thereof contained within the housing 112, according to one embodiment. In one embodiment, the instrument 100 comprises a knife lockout mechanism 200 to prevent the advancement of an inner sheath 202, which is coupled to a blade (not shown) portion of the medical forceps 108. In the illustrated embodiments, the medical forceps 108 having a movable jaw member that is pivotally movable to clamp down on a vessel when the control lever 110 is squeezed proximally in the direction of arrow 122. The cutting blade or knife (not shown) portion of the medical forceps 108 also advances distally when the control lever 110 is squeezed proximally. The cutting blade, sometime referred to as the knife, is for cutting the vessel after it has been cauterized. To prevent a "cold cut" of the vessel, which is defined as cutting with no application of energy to the vessel, a knife lockout mechanism 200 prevents the control lever 110 from being squeezed and thus prevents the blade from being advanced until the activation button 114 is fully engaged and a suitable amount of RF energy is applied to the vessel to properly cauterize it.

The knife lockout mechanism 200 ensures that the activation button 114 is fully depressed to activate the RF energy source such that energy is delivered to the vessel prior to cutting. When the activation button 114 is fully engaged, the knife lockout mechanism 200 enables the control lever 110 to be squeezed proximally in the direction of arrow 122. This action advances the inner sheath 202 distally to close the jaw members of the electrosurgical forceps 108 while the cutting blade is simultaneously advanced to cut the vessel after it is fully cauterized. Therefore, electrosurgical energy is applied to the vessel through the jaw members of the electrosurgical forceps 108 before the cutting blade advances.

Also shown in FIG. 4 is an integral energy source 300, according to one embodiment. In the embodiment illustrated in FIG. 4, the integral energy source 300 may be a non-replaceable DC energy source such as a battery 300 that fits within the handle portion 104 of the housing 112. One embodiment of the energy source 300 is described in more detail hereinbelow.

In one embodiment, the battery 300 is a 1000 mAh, triple-cell Lithium Ion Polymer battery, Lithium battery, among others. The battery 300 will be fully charged prior to Ethylene Oxide (EtO) sterilization, and will have a fully charged voltage of about 12V to about 12.6V. The battery 300 will have two 20 A fuses fitted to the substrate which connects the cells, one in line with each terminal. In other embodiments, the battery capacity may be greater than 1000 mAh, such as, up to about 3000 mAh, for example.

In one embodiment, the minimum distance between terminals of the battery 300 may be about 3 mm such that sparking conditions require an atmosphere with a dielectric breakdown of ≤4200V/m. Even at the lowest pressures encountered in an EtO cycle, for a condition of pure EtO, across a 3 mm gap the breakdown voltage is approximately 450V. This is more than an order of magnitude greater than the maximum battery voltage, and this is further mitigated by the use of a Nitrogen blanket during the sterilization process.

Also shown in FIG. 4 is an electronics system 400, according to one embodiment. In one embodiment, the electronics system 400 comprises an RF generation circuit to generate an RF drive signal and to provide the RF drive signal to the at least one electrical contact where the RF generation circuit also includes a resonant circuit. The electronics system 400 also comprises control elements such as one or more than one microprocessor (or micro-controller) and additional digital electronic elements to control the logical operation of the instrument 100. One embodiment of the electronics system 400 is described hereinbelow. The electronics system 400 including the RF generation circuit is supported by the housing 112. In one embodiment, RF generation circuit to generate an RF drive signal is integral to the housing 112 and the battery 300 is non-reusable.

Also referenced in FIG. 4 is a logical lockout mechanism 500, in accordance with one embodiment. The logical lockout mechanism works in cooperation with an initialization clip 600 (see FIGS. 7-9) and 650 (see FIGS. 20-21) to prevent operation of the instrument 100 until it is removed. One embodiment of the logical lockout mechanism 500 is described hereinbelow.

Figure 5:
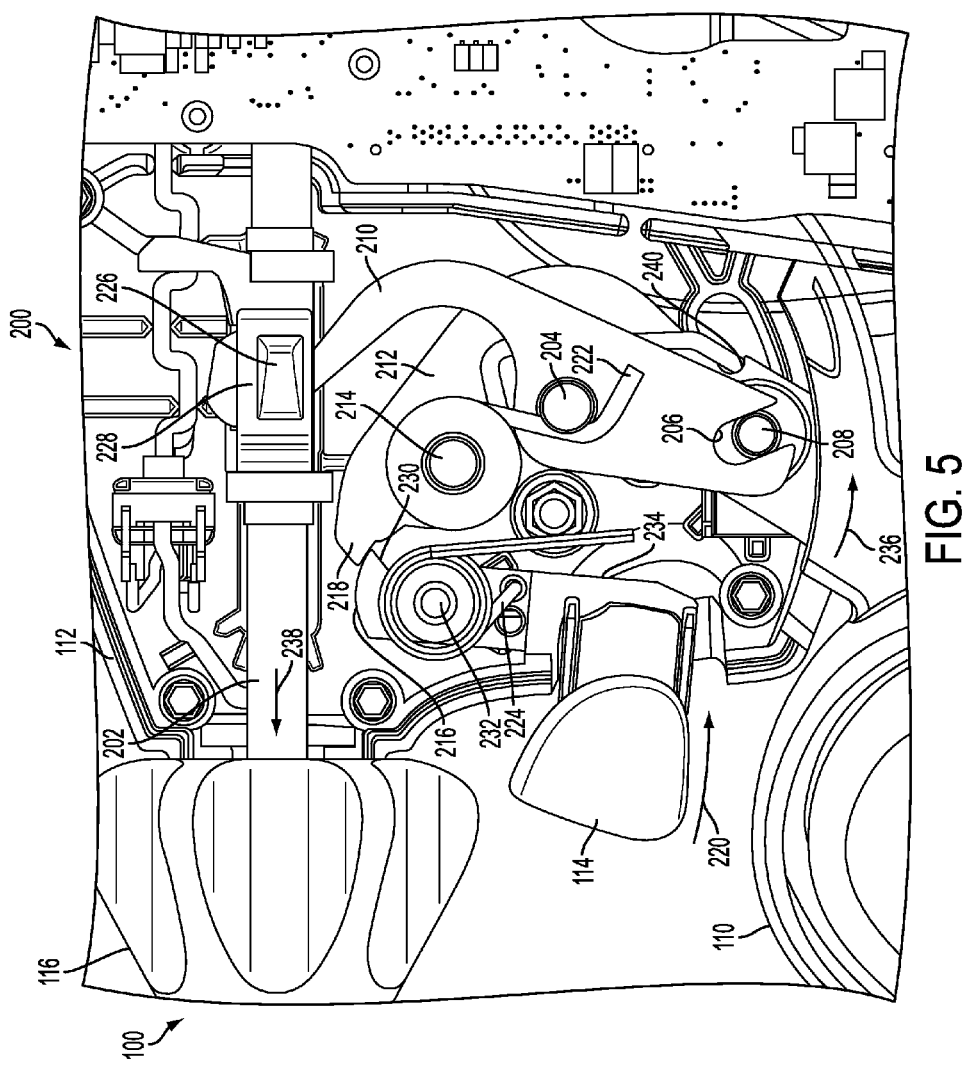
FIG. 5 illustrates a partial sectional view of the electrosurgical medical instrument in a locked out position to prevent the actuation of the control lever, according to one embodiment.

FIG. 5 illustrates the electrosurgical medical instrument 100 in a locked out position to prevent the actuation of the control lever 110, according to one embodiment. The control lever 110 comprises a trigger lever 212 portion that is configured to rotate about a trigger pivot 214 when the control lever 110 is squeezed in the direction of arrow 122 (FIG. 4), unless the instrument is in locked out mode.

In the locked out mode, the trigger lever 212 portion of the control lever 110 is prevented from rotating about the trigger pivot 214 because a projection 218 of the trigger lever 212 engages a top surface 216 of an activation button lever 234 that rotates about activation button pivot 232 when the activation button 114 is squeezed in the direction of arrow 220. A contact button torsion spring 224 keeps the activation button 114 in an outwardly position to disable the electrosurgical energy from being applied while simultaneously engaging the projection 218 of the trigger lever 212 with the top surface 216 to lockout the instrument 100 until the activation button 114 is fully engaged in the direction of arrow 220.

A second trigger lever 210 comprises a first end that defines a pin slot 206 and a second end that defines a tab 226. The pin slot 206 engages a pin 208 portion of the trigger lever 212. As the trigger lever 212 rotates in the direction of arrow 236 about trigger pivot 214 the pin 208 moves within the pin slot 206 to apply a rotation movement to the second trigger lever 210. The tab 226 engages an aperture 228 to mechanically couple the second trigger lever 210 to the inner sheath 202. Thus, as the trigger lever 212 moves in the direction of arrow 236, the second trigger lever 210 rotates about lever pivot 204 to apply a linear translation motion to the inner sheath 202 in the direction of arrow 238. A trigger torsion spring 222 engages the second trigger lever 210 at a notch 240 formed on the second trigger lever 210. The trigger torsion spring 222 torque balances the hand force applied to the second trigger lever 210 through the control lever 110 about the trigger pivot 214.

Figure 6:
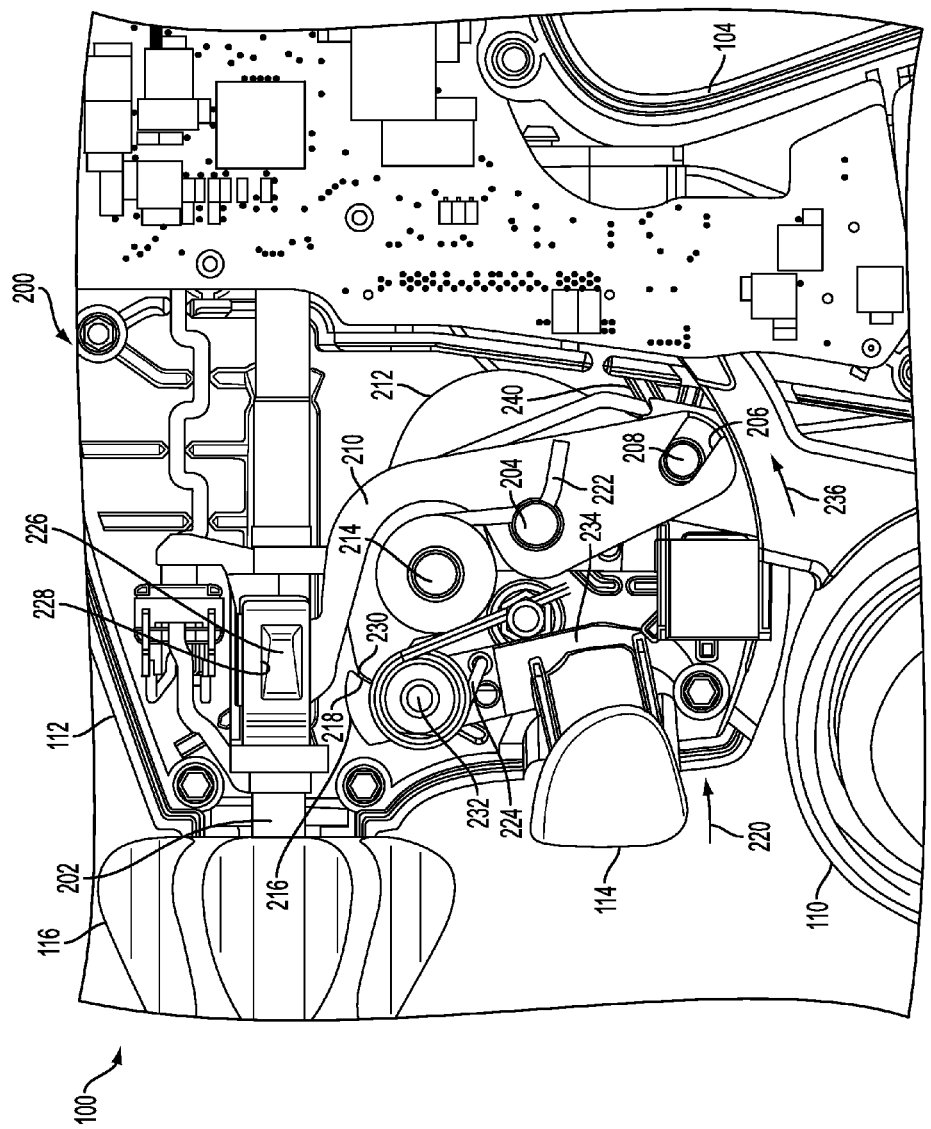
FIG. 6 illustrates a partial sectional view of the electrosurgical medical instrument in a full stroke position, according to one embodiment.

FIG. 6 illustrates the electrosurgical medical instrument 100 in a full stroke position, according to one embodiment. In order to release the lockout mechanism 200, the activation button 114 is fully engaged in the direction of arrow 220 to cause the activation button lever 234 to rotate about activation button pivot 232 and release the top surface 216 from engaging the projection 218. This allows the projection 218 to slidably rotate past a surface 230 of the activation button lever 234 as the trigger lever 212 slidably rotates in the direction of arrow 236 about trigger pivot 214 as the control lever 110 is squeezed, or actuated, proximally by the surgeon. During the control lever 110 actuation period, the pin 208 is engaged by the pin slot 206 slidably moving therein and rotating the second trigger lever 210 about the lever pivot 204. As shown in FIG. 6, in the full stroke position, the inner sheath 202 is fully advanced in the distal direction in accordance with the translation motion applied by the tab 26 and aperture 228 as the second trigger lever 210 is fully rotated about the lever pivot 204. Also of note, the trigger and contact button torsion springs 222, 224, respectively, are torqued in order to return the control lever 110 and contact button 114, respectively, to their normal locked out deactivated positions.

Figure 7:
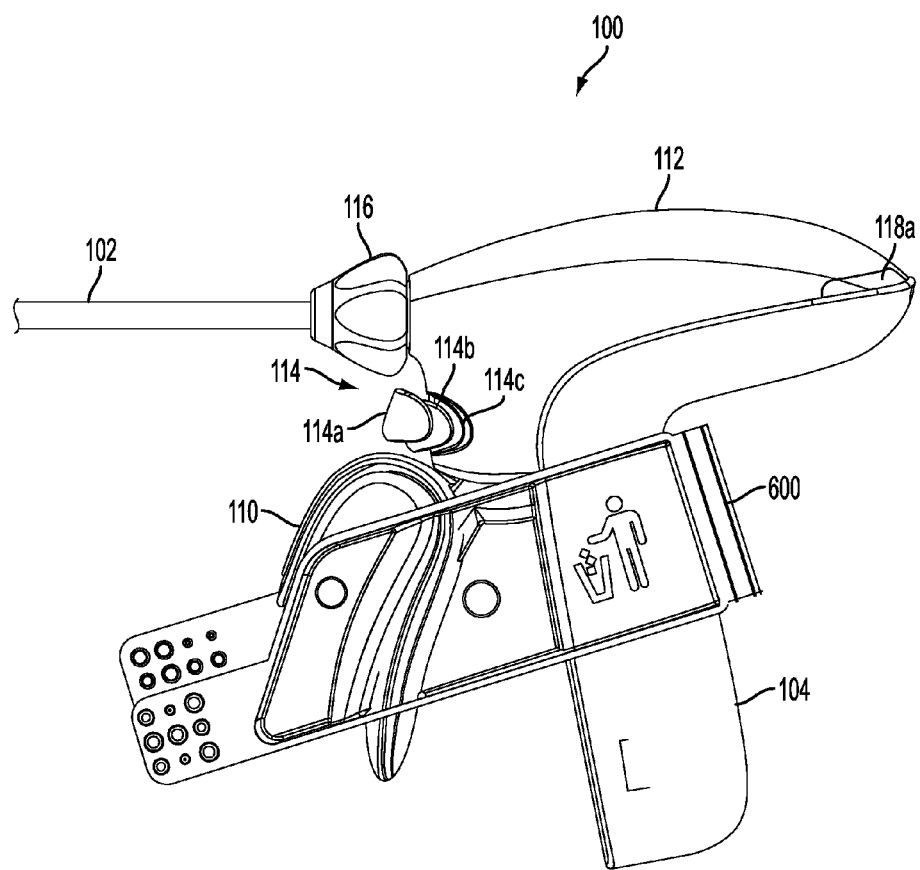
FIG. 7 illustrates the electrosurgical medical instrument comprising an initialization clip interfering with the handle, according to one embodiment.

FIG. 7 illustrates the electrosurgical medical instrument 100 comprising an initialization clip 600, according to one embodiment. The clip 600 prevents firing the medical instrument 100 without enabling and also provides some protection during shipment. The initialization clip 600 is applied to the instrument 100 after initialization at the factory and stays on the instrument 100 during storage. Upon removal of the clip 600, the instrument 100 is enabled. In one embodiment, if the instrument 100 has completed one full energy activation cycle (described in more detail hereinbelow) and the clip 600 is re-installed, the instrument 100 will not function upon removal of the clip 600 a second time.

In addition to the clip 600, other techniques for activating the battery 300 are contemplated by the present disclosure. In one embodiment, described but not shown, a "Pull Tab" may be employed to activate the battery 300. In one embodiment, the Pull Tab may comprise a plastic strip that physically separates the battery contacts acting as an insulator. A multi-stage version of this embodiment enables production testing.

In another embodiment, described but not shown, a breakaway plastic tab may be employed to activate the battery 300. In one embodiment, the breakaway plastic tab separates the battery 300 contacts and cannot be replaced.

In another embodiment, described but not shown, a mechanical mechanism may be employed to activate the battery 300. In one embodiment, the mechanical mechanism may be activated from outside the battery 300 to open the battery 300 contacts via a mechanical means.

In another embodiment, described but not shown, a removable battery is provided, where the battery is removed prior to the sterilizing the medical instrument 100. The removable battery may be sterilized using a separate sterilization method. For example, the medical instrument 100 may be sterilized by EtO and the battery by $H_2O_2$ (hydrogen peroxide), e-beam sterilization, or any suitable sterilization technique that is non-destructive to the battery.

In another embodiment, described but not shown, a Hall-effect device may be employed as an activation means. The Hall-effect device is responsive to a magnetic field and can be used to detect the presence or absence of a magnetic field.

Figure 8:
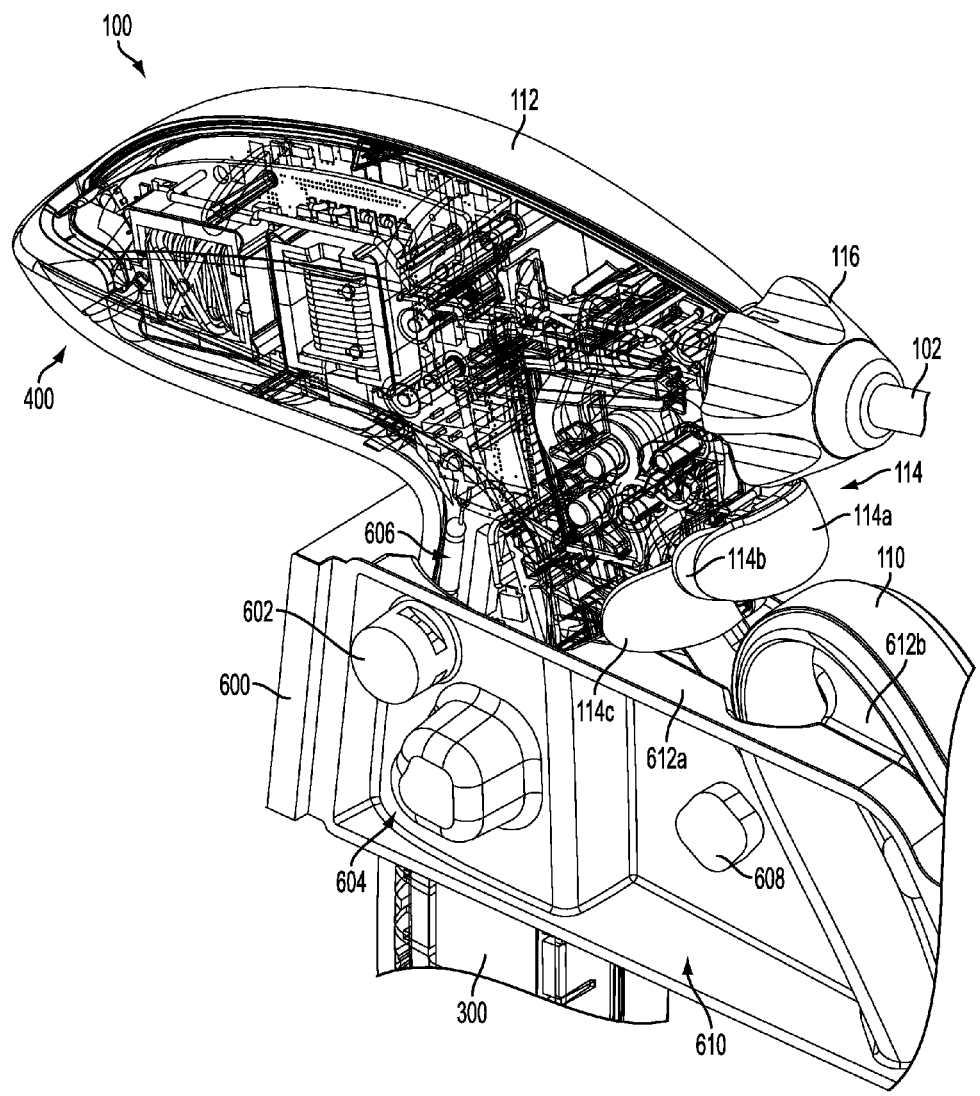
FIG. 8 is another view of the electrosurgical medical instrument comprising an initialization clip as shown in FIG. 7, according to one embodiment.
Figure 41:
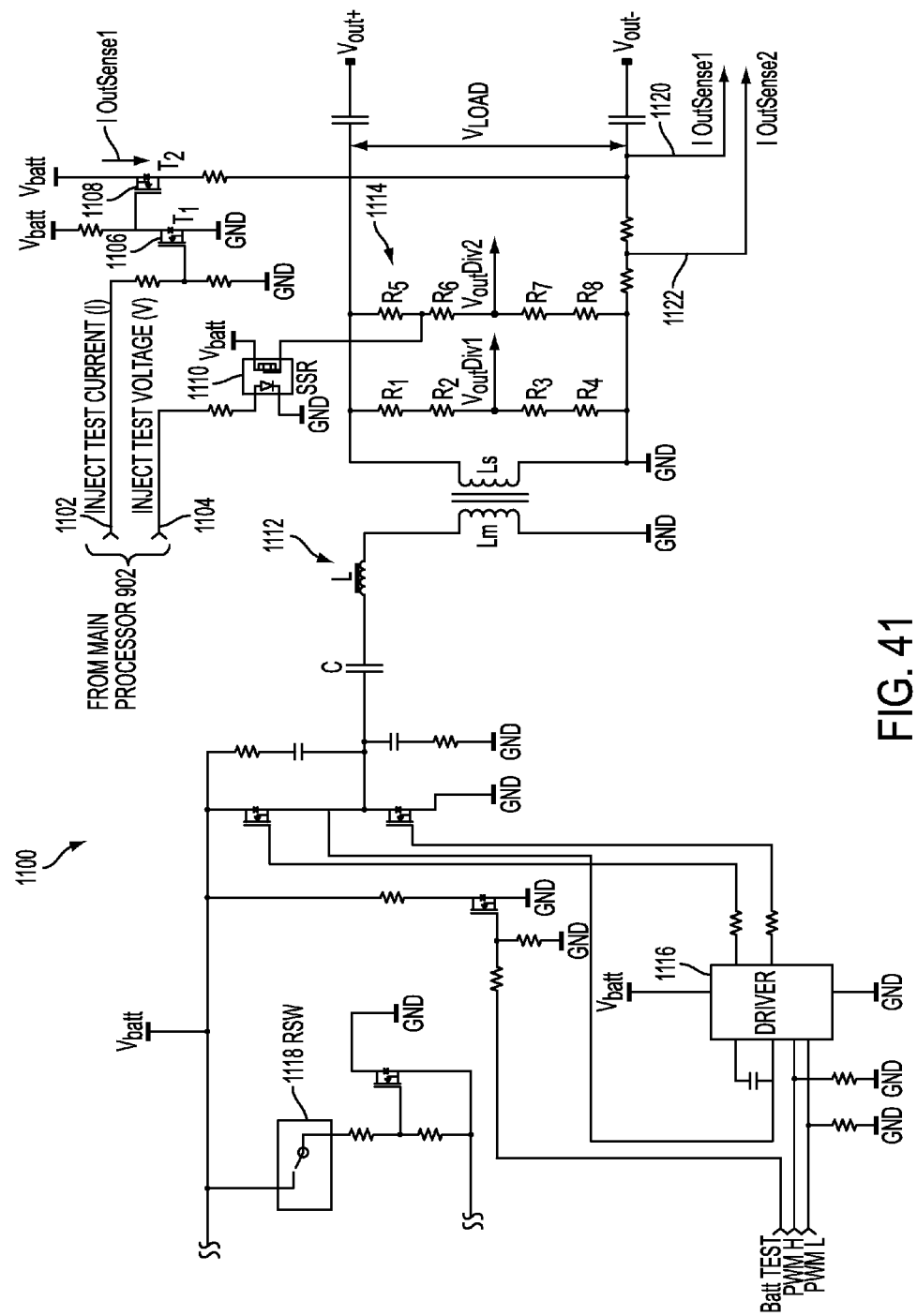
FIG. 41 illustrates a RF amplifier section with an output sensing test circuit and magnetic switch element, according to one embodiment.

In yet another embodiment, a remotely activated switch element 606 (such as a reed relay, Hall-effect sensor, RF device, optical element, for example, see FIGS. 8, 10, 41) that disables the electronics system 400 when a remote switch activation element 602 (such as, for example, a magnet as shown in FIG. 8, RF device, optical element) is brought into proximity to the magnetically operated element 606. This particular embodiment is described in more detail hereinbelow in connection with FIGS. 8, 10, 41, and 42-47, for example.

Also shown in FIG. 7 is the activation button 114 in multiple positions. In one embodiment, the activation button 114 is movable over multiple actuation positions to control multiple functions. In the embodiment illustrated in FIG. 7, the activation button 114 is shown in three separate positions 114a, 114b, 114c, where in a first position 114a the activation button 114 is full extended distally outwardly and does not result in energizing the RF energy circuit. In a second position 114b the activation button 114 is in a partial depression mode and in a third position 114c the activation button 114 is in a full depression mode. During normal operation, e.g., when the clip 600 is removed, when the activation button is in the first position 114a, the lockout mechanism is engaged and the operation of the control lever 110 is inhibited as previously described in connection with FIGS. 4-6 and the energy source 300 (FIG. 4) is disconnected from the electronics system 400 (FIG. 4). When the activation switch 114 is partially depressed in the second position 114b, the device is still mechanically locked out to inhibit the operation of the control lever 110, as previously described in connection with FIGS. 4-6, but the circuit is connected to the energy source 300 and becomes partially functional. For example, in one embodiment, several logic functions may be enabled while keeping the RF energy activation circuit disabled. When the activation switch 114 is fully depressed in the third position 114c, the device is mechanically unlocked and enables the operation of the control lever 110, as previously described in connection with FIGS. 4-6, but the circuit is connected to the energy source 300 and becomes fully functional, including enabling the operation of the logic and the RF energy circuit. It will be appreciated, however, that in the configuration of the instrument 100 shown in FIG. 7, the clip 600 mechanically prevents the operation of the control lever 110 and also inhibits the operation of the electronics system 400 by electrically disconnecting the energy source 300 from the electronics system 400. The functionality of the multi-position activation button 114 as it relates to the mechanical and electrical lockout will be described in more detail hereinbelow.

FIG. 8 is another view of the electrosurgical medical instrument 100 comprising an initialization clip 600 as shown in FIG. 7, according to one embodiment. In FIG. 7, the clip 600 is shown without a cover plate to show the internal structure of the clip 600. As shown in FIG. 8, the clip 600 defines an internal cavity that contains a magnet 602. The magnetic flux generated by the magnet 602 acts on a magnetically operated element 606 located on the electronics system 400. The magnetically operated element 606 is coupled to the electronics system 400 and the energy source 300 and acts as a switch to disconnect and connect the energy source to the electronics system 400.

In the embodiment illustrated in FIG. 8, the magnetic flux generated by the magnet 602 causes the magnetically operated element 606 to electrically disconnect the energy source 300 from the electronics system 400, including a transformer 404 and an inductor 406. When the magnet 602 is removed, by removing the clip 600 from the instrument 100, for example, the magnetically operated element 606 electrically connects the energy source 300 to the electronics system 400. Accordingly, as long as the clip 600 with the magnet 602 is located on the instrument 100, the instrument 100 is mechanically and electrically locked out. As previously described, when the clip 600 is located on the instrument 100, depressing the 114 in the first position 114a, second position 114b, or third position 114c does not activate the electronics system 400 because the magnetically operated element 606 electrically disconnects or decouples the energy source 300 from the electronics system 400. In one embodiment, the magnetically operated element 606 may be a reed switch, a hall-effect sensor, or any other switch type device that can be activated by a magnetic field. Still, in another embodiment, the medical instrument 100 may comprise an accelerometer to detect motion. When the accelerometer is at rest, indicating that the medical instrument 100 is at rest, the instrument 100 is completely powered down by disconnecting the battery 300 from the electronics system 400. When the accelerometer detects motion, indicating that the medical instrument 100 is no longer at rest, the instrument is powered up by connecting the battery 300 to the electronic system 400.

While undergoing sterilization, the electronics system 400 will not be powered and will draw only a leakage current of about 1 μA. The electronics system 400 may be disabled by the magnetically operated element 606 (e.g., a reed switch) and magnet 602 which is encased in the clip 600. The clip 600 is fitted to the medical instrument 100 as part of the manufacturing process, and must be removed to enable power from the battery 300. When powered, in the idle condition the load circuit draws an average of 10 mA, with peaks of up to 65 mA. When the activation button 114 is pressed, the device draws an average of 5 A, with peaks of 15.5 A from the battery 300. When packaged, the jaws are closed and there is no material between them. In one non-limiting embodiment, the voltage generated across the jaws is a maximum of 85V rms. This arrangement means there are two methods for preventing the generation of high voltages or currents—the magnetic clip 600 is the primary disabling mechanism, and the activation button 114 is the second. Several connection options for the battery 300 are described hereinbelow with reference to FIGS. 42-47.

Mechanical fastening elements 604 and 608 are used to hold the clip 600 coupled to the medical instrument 100. In the embodiment illustrated in FIG. 8, the clip comprises a first half 612a and a second 612b that can be fastened using mechanical fastening elements to form an interference fit, press fit, or friction fit, such that friction holds the two halves 612a, b after they are pushed or compressed together. In other embodiments, other fastening techniques may be employed to fasten the two halves 612a, b such as by ultrasonic welding, snap fitting, gluing, screwing, riveting, among others. Another embodiment of an initialization clip 650 is described below in connection with FIGS. 20 and 21.

Figure 9:
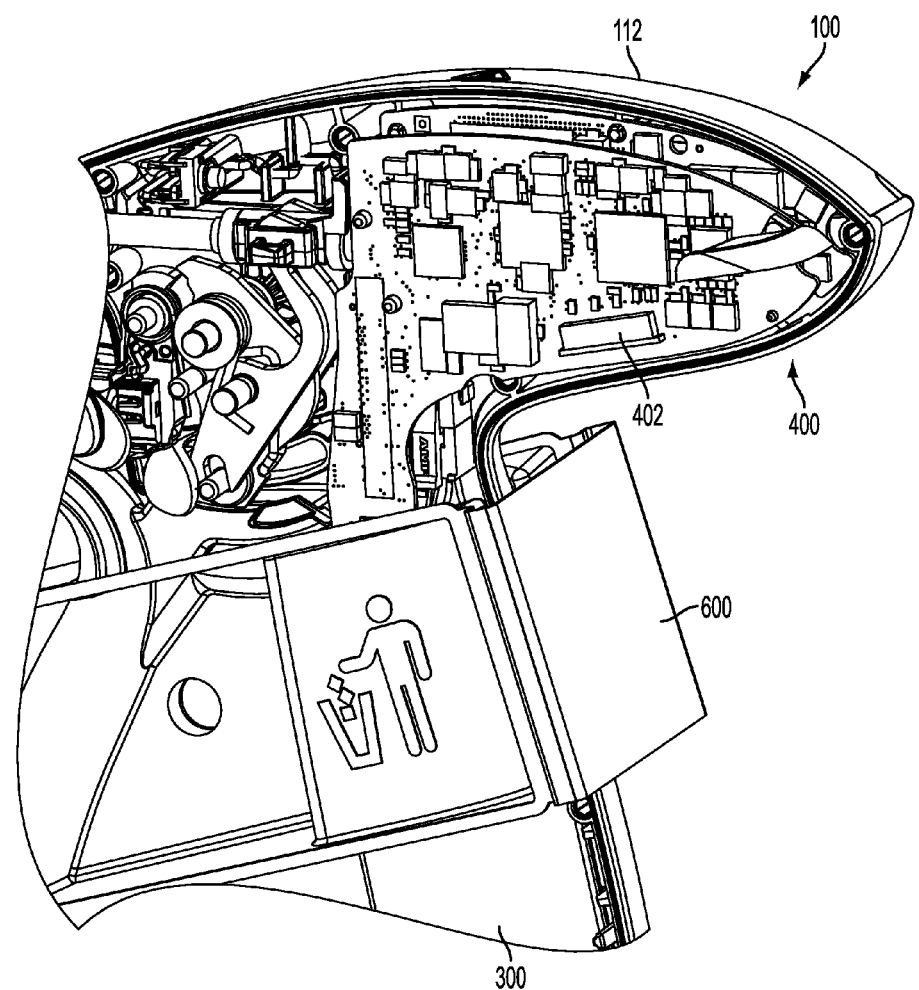
FIG. 9 illustrates a sectional view of a housing portion of an electrosurgical medical instrument showing an electronic circuit device portion of an electronics system, according to one embodiment.

FIG. 9 illustrates a sectional view of the housing 112 portion of the electrosurgical medical instrument 100 showing an electronic circuit device 402 portion of the electronics system 400, according to one embodiment. In one embodiment, the electronic circuit device 402 can be configured as a data gathering/programming interface, for example. In one embodiment, the electronic circuit device 402 can be programmed by a programming device (not shown). The electronic circuit device 402 can output real-time data such as tissue voltage, current, and impedance to an external data recording device (not shown). In one embodiment, the electronic circuit device 402 is a non-volatile memory device that can store computer program instructions and/or tissue voltage, current, and impedance data.

In one embodiment, the data transfer/device programming function can be implemented by a connector provided on the housing 112 to couple an external data transfer/device programmer device to the electronic circuit device 402. The external data transfer/device programmer device may be employed for two-way communication with the electronic circuit device 402. To upload a new program to the medical instrument 100, for example, the external data transfer/device programmer device can be plugged into the connector to couple to the electronic circuit device 402 and then upload the program. Data stored in the electronic circuit device 402 could be read just as easily via the connector. The data may include, for example, voltage (V), current (I), impedance (Z), device parameters, among others, without limitation.

In one embodiment, the data transfer/device programming function can be implemented via at least one of the LED 118a, b interfaces. For example, either through the tri-color LEDs 118a, b or the addition of an infrared (IR) LED (not shown), an optical data interface can be implemented. The optical data interface can be employed to transfer data to and from the instrument 100 and/or program the instrument 100. In one embodiment, a separate hood (not shown) comprising a cavity to receive the proximal end of the housing 112 comprising the LEDs 118a, b may be provided. The hood also comprises optical elements (e.g., IR LEDs) configured for optical communication in order to communicate via the optical interface comprised of LEDs 118a, b. In operation, the hood may be slidably inserted over the proximal end of the housing 112 such that the LEDs 118a, b are optically aligned with the optical elements located inside the hood.

FIGS. 10 and 11 illustrate the electrosurgical medical instrument 100 without the housing 112 portion to reveal the internal components of the instrument 100, according to one embodiment. The electronics system 400 comprises both digital and RF analog circuit elements. Accordingly, as shown in FIG. 11, two separate substrates 408a and 408b are provided where the digital circuit elements are located on a first substrate 408a and the RF amplifier section and other analog circuit elements are located on a second substrate 408b. The first and second substrates 408a, b are interconnected by a interconnect device 412. Still in FIG. 11, the first substrate 408a also includes digital circuit components including, for example, the electronic circuit device 402 for storing program and tissue information. The first substrate 408a also includes an audio feedback element 410. In one embodiment, the audio feedback element 410 is a piezo device. In other embodiments, however, different types of audio feedback devices may be employed without limitation. It will be appreciated that in various embodiments, the first and second substrates 408a, b are formed of printed circuit boards. In other embodiments, however, these substrates can be formed of any suitable materials, such as alumina ceramics, for example. The substrates 408a, b may comprise discrete, integrated, and/or hybrid circuit elements and combinations thereof. With reference now to FIG. 10, the second electronic substrate 408b comprises an inductor 404 and a transformer 406 that form a part of the RF energy circuit. With reference now to the embodiments disclosed in FIGS. 10 and 11, also shown are the dual tri-color LEDs 118a, b. Also shown is the electrical contact system 700 that couple RF energy produced by the RF energy circuits on the second substrate 408b to the medical forceps 108 (FIGS. 1 and 2). An electrical conductor 702 is coupled to the electrical contact system 700. The other end of the electrical conductor 702 is coupled to the RF energy circuit.

Figure 12:
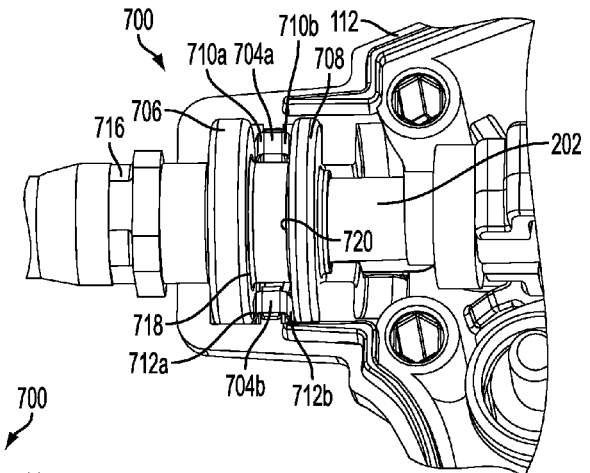
FIG. 12 illustrates a partial cutaway view of a housing to show an electrical contact system, according to one embodiment.
Figure 13:
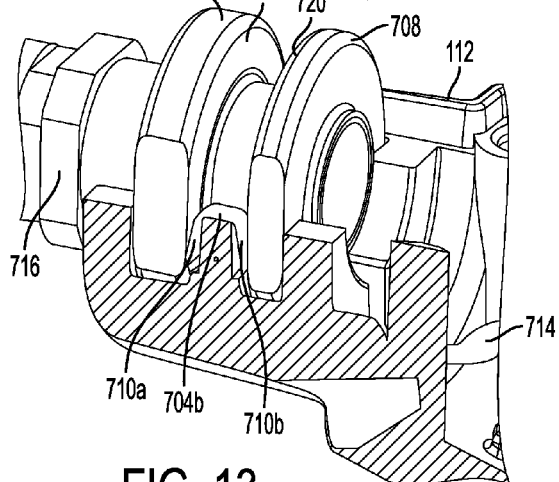
FIG. 13 illustrates a partial cutaway view of a housing to show an electrical contact system and an inner sheath removed, according to one embodiment.
Figure 14:
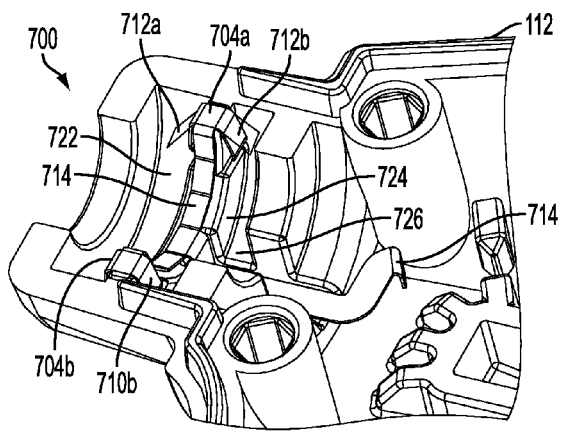
FIG. 14 illustrates a partial cutaway view of a housing with an electrically conductive shaft removed to show an electrical contact element, according to one embodiment.

FIGS. 12-14 illustrate various views of the electrical contact system 700, according to one embodiment. FIG. 12 illustrates a partial cutaway view of the housing 112 to show the electrical contact system 700, according to one embodiment. The electrical contact system 700 comprises an electrically conductive shaft 716 that is rotatable over 360° and comprises first and second rotatable electrodes 706, 708. The rotatable electrodes 706, 708 are electrically coupled to corresponding first and second electrical contact elements 704a, 704b where the electrical contact elements 704a, b are electrically coupled to the electrical conductor 702 (FIGS. 10-11) coupled to the RF energy circuit. Each the first and second electrical contact elements 704a, 704b comprise first and second electrical contact points 710a, 710b and 712a, 712b. The electrical contact points 710a and 712a are electrically coupled to a side wall 718 of the first rotatable electrode 706 and the electrical contact points 710b and 712b are electrically coupled to a side wall 720 of the second rotatable electrode 708. In one embodiment, the two electrical contact elements 704a, b provide four contact points 710a, 712a, 710b, 712b for redundancy. The electrical contact elements 704a, b and corresponding four contact points 710a, 712a, 710b, 712b allow the rotatable electrodes 706, 708 of the electrically conductive shaft 716 to rotate over 360°. The two electrical contact elements 704a, b may be formed of any suitable electrically conductive element such as copper, aluminum, gold, silver, iron, and any alloy including at least one of these element, without limitation. In one embodiment, the two electrical contact elements 704a, b are formed of beryllium copper (BeCu) and are gold plated for corrosion resistance and good electrical contact properties. In FIG. 12 the inner sheath 202 is shown slidably inserted within the electrically conductive shaft 716.

FIG. 13 illustrates a partial cutaway view of the housing 112 to show the electrical contact system 700 and the inner sheath 202 removed, according to one embodiment. FIG. 13, also shows an electrical element 714 that is electrically coupled to the electrical conductor 702 (FIGS. 10-11) coupled to the RF energy circuit. The electrical element 714 is coupled to the electrical contact elements 704a, b. Accordingly, the RF energy circuit is coupled to the electrical contact element 704a, b.

FIG. 14 illustrates a partial cutaway view of the housing 112 with the electrically conductive shaft 716 removed to show the electrical contact element 714, according to one embodiment. As shown in FIG. 14, the electrical contact element 714 is located in a partial circular wall 724 that separates the circular cavities 722, 726 configured to rotatably receive the respective rotatable electrodes 706, 708 (FIGS. 12-13). The electrical contact element 714 is electrically coupled to the two electrical contact elements 704a, b. As shown, the two electrical contact elements 704a, b are located on top of the electrical contact element 714.

Figure 15:
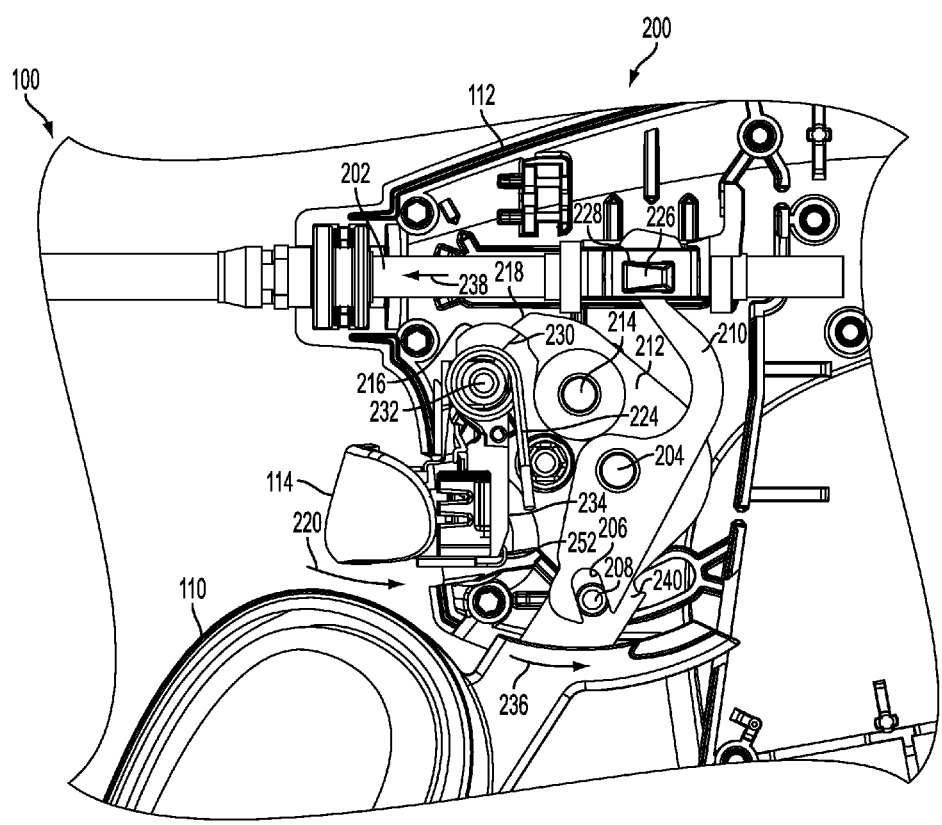
FIG. 15 illustrates a partial sectional view of the electrosurgical medical instrument in a locked position, according to one embodiment.

FIG. 15 illustrates a partial sectional view of the electrosurgical medical instrument 100 in a locked position, according to one embodiment. FIG. 15 illustrates the electrosurgical medical instrument 100 in a locked out position to prevent the actuation of the control lever 110, according to one embodiment. The control lever 110 comprises a trigger lever 212 portion that is configured to rotate about a trigger pivot 214 when the control lever 110 is squeezed in the direction of arrow 122 (FIG. 4), unless the instrument is in locked out mode.

In the locked out mode, the trigger lever 212 portion of the control lever 110 is prevented from rotating about the trigger pivot 214 because a projection 218 of the trigger lever 212 engages a top surface 216 of an activation button lever 234 that rotates about activation button pivot 232 when the activation button 114 is squeezed in the direction of arrow 220. A contact button torsion spring 224 keeps the activation button 114 in an outwardly position to disable the electrosurgical energy from being applied while simultaneously engaging the projection 218 of the trigger lever 212 with the top surface 216 to lockout the instrument 100 until the activation button 114 is fully engaged in the direction of arrow 220.

A second trigger lever 210 comprises a first end that defines a pin slot 206 and a second end that defines a tab 226. The pin slot 206 engages a pin 208 portion of the trigger lever 212. As the trigger lever 212 rotates in the direction of arrow 236 about trigger pivot 214 the pin 208 moves within the pin slot 206 to apply a rotation movement to the second trigger lever 210. The tab 226 engages an aperture 228 to mechanically couple the second lever to the inner sheath 202. Thus, as the trigger lever 212 moves in the direction of arrow 236, the second trigger lever 210 rotates about lever pivot 204 to apply a linear translation motion to the inner sheath 202 in the direction of arrow 238. A trigger torsion spring 222 engages the second trigger lever 210 at a notch 240 formed on the second trigger lever 210. The trigger torsion spring 222 torque balances the hand force applied to the second trigger lever 210 through the control lever 110 about the trigger pivot 214.

Figure 16:
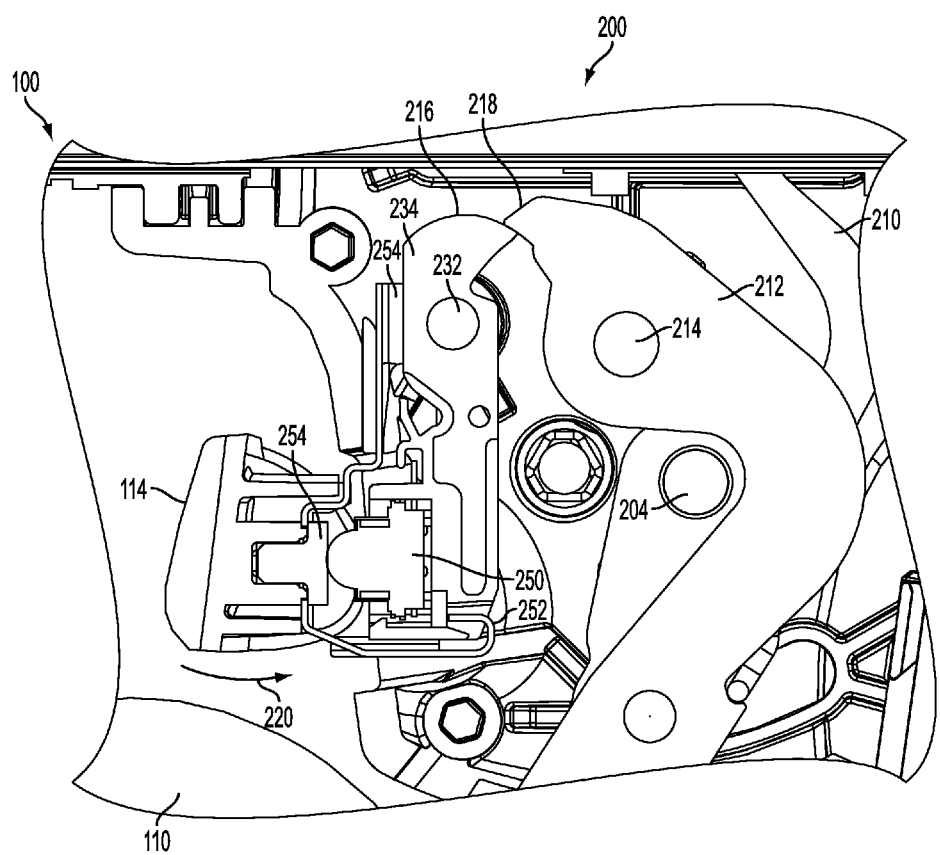
FIG. 16 illustrates another partial sectional view of the electrosurgical medical instrument in a locked position, according to one embodiment.

FIG. 16 illustrates another partial sectional view of the electrosurgical medical instrument 100 in a locked position, according to one embodiment. In the locked position, the knife lockout mechanism 200 prevents the control lever 110 from rotating about the trigger pivot 214 when the projection 218 of the trigger lever 212 engages a top surface 216 of the activation button lever 234. The activation button lever 234 rotates about the activation button pivot 232 when the activation button 114 is squeezed or depressed in the direction of arrow 220. The activation button 114 is supported independently from the activation button pivot 232 by a mechanism 254 such that the activation button 114 is independently operable from the actuation of the control lever 110 actuate the cutting blade (knife). Thus, the activation button 114 can be depressed to energize the instrument 100 without actuating the cutting blade (knife). When the activation button 114 is squeezed or depressed in the direction of arrow 220, the activation button 114 actuates a switch 250, which enables energy actuation of the instrument 100. Thus, electrosurgical RF energy is applied through jaw members of the electrosurgical forceps, otherwise referred to as clamp arms of the instrument 100. The cutting blade, however, is still locked out by the knife lockout mechanism 200. A tang 252 prevents the activation button 114 from being removed by pulling forward on it.

Figure 17:
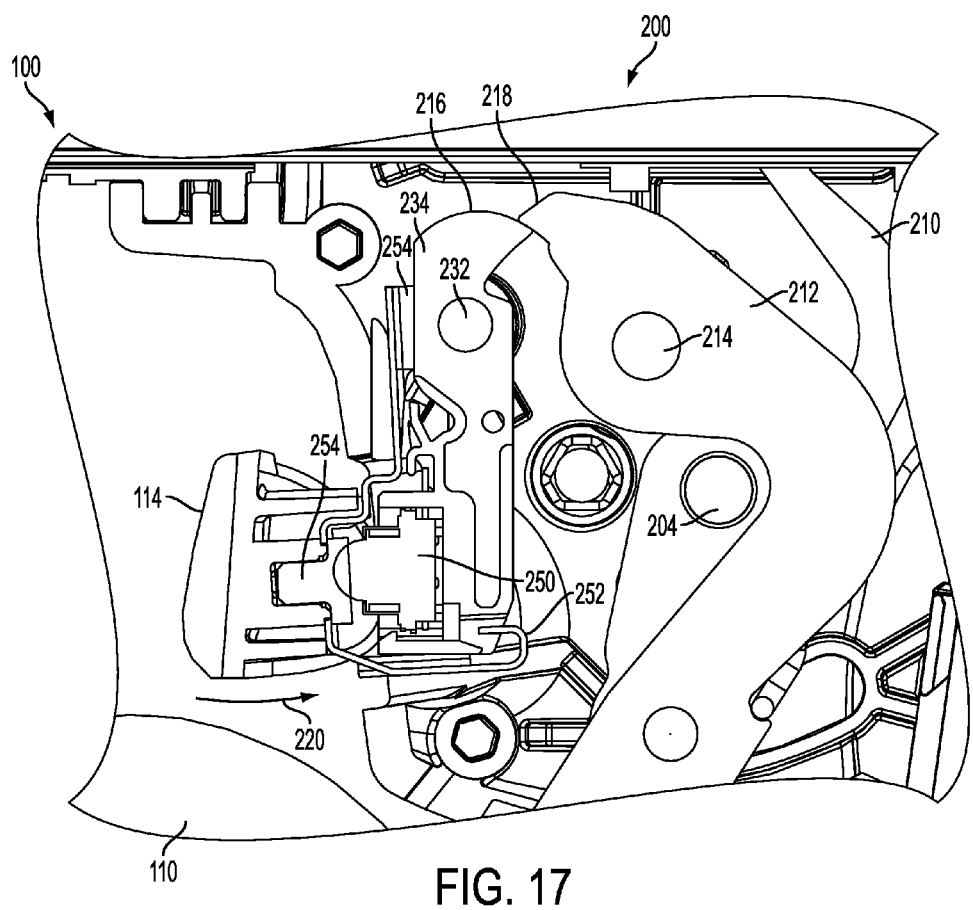
FIG. 17 illustrates another partial sectional view of the electrosurgical medical instrument with an activation button partially depressed to activate the energy circuit without releasing the knife lockout mechanism, according to one embodiment.

FIG. 17 illustrates another partial sectional view of the electrosurgical medical instrument 100 with the activation button 114 partially depressed to activate the energy circuit without releasing the knife lockout mechanism 200, according to one embodiment. Although the activation button 114 is partially depressed to actuate the switch 250 and energize the instrument 100, but the knife lockout mechanism 200 is still engaged to prevent the knife from being actuated by the control lever 110. As shown, the projection 218 of the trigger lever 212 is still engaged with the top surface 216 of the activation button lever 234 to prevent the trigger lever 212 from rotating about the trigger pivot 214 when the control lever 110 is squeezed.

Figure 18:
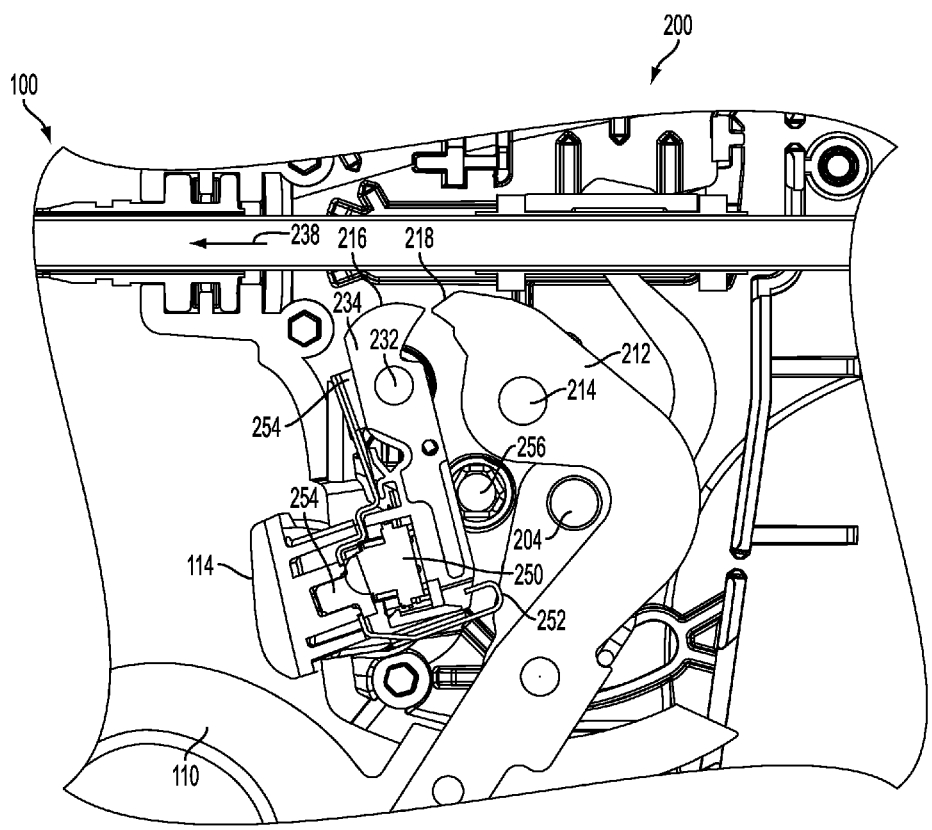
FIG. 18 illustrates another partial sectional view of the electrosurgical instrument with the activation button fully depressed to activate the energy circuit and release the knife lockout mechanism, according to one embodiment.

FIG. 18 illustrates another partial sectional view of the electrosurgical instrument 100 with the activation button 114 fully depressed to activate the energy circuit and release the knife lockout mechanism 200, according to one embodiment. The activation button 114 is fully depressed to actuate the switch 250 and energize the instrument 100 and also releasing the knife lockout mechanism 200. In the fully depressed mode, the activation button 114 rests on a pin 256. As shown, the projection 218 of the trigger lever 212 is disengaged from the top surface 216 of the activation button lever 234 that rotates about activation button pivot 232 to enable the trigger lever 212 to rotate about the trigger pivot 214 when the control lever 110 is squeezed to throw the knife. As shown, the inner sheath 202 can now be advanced in the direction indicated by the direction of arrow 238.

Figure 19:
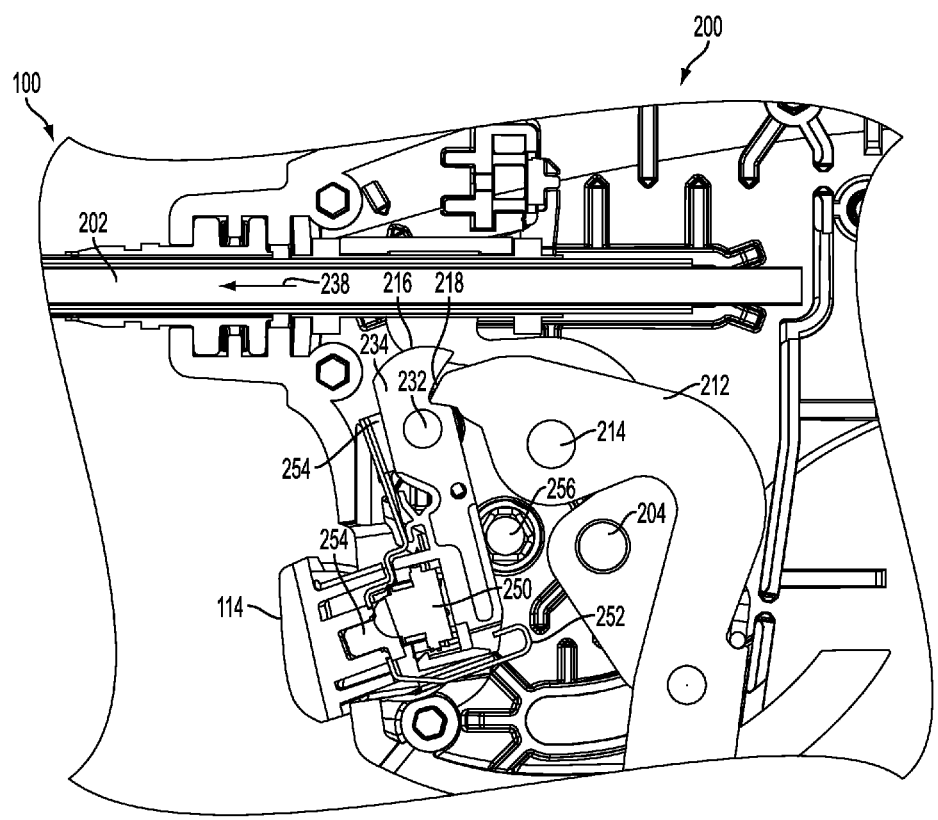
FIG. 19 illustrates another partial sectional view of the electrosurgical medical instrument with the activation button fully depressed to activate the energy circuit with the knife lockout mechanism released and the knife fully thrown, according to one embodiment.

FIG. 19 illustrates another partial sectional view of the electrosurgical medical instrument 100 with the activation button 114 fully depressed to activate the energy circuit with the knife lockout mechanism 200 released and the knife fully thrown, according to one embodiment. As shown, the inner sheath 202 has advanced in the direction indicated by the direction of arrow 238.

Figure 21:
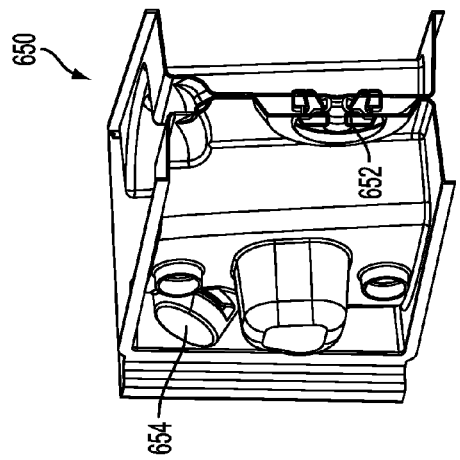
FIG. 21 is a partial cutaway view of the initialization clip shown in FIG. 20, according to one embodiment.
Figure 20:
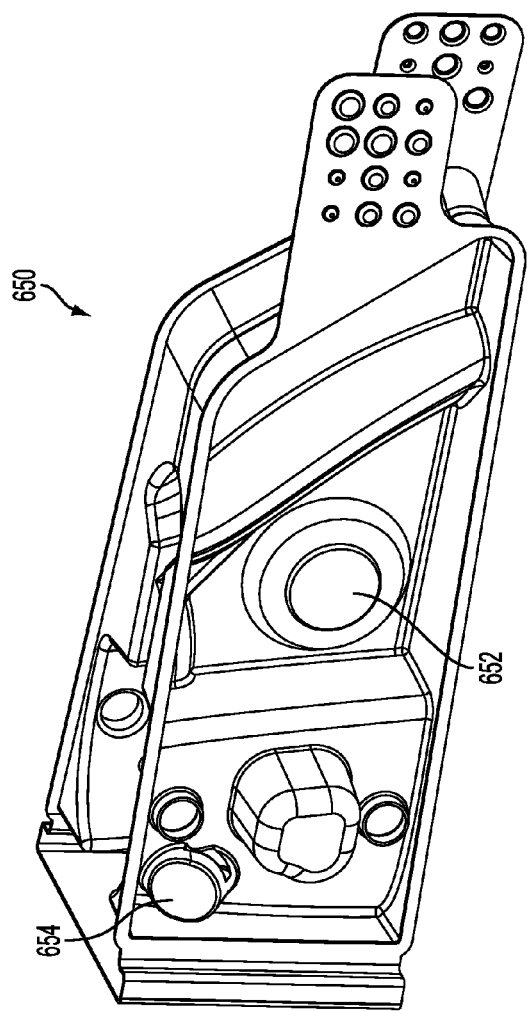
FIG. 20 is a perspective view of an initialization clip, according to one embodiment.

FIG. 20 is a perspective view of an initialization clip 650, according to one embodiment. The initialization clip 650 is similar to the initialization clip 600 described in connection with FIGS. 7-9. FIG. 21 is partial cutaway view of the initialization clip 650 shown in FIG. 20, according to one embodiment. With reference to FIGS. 20 and 21, the initialization clip 650 is attached to the electrosurgical medical instrument 100 to prevent firing the medical instrument 100 without enabling and also provides some protection during shipment. The initialization clip 650 is applied to the instrument 100 after initialization at the factory and stays on the instrument 100 during storage. Upon removal of the clip 650, the instrument 100 activates in the manner described with respect to the initialization clip 600 of FIGS. 6-9. In one embodiment, if the instrument 100 has completed one full energy activation cycle (described in more detail hereinbelow) and the clip 650 is re-installed, the instrument 100 will not function upon removal of the clip 650 a second time. The initialization clip 650 comprises a snap button 652 to secure the clip 650 to the instrument 100 and a tilted magnetic pocket 654. The magnetic pocket 654 contains a magnet that works in conjunction with a reed switch, or other suitable sensing element, to detect the presence of the initialization clip 650, and thus determine whether it is attached or removed from the instrument 100. In other respects, the initialization clip 650 operates similarly to the initialization clip 600 described in connection with FIGS. 7-9.

The description now turns to the RF drive and control circuitry sections of the battery powered electrosurgical instrument 100, according to one embodiment. As described in FIGS. 10-11, the RF drive and control circuitry sections of the electronics system 400 are located on a second substrate 408b. The electronics elements of the power supply and RF amplifier sections should be designed to have the highest efficiency possible in order to minimize the heat rejected into the relatively small handheld housing 112. Efficiency also provides the longest storage and operational battery life possible. As described in the embodiments illustrated in FIGS. 23-35, litz wire may be wound around a bobbin core to reduce AC losses due to high frequency RF. The litz wire construction provides greater efficiency and thus also prevents heat generation in the device.

In various embodiments, efficiency of the power supply and RF drive and control circuitry sections also may minimize the size of the battery 300 required to fulfill the mission life, or to extend the mission life for a given size battery 300. In one embodiment, the battery 300 provides a low source impedance at a terminal voltage of 12.6V (unloaded) and a 1030 mA-Hour capacity. Under load, the battery voltage is a nominal 11.1V, for example.

Radio frequency drive amplifier topologies may vary according to various embodiments. In one embodiment, for example, a series resonant approach may be employed where the operating frequency is varied to change the output voltage to force the medical instrument 100 to operate according to a pre-programmed load curve. In a series resonant approach, the impedance of a series resonant network is at a minimum at the resonant frequency, because the reactance of the capacitive and inductive elements cancel, leaving a small real resistance. The voltage maximum for a series resonant circuit also occurs at the resonant frequency (and also depends upon the circuit Q). Accordingly, to produce a high voltage on the output, the series resonant circuit should operate closer to the resonant frequency, which increases the current draw from the DC supply (e.g., battery 300) to feed the RF amplifier section with the required current. Although the series resonant approach may be referred to as a resonant mode boost converter, in reality, the design is rarely operated at the resonant frequency, because that is the point of maximum voltage. The benefit of a resonant mode topology is that if it is operated very close to the resonant frequency, the switching field effect transistors (FETs) can be switched "ON" or "OFF" at either a voltage or current zero crossing, which dissipates the least amount of power in the switching FETs as is possible.

Another feature of the RF drive and control circuitry section according to one embodiment, provides a relatively high turns ratio transformer which steps up the output voltage to about 85 VRMS from the nominal battery 300 voltage of about 11.1V. This provides a more compact implementation because only one transformer and one other inductor are required. In such a circuit, high currents are necessary on the transformer primary to create the desired output voltage or current. Such device, however, cannot be operated at the resonant frequency because allowances are made to take into account for the battery voltage dropping as it is expended. Accordingly, some headroom is provided to maintain the output voltage at the required level. A more detailed description of a series resonant approach is provided in commonly assigned international PCT Patent Application No. PCT/GB2011/000778, titled "Medical Device," filed May 20, 2011, the disclosure of which is incorporated herein by reference in its entirety.

According to another embodiment, an RF instrument topology comprising a novel and unique architecture is provided for a handheld battery powered RF based generator for the electrosurgical medical instrument 100. Accordingly, in one embodiment, the present disclosure provides an RF instrument topology with an architecture configured such that each power section of the device operate at maximum efficiency regardless of the load resistance presented by the tissue or what voltage, current, or power level is commanded by the controller. In one embodiment, this may be implemented by employing the most efficient modalities of energy transformation presently known and by minimizing the component size to provide a small and light weight electronics package to fit within the housing 112, for example.

In one embodiment, the RF power electronics section of the electronics system 400 may be partitioned as a boost mode converter, synchronous buck converter, and a parallel resonant amplifier. According to one embodiment, a resonant mode boost converter section of the medical instrument 100 may be employed to convert the DC battery 300 voltage to a higher DC voltage for use by the synchronous mode buck converter. One aspect to consider for achieving a predetermined efficiency of the resonant mode boost converter section is ratio between input and output voltages of the boost converter. In one embodiment, although a 10:1 ratio is achievable, the cost is that for any appreciable power on the secondary the input currents to the boost mode transformer become quite heavy, in the range of about 15-25 A, depending on the load.

In another embodiment a transformer turns ratio of about 5:1 is provided. It will be appreciated that transformer ratios in the range of about 5:1 to about 10:1 also may be implemented, without limitation. In a 5:1 transformer turns ratio, the design tradeoff is managing the Q of the parallel resonant output against the boost ratio. The resonant output network performs two functions. First, it filters the square, digital pulses from the Class D output amplifier and removes all but the fundamental frequency sine wave from the output. Second, it provides a passive voltage gain due to the Q of the filter network. In other words, current from the amplifier is turned into output voltage, at a gain determined by the circuit's unloaded Q and the load resistance, which affects the Q of the circuit.

Another aspect to consider for achieving a predetermined efficiency in the resonant mode boost converter section is to utilize a full bridge switcher topology, which allows half the turns ratio for the boost transformer for the same input voltage. The tradeoff is that this approach may require additional FET transistors, e.g., an additional two FETs are required over a half bridge approach, for example. Presently available switchmode FETs, however, are relatively small, and while the gate drive power is not negligible, it provides a reasonable design tradeoff.

Yet another aspect to consider for achieving a predetermined efficiency in the resonant mode boost converter section and operating the boost converter at maximum efficiency, is to always run the circuit at the resonant frequency so that the FETs are always switching at either a voltage or current minima, whichever is selected by the designer (ZCS vs. ZVS switching), for example. This can include monitoring the resonant frequency of the converter as the load changes, and making adjustments to the switching frequency of the boost converter to allow ZVS or ZCS (Zero Voltage Switching/Zero Current Switching) to occur for minimum power dissipation.

Yet another aspect to consider for achieving a predetermined efficiency in the resonant mode boost converter section is to utilize a synchronous rectifier circuit instead of a conventional full-wave diode rectifier block. Synchronous rectification employs FETs as diodes because the on-resistance of the FET is so much lower than that of even a Schottky power diode optimized for low forward voltage drop under high current conditions. A synchronous rectifier requires gate drive for the FETs and the logic to control them, but offers significant power savings over a traditional full bridge rectifier.

In accordance with various embodiments, the predetermined efficiency of a resonant mode boost converter is approximately 98-99% input to output, for example. Any suitable predetermined efficiency may be selected based on the particular implementation. Accordingly, the embodiments described herein are limited in this context.

According to one embodiment, a synchronous buck converter section of the medical instrument 100 may be employed to reduce the DC voltage fed to the RF amplifier section to the predetermined level to maintain the commanded output power, voltage or current as dictated by the load curve, with as little loss as is possible. The buck converter is essentially an LC lowpass filter fed by a low impedance switch, along with a regulation circuit to control the switch to maintain the commanded output voltage. The operating voltage is dropped to the predetermined level commanded by the main controller, which is running the control system code to force the system to follow the assigned load curve as a function of sensed tissue resistance. In accordance with various embodiments, the predetermined efficiency of a synchronous buck regulator is approximately 99%, for example. Any suitable predetermined efficiency may be selected based on the particular implementation. Accordingly, the embodiments described herein are limited in this context.

According to one embodiment, a resonant mode RF amplifier section comprising a parallel resonant network on the RF amplifier section output is provided. In one embodiment, a predetermined efficiency may be achieved by a providing a parallel resonant network on the RF amplifier section output. The RF amplifier section may be driven at the resonant frequency of the output network which accomplished three things. First, the high Q network allows some passive voltage gain on the output, reducing the boost required from the boost regulator in order to produce high voltage output levels. Second, the square pulses produced by the RF amplifier section are filtered and only the fundamental frequency is allowed to pass to the output. Third, a full-bridge amplifier is switched at the resonant frequency of the output filter, which is to say at either the voltage zero crossings or the current zero crossings in order to dissipate minimum power. Accordingly, a predetermined efficiency of the RF amplifier section is approximately 98%. Gate drive losses may limit the efficiency to this figure or slightly lower. Any suitable predetermined efficiency may be selected based on the particular implementation. Accordingly, the embodiments described herein are limited in this context.

In view of the RF instrument topology and architecture described above, an overall system efficiency of approximately 0.99*0.99*0.98, which is approximately 96%, may be achieved. Accordingly, to deliver approximately 45 W, approximately 1.8 W would be dissipated by the electronics exclusive of the power required to run the main and housekeeping microprocessors, and the support circuits such as the ADC and analog amplifiers and filters. To deliver approximately 135 W, approximately 5.4 W would be dissipated. This is the amount of power that would be required to implement a large jaw class generator in a hand held electrosurgical medical instrument. Overall system efficiency would likely only be a weak function of load resistance, instead of a relatively strong one as it may be the case in some conventional instruments.

In various other embodiments of the electrosurgical medical instrument 100, a series resonant topology may be employed to achieve certain predetermined efficiency increase by employing a full bridge amplifier for the primary circuit and isolate the full bridge amplifier from ground to get more voltage on the primary. This provides a larger primary inductance and lower flux density due to the larger number of turns on the primary.

Figure 22:
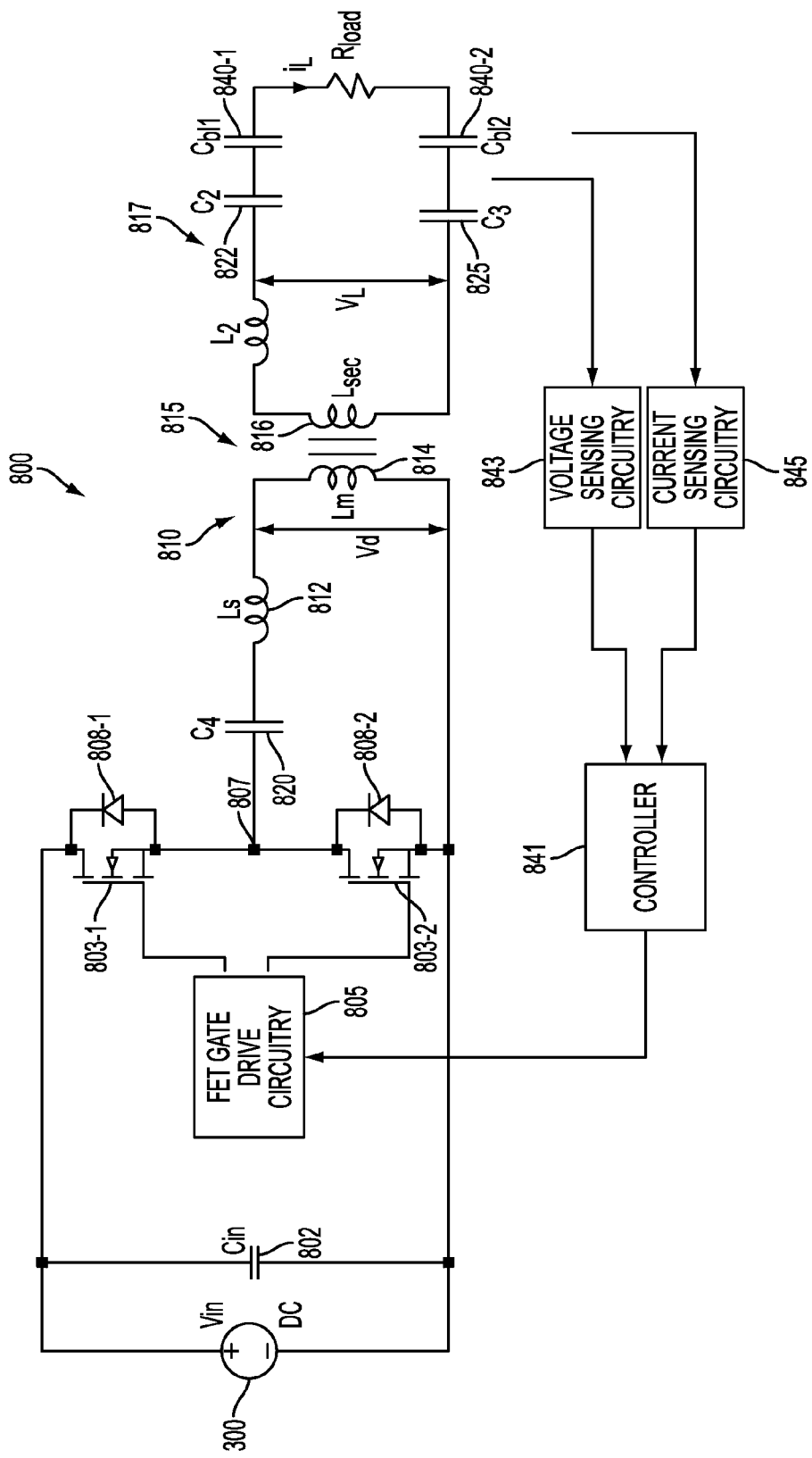
FIG. 22 illustrates an RF drive and control circuit, according to one embodiment.

FIG. 22 illustrates an RF drive and control circuit 800, according to one embodiment. FIG. 22 is a part schematic part block diagram illustrating the RF drive and control circuitry 800 used in this embodiment to generate and control the RF electrical energy supplied to the forceps 108. As will be explained in more detail below, in this embodiment, the drive circuitry 800 is a resonant mode RF amplifier comprising a parallel resonant network on the RF amplifier output and the control circuitry operates to control the operating frequency of the drive signal so that it is maintained at the resonant frequency of the drive circuit, which in turn controls the amount of power supplied to the forceps 108. The way that this is achieved will become apparent from the following description.

As shown in FIG. 22, the RF drive and control circuit 800 comprises the above described battery 300 are arranged to supply, in this example, about 0V and about 12V rails. An input capacitor ($C_{in}$) 802 is connected between the 0V and the 12V for providing a low source impedance. A pair of FET switches 803-1 and 803-2 (both of which are N-channel in this embodiment to reduce power losses) is connected in series between the 0V rail and the 12V rail. FET gate drive circuitry 805 is provided that generates two drive signals—one for driving each of the two FETs 803. The FET gate drive circuitry 805 generates drive signals that causes the upper FET (803-1) to be on when the lower FET (803-2) is off and vice versa. This causes the node 807 to be alternately connected to the 12V rail (when the FET 803-1 is switched on) and the 0V rail (when the FET 803-2 is switched on). FIG. 22 also shows the internal parasitic diodes 808-1 and 808-2 of the corresponding FETs 803, which conduct during any periods that the FETs 803 are open.

As shown in FIG. 22, the node 807 is connected to an inductor-inductor resonant circuit 810 formed by an inductor $L_s$ 812 and an inductor $L_m$ 814, which is the primary coil of a transformer 815. The transformer 815 is the schematic symbol for the transformer 404 shown in FIGS. 8 and 10 and described in more detail below in connection with FIGS. 23-35. Turning back to FIG. 22, the FET gate driving circuitry 805 is arranged to generate drive signals at a drive frequency ($f_d$) that opens and crosses the FET switches 803 at the resonant frequency of the parallel resonant circuit 810. As a result of the resonant characteristic of the resonant circuit 810, the square wave voltage at node 807 will cause a substantially sinusoidal current at the drive frequency ($f_d$) to flow within the resonant circuit 810. As illustrated in FIG. 22, the inductor $L_m$ 814 is the primary coil of a transformer 815, the secondary coil of which is formed by inductor $L_{sec}$ 816. The inductor $L_{sec}$ 816 of the transformer 815 secondary is connected to a resonant circuit 817 formed by inductor $L_2$, capacitor $C_4$ 820, capacitor $C_2$ 822, and capacitor $C_3$ 825. The transformer 815 up-converts the drive voltage ($V_d$) across the inductor $L_m$ 814 to the voltage that is applied to the output parallel resonant circuit 817. The load voltage ($V_L$) is output by the parallel resonant circuit 817 and is applied to the load (represented by the load resistance $R_{load}$ 819 in FIG. 22) corresponding to the impedance of the forceps' jaws and any tissue or vessel gripped by the forceps 108. As shown in FIG. 15, a pair of DC blocking capacitors $C_{b1}$ 840-1 and 840-2 is provided to prevent any DC signal being applied to the load 819.

In one embodiment, the transformer 815 may be implemented with a Core Diameter (mm), Wire Diameter (mm), and Gap between secondary windings in accordance with the following specifications:

Core Diameter, D (mm)

$$D=19.9\times 10^{-3}$$

Wire diameter, W (mm) for 22 AWG wire $$W=7.366\times 10^{-4}$$

Gap between secondary windings, in gap=0.125

$$G=gap/25.4$$

In this embodiment, the amount of electrical power supplied to the forceps 108 is controlled by varying the frequency of the switching signals used to switch the FETs 803. This works because the resonant circuit 810 acts as a frequency dependent (loss less) attenuator. The closer the drive signal is to the resonant frequency of the resonant circuit 810, the less the drive signal is attenuated. Similarly, as the frequency of the drive signal is moved away from the resonant frequency of the circuit 810, the more the drive signal is attenuated and so the power supplied to the load reduces. In this embodiment, the frequency of the switching signals generated by the FET gate drive circuitry 805 is controlled by a controller 841 based on a desired power to be delivered to the load 819 and measurements of the load voltage ($V_L$) and of the load current ($I_L$) obtained by conventional voltage sensing circuitry 843 and current sensing circuitry 845. The way that the controller 841 operates will be described in more detail below.

In one embodiment, the voltage sensing circuitry 843 and the current sensing circuitry 845 may be implemented with high bandwidth, high speed rail-to-rail amplifiers (e.g., LMH6643 by National Semiconductor). Such amplifiers, however, consume a relatively high current when they are operational. Accordingly, a power save circuit may be provided to reduce the supply voltage of the amplifiers when they are not being used in the voltage sensing circuitry 843 and the current sensing circuitry 845. In one-embodiment, a step-down regulator (e.g., LT3502 by Linear Technologies) may be employed by the power save circuit to reduce the supply voltage of the rail-to-rail amplifiers and thus extend the life of the battery 300.

In one embodiment, the transformer 815 and/or the inductor $L_s$ 812 may be implemented with a configuration of litz wire conductors to minimize the eddy-current effects in the windings of high-frequency inductive components. These effects include skin-effect losses and proximity effect losses. Both effects can be controlled by the use of litz wire, which are conductors made up of multiple individually insulated strands of wire twisted or woven together. Although the term litz wire is frequently reserved for conductors constructed according to a carefully prescribed pattern, in accordance with the present disclosure, any wire strands that are simply twisted or grouped together may be referred to as litz wire. Accordingly, as used herein, the term litz wire refers to any insulated twisted or grouped strands of wires.

By way of background, litz wire can reduce the severe eddy-current losses that otherwise limit the performance of high-frequency magnetic components, such as the transformer 815 and/or the inductor $L_s$ 812 used in the RF drive and control circuit 800 of FIG. 22. Although litz wire can be very expensive, certain design methodologies provide significant cost reduction without significant increases in loss, or more generally, enable the selection of a minimum loss design at any given cost. Losses in litz-wire transformer windings have been calculated by many authors, but relatively little work addresses the design problem of how to choose the number and diameter of strands for a particular application. Cost-constrained litz wire configurations are described in C. R. Sullivan, "Cost-Constrained Selection of Strand Wire and Number in a Litz-Wire Transformer Winding," *IEEE Transactions on Power Electronics*, vol. 16, no. 2, pp. 281-288, which is incorporated herein by reference. The choice of the degree of stranding in litz wire for a transformer winding is described in C. R. Sullivan, "Optimal Choice for Number of Strands in a Litz-Wire Transformer Winding," *IEEE Transactions on Power Electronics*, vol. 14, no. 2, pp. 283-291, which is incorporated herein by reference.

In one embodiment, the transformer 815 and/or the inductor $L_s$ 812 may be implemented with litz wire by HM Wire International, Inc., of Canton, Ohio or New England Wire Technologies of Lisbon, N.H., which has a slightly different construction in terms of the number of strands in the intermediate windings, but has the same total number of strands of either 44 gauge or 46 gauge wire by HM Wire International, Inc. Accordingly, the disclosure now turns to FIGS. 23-35, which illustrate one embodiment of the transformer 815 and the inductor $L_s$ 812 implemented with litz wire.

Figure 23:
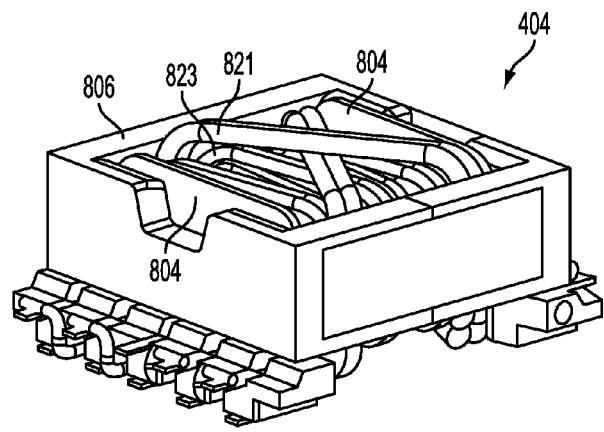
FIG. 23 illustrates a perspective view of one embodiment of a transformer employed in the RF drive circuit illustrated in FIG. 22.

FIG. 23 illustrates a perspective view of one embodiment of the transformer 404 shown in FIGS. 8 and 10 and shown as transformer 815 in connection with the RF drive circuit 800 illustrated in FIG. 22. As shown in FIG. 23, in one embodiment, the transformer 404 comprises a bobbin 804, a ferrite core 806, a primary coil 821 (e.g., inductor $L_m$ 814 in FIG. 22), and a secondary coil 823 (e.g., inductor $L_{sec}$ 816 in FIG. 22). In one embodiment, the bobbin 804 may be a 10-pin surface mounted device (SMD) provided by Ferroxcube International Holding B.V. In one embodiment, the ferrite core 806 may be an EFD 20/107 N49. In one embodiment, the transformer 815 has a power transfer of ~45 W, a maximum secondary current of ~1.5 A RMS, maximum secondary voltage of ~90V RMS, maximum primary current of ~15.5 A RMS, and a turns ratio of 20:2 (secondary turns:primary turns), for example. The operating frequency range of the transformer 404 is from ~370 kHz to ~550 kHz, and a preferred frequency of ~430 kHz. It will be appreciated that these specification are provided as examples and should not be construed to be limiting of the scope of the appended claims.

In one embodiment, the transformer 404 comprises a ferrite core material having particular characteristics. The core used for both the inductor 406 and the transformer 404, albeit with a different gap to yield the required $A_L$ for each component. $A_L$ has units of Henrys/turns$^2$, so the inductance of a winding may be found by using NTURNS$^2$*$A_L$. In one embodiment, an $A_L$ of 37 is used for the inductor 406, and an $A_L$ of 55 is used for the transformer 406. This corresponds to a gap of approximately 0.8 mm and 2.0 mm respectively, although the $A_L$ or the inductance is the parameter to which the manufacturing process controls, with the $A_L$ being an intermediate quantity that we are not measuring directly.

In one embodiment, the inductance of the inductor 406 and transformer 404 winding may be measured directly with "golden bobbins," which are squarely in the middle of the tolerance bands for the winding statistical distributions. Cores that are ground are then tested using the "golden bobbin" to assess whether the grind is good on the cores. Better results were yielded than the industry standard method, which is to fill a bobbin with as many windings as they can fit on the bobbin, and then back calculating the $A_L$ of the core, and controlling $A_L$ instead of the inductance. It was found that using a "golden bobbin" in the manufacturing process yielded better results. The bobbin is what the copper windings are secured to, and the ferrite E cores slip through a hole in the bobbin, and are secured with clips.

Figure 24:
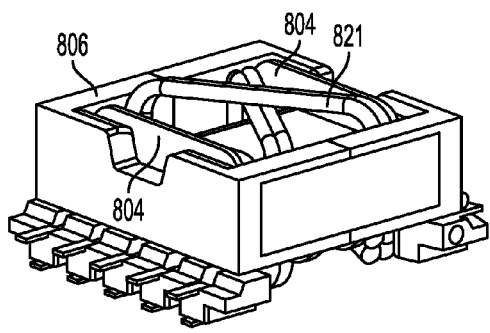
FIG. 24 illustrates a perspective view of one embodiment of a primary coil of the transformer illustrated in FIG. 23.

FIG. 24 illustrates a perspective view of one embodiment of the primary coil 821 (e.g., inductor $L_m$ 814 in FIG. 22) of the transformer 404 illustrated in FIG. 23. In one embodiment, the primary coil 821 windings may be constructed using 300 strand/46 gauge litz wire as indicated in TABLE 1 below, among other suitable configurations. In one embodiment, primary coil 821 has an inductance of ~270 nH, an AC resistance<46 mΩ, and a DC resistance of ≤5 mΩ, for example.

TABLE 1

| Primary Coil 821 ($L_m$ 814) 46 Gauge Litz Wire |
| --- |
| 300 Strands 46 AWG - 24 turns per foot (TPF) |
| Single Build MW80 155*C |
| Single Nylon Served |
| Construction: 5 × 3 × 20/46 AWG |
| Ft per lb: 412 Nominal |
| OD: 0.039" Nominal |

Figure 26:
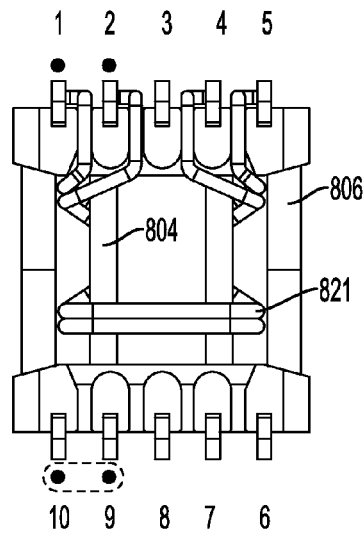
FIG. 26 illustrates a bottom view of the primary coil illustrated in FIG. 24.
Figure 27:
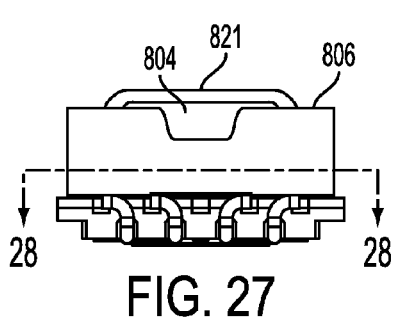
FIG. 27 illustrates a side view of the primary coil illustrated in FIG. 24.
Figure 28:
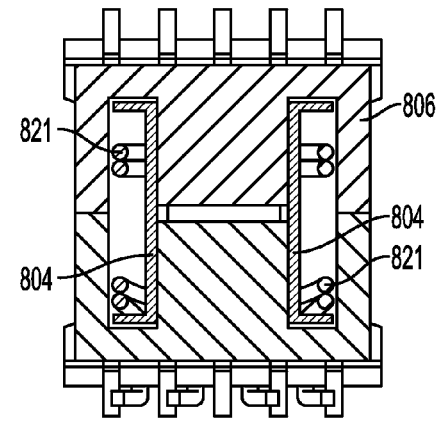
FIG. 28 illustrates a sectional view of the primary coil illustrated in FIG. 24 taken along section 28-28.

FIG. 26 illustrates a bottom view of the primary coil 821 (e.g., inductor $L_m$ 814 in FIG. 22) illustrated in FIG. 24. FIG. 27 illustrates a side view of the primary coil 821 illustrated in FIG. 24. FIG. 28 illustrates a sectional view of the primary coil 821 illustrated in FIG. 24 taken along section 28-28.

Figure 25:
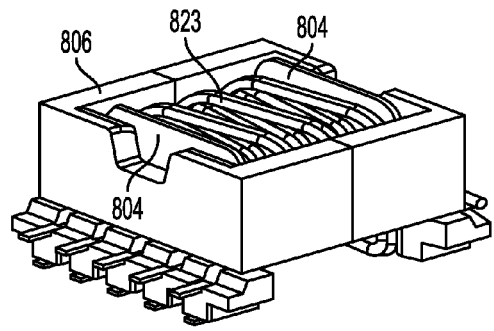
FIG. 25 illustrates a perspective view of one embodiment of a secondary coil of the transformer illustrated in FIG. 23.

FIG. 25 illustrates a perspective view of one embodiment of a secondary coil 823 (e.g., inductor $L_{sec}$ 816 in FIG. 22) of the transformer 404 illustrated in FIG. 23. In one embodiment, the secondary coil 823 windings may be constructed using 105 strand/44 gauge litz wire as indicated in TABLE 2 below, among other suitable configurations. In one embodiment, the secondary coil 823 has an inductance of 22 µH±5% @430 kHz, an AC resistance<2.5Ω, and a DC resistance ≤80 mΩ, for example.

TABLE 2

| Secondary Coil 823 ($L_{sec}$ 816) 44 Gauge Litz Wire |
| --- |
| 105 Strands 44 AWG 24 TPF |
| Single Build MW80 155*C |
| Single Nylon Served |
| Construction: 5 × 21/44 AWG |
| Ft per lb: 1214 Nominal |
| OD: 0.023" Nominal |

Figure 29:
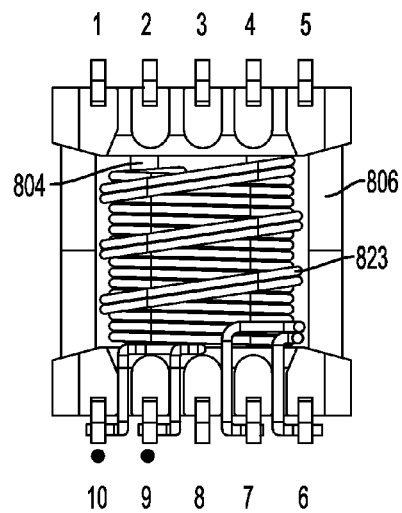
FIG. 29 illustrates a bottom view of the secondary coil illustrated in FIG. 25.
Figure 30:
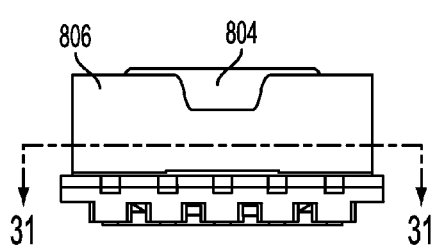
FIG. 30 illustrates a side view of the secondary coil illustrated in FIG. 25.
Figure 31:
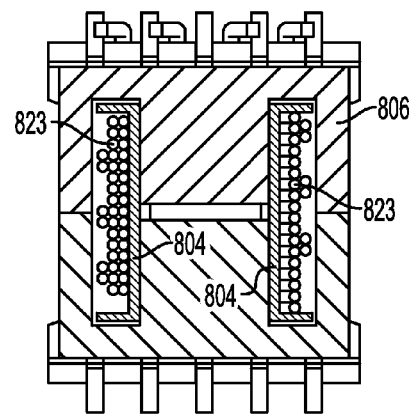
FIG. 31 illustrates a sectional view of the secondary coil illustrated in FIG. 30 taken along section 31-31.

FIG. 29 illustrates a bottom view of the secondary coil 823 (e.g., inductor $L_{sec}$ 816 in FIG. 22) illustrated in FIG. 25. FIG. 30 illustrates a side view of the secondary coil 823 illustrated in FIG. 25. FIG. 31 illustrates a sectional view of the secondary coil 823 illustrated in FIG. 30 taken along section 31-31.

Figure 32:
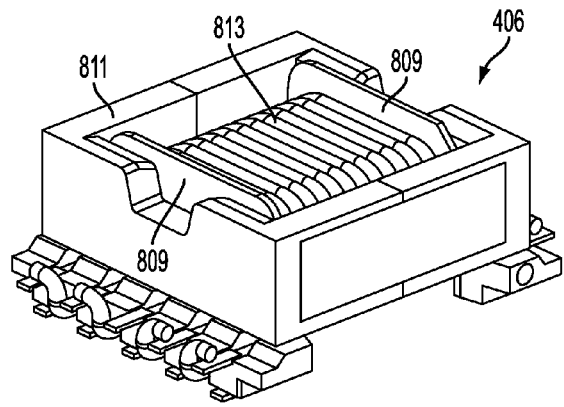
FIG. 32 illustrates a perspective view of an inductor employed in the RF drive circuit illustrated in FIG. 22.

FIG. 32 is a perspective view of one embodiment of the inductor 406 shown in FIGS. 8 and 10 and shown as inductor $L_s$ 812 in connection with the RF drive circuit 800 illustrated in FIG. 22. As shown in FIG. 32, in one embodiment, the inductor 406 comprises a bobbin 809, a ferrite core 811, and a coil 813. In one embodiment, the bobbin 809 may be a 10-pin surface mounted device (SMD) provided by Ferroxcube International Holding B.V. In one embodiment, the ferrite core 811 may be an EFD 20/107 N49. In one embodiment, the coil 813 windings may be constructed using 300 strand/46 gauge litz wire wound at 24 TPF. In one embodiment, the inductor $L_s$ 812 may have an inductance of ~345 nH±6% @430 kHz, an AC resistance<50 mΩ, and a DC resistance ≤7 mΩ, for example. The operating frequency range of the inductor $L_s$ 812 is from ~370 kHz to ~550 kHz, and a preferred frequency of ~430 kHz, and an operating current of ~15.5 A rms. It will be appreciated that these specification are provided as examples and should not be construed to be limiting of the scope of the appended claims.

Figure 33:
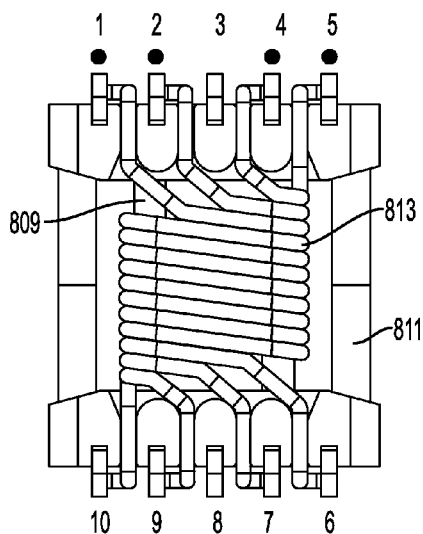
FIG. 33 illustrates a bottom view of the inductor illustrated in FIG. 32.
Figure 34:
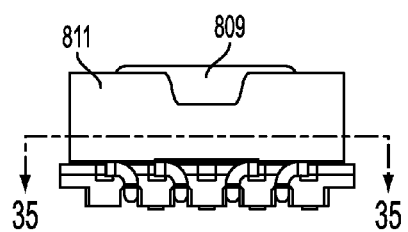
FIG. 34 illustrates a side view of the inductor illustrated in FIG. 32.
Figure 35:
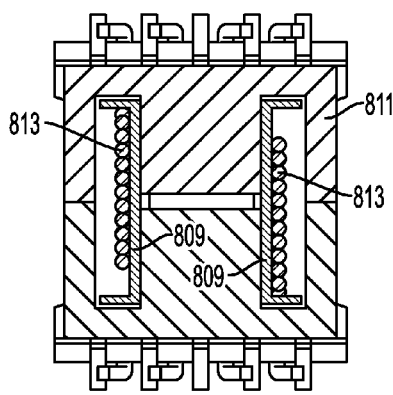
FIG. 35 illustrates a sectional view of the inductor illustrated in FIG. 34 taken along section 35-35.

FIG. 33 illustrates a bottom view of the inductor 406 (e.g., inductor $L_s$ 812 in FIG. 22) illustrated in FIG. 32. FIG. 34 illustrates a side view of the inductor 406 illustrated in FIG. 32. FIG. 35 illustrates a sectional view of the inductor 406 illustrated in FIG. 34 taken along section 35-35.

Accordingly, as described above in connection with FIGS. 23-35, in one embodiment, the transformer 404 (e.g., transformer 815) and/or the inductor 406 (e.g., inductor 812) used in the RF drive and control circuit 800 of FIG. 22 may be implemented with litz wire. One litz wire configuration may be produced by twisting 21 strands of 44 AWG SPN wire at 18 twists per foot (left direction twisting). Another litz wire configuration may be produced by twisting 5×21/44 AWG (105/44 AWG SPN), also at 18 twists per foot (left direction twisting). Other litz wire configurations include 300/46 AWG litz wire as well as 46 AWG or finer gauge size wire.

Figure 36:
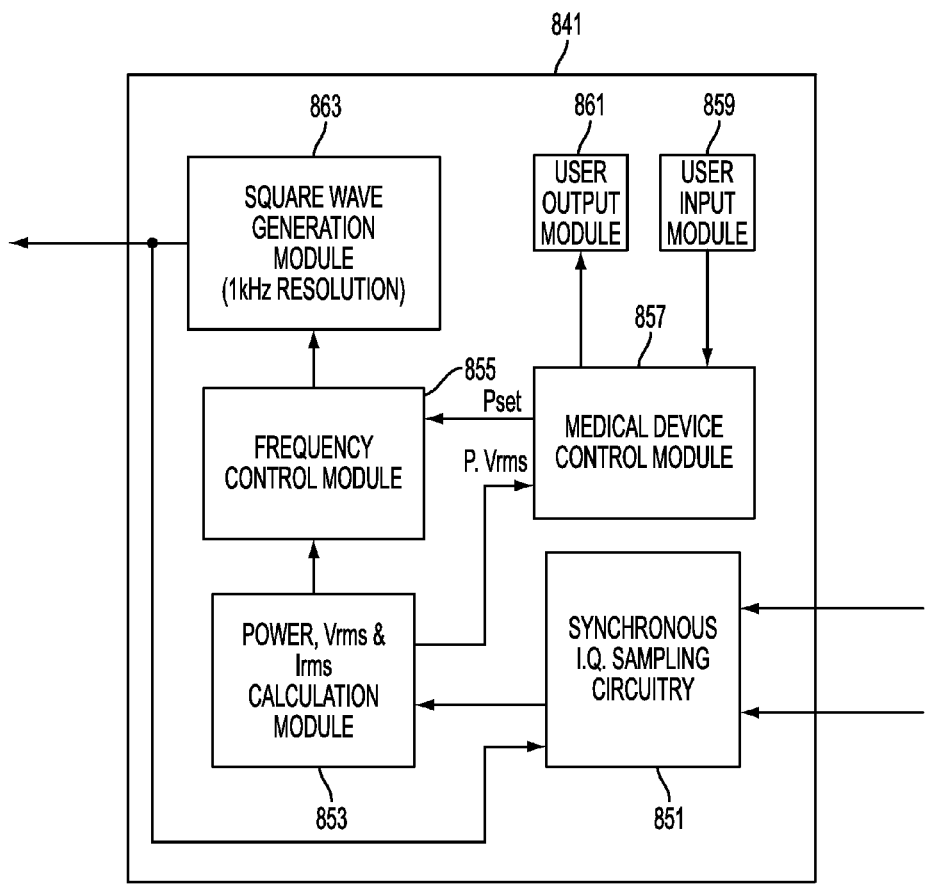
FIG. 36 illustrates main components of a controller, according to one embodiment.

FIG. 36 illustrates the main components of the controller 841, according to one embodiment. In the embodiment illustrated in FIG. 36, the controller 841 is a microprocessor based controller and so most of the components illustrated in FIG. 22 are software based components. Nevertheless, a hardware based controller 841 may be used instead. As shown, the controller 841 includes synchronous I, Q sampling circuitry 851 that receives the sensed voltage and current signals from the sensing circuitry 843 and 845 and obtains corresponding samples which are passed to a power, $V_{rms}$ and $I_{rms}$ calculation module 853. The calculation module 853 uses the received samples to calculate the RMS voltage and RMS current applied to the load 819 (FIG. 22; forceps 108 and tissue/vessel gripped thereby) and from them the power that is presently being supplied to the load 839. The determined values are then passed to a frequency control module 855 and a medical device control module 857. The medical device control module 857 uses the values to determine the present impedance of the load 819 and based on this determined impedance and a pre-defined algorithm, determines what set point power ($P_{set}$) should be applied to the frequency control module 855. The medical device control module 857 is in turn controlled by signals received from a user input module 859 that receives inputs from the user (for example pressing buttons or activating the control levers 114, 110 on the handle 104) and also controls output devices (lights, a display, speaker or the like) on the handle 104 via a user output module 861.

The frequency control module 855 uses the values obtained from the calculation module 853 and the power set point ($P_{set}$) obtained from the medical device control module 857 and predefined system limits (to be explained below), to determine whether or not to increase or decrease the applied frequency. The result of this decision is then passed to a square wave generation module 863 which, in this embodiment, increments or decrements the frequency of a square wave signal that it generates by 1 kHz, depending on the received decision. As those skilled in the art will appreciate, in an alternative embodiment, the frequency control module 855 may determine not only whether to increase or decrease the frequency, but also the amount of frequency change required. In this case, the square wave generation module 863 would generate the corresponding square wave signal with the desired frequency shift. In this embodiment, the square wave signal generated by the square wave generation module 863 is output to the FET gate drive circuitry 805, which amplifies the signal and then applies it to the FET 803-1. The FET gate drive circuitry 805 also inverts the signal applied to the FET 803-1 and applies the inverted signal to the FET 803-2.

Figure 37:
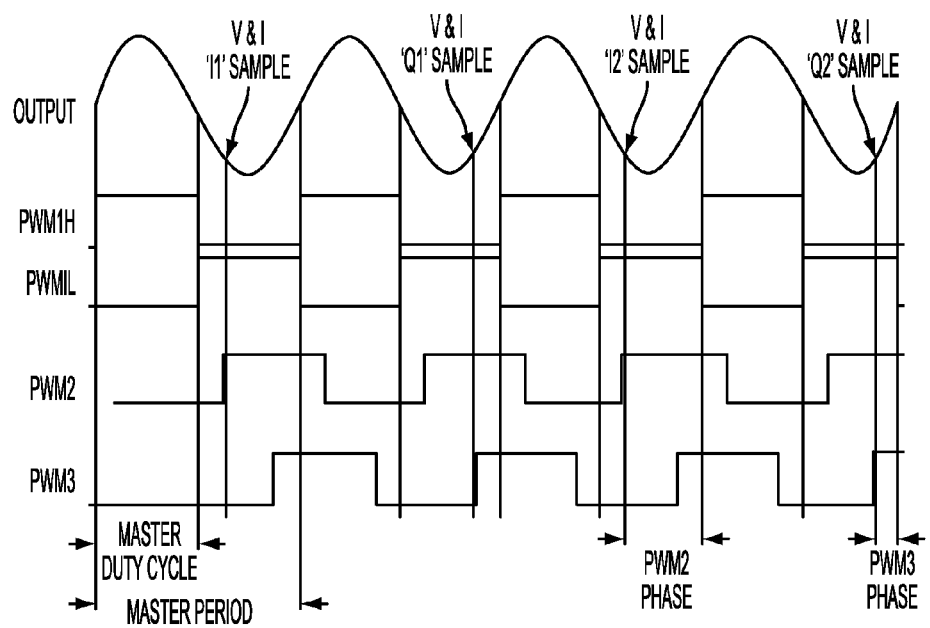
FIG. 37 is a signal plot illustrating the switching signals applied to a field effect transistor (FET), a sinusoidal signal representing the measured current or voltage applied to a load, and the timings when a synchronous sampling circuit samples the sensed load voltage and load current, according to one embodiment.

FIG. 37 is a signal plot illustrating the switching signals applied to the FETs 803, a sinusoidal signal representing the measured current or voltage applied to the load 819, and the timings when the synchronous sampling circuitry 851 samples the sensed load voltage and load current, according to one embodiment. In particular, FIG. 37 shows the switching signal (labeled PWM1 H) applied to upper FET 803-1 and the switching signal (labeled PWM1 L) applied to lower FET 803-2. Although not illustrated for simplicity, there is a dead time between PWM1H and PWM1L to ensure that that both FETs 803 are not on at the same time. FIG. 17 also shows the measured load voltage/current (labeled OUTPUT). Both the load voltage and the load current will be a sinusoidal waveform, although they may be out of phase, depending on the impedance of the load 819. As shown, the load current and load voltage are at the same drive frequency (f) as the switching Signals (PWM1 H and PWM1 L) used to switch the FETs 803. Normally, when sampling a sinusoidal signal, it is necessary to sample the signal at a rate corresponding to at least twice the frequency of the signal being sampled—i.e. two samples per period. However, as the controller 841 knows the frequency of the switching signals, the synchronous sampling circuit 851 can sample the measured voltage/current signal at a lower rate. In this embodiment, the synchronous sampling circuit 851 samples the measured signal once per period, but at different phases in adjacent periods. In FIG. 37, this is illustrated by the "I" sample and the "Q" sample. The timing that the synchronous sampling circuit 51 makes these samples is controlled, in this embodiment, by the two control signals PWM2 and PWM3, which have a fixed phase relative to the switching signals (PWM1 H and PWM1 L) and are out of phase with each other (preferably by quarter of the period as this makes the subsequent calculations easier). As shown, the synchronous sampling circuit 851 obtains an "I" sample on every other rising edge of the PWM2 signal and the synchronous sampling circuit 851 obtains a "0" sample on every other rising edge of the PWM3 signal. The synchronous sampling circuit 851 generates the PWM2 and PWM3 control signals from the square wave signal output by the square wave generator 863 (which is at the same frequency as the switching signals PWM1 H and PWM1 L). Thus control signals PWM2 and PWM3 also changes (whilst their relative phases stay the same). In this way, the sampling circuitry 851 continuously changes the timing at which it samples the sensed voltage and current signals as the frequency of the drive signal is changed so that the samples are always taken at the same time points within the period of the drive signal. Therefore, the sampling circuit 851 is performing a "synchronous" sampling operation instead of a more conventional sampling operation that just samples the input signal at a fixed sampling rate defined by a fixed sampling clock.

The samples obtained by the synchronous sampling circuitry 851 are then passed to the power, $V_{rms}$ and $I_{rms}$ calculation module 853 which can determine the magnitude and phase of the measured signal from just one "I" sample and one "Q" sample of the load current and load voltage. However, in this embodiment, to achieve some averaging, the calculation module 853 averages consecutive "I" samples to provide an average "I" value and consecutive "Q" samples to provide an average "0" value; and then uses the average I and Q values to determine the magnitude and phase of the measured signal (in a conventional manner). As those skilled in the art will appreciate, with a drive frequency of about 400 kHz and sampling once per period means that the synchronous sampling circuit 851 will have a sampling rate of 400 kHz and the calculation module 853 will produce a voltage measure and a current measure every 0.01 ms. The operation of the synchronous sampling circuit 851 offers an improvement over existing products, where measurements can not be made at the same rate and where only magnitude information is available (the phase information being lost).

In one embodiment, the RF amplifier and drive circuitry for the electrosurgical medical instrument 100 employs a resonant mode step-up switching regulator, running at the desired RF electrosurgical frequency to produce the required tissue effect. The waveform illustrated in FIG. 18 can be employed to boost system efficiency and to relax the tolerances required on several custom components in the electronics system 400. In one embodiment, a first generator control algorithm may be employed by a resonant mode switching topology to produce the high frequency, high voltage output signal necessary for the medical instrument 100. The first generator control algorithm shifts the operating frequency of the resonant mode converter to be nearer or farther from the resonance point in order to control the voltage on the output of the device, which in turn controls the current and power on the output of the device. The drive waveform to the resonant mode converter has heretofore been a constant, fixed duty cycle, with frequency (and not amplitude) of the drive waveform being the only means of control.

Figure 38:
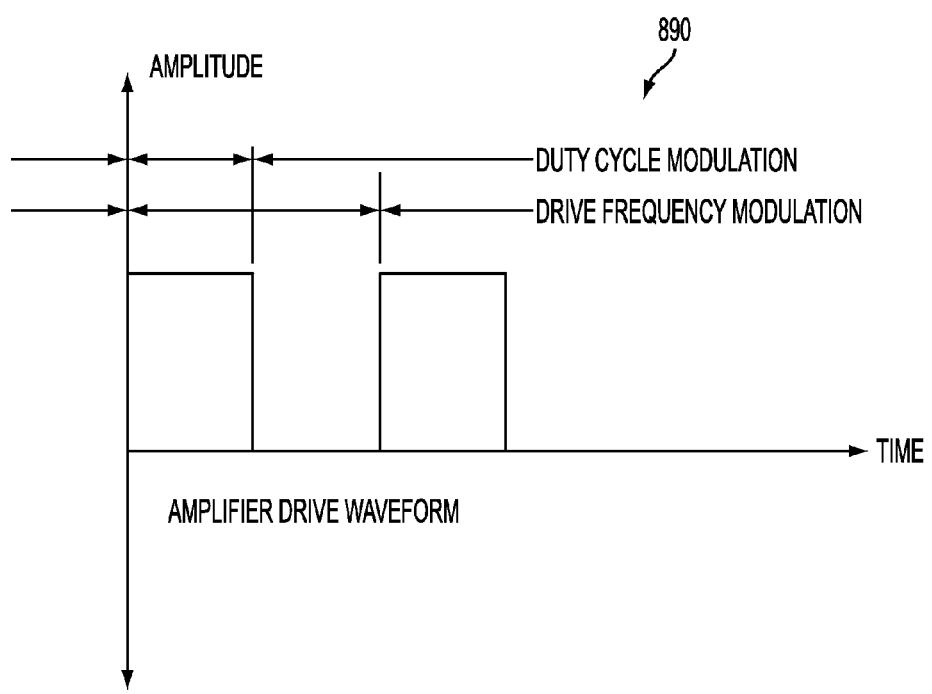
FIG. 38 illustrates a drive waveform for driving an FET gate drive circuit, according to one embodiment.

FIG. 38 illustrates a drive waveform for driving the FET gate drive circuitry 805, according to one embodiment. Accordingly, in another embodiment, a second generator control algorithm may be employed by a resonant mode switching topology to produce the high frequency, high voltage output signal necessary for the medical instrument 100. The second generator control algorithm provides an additional means of control over the amplifier in order to reduce power output in order for the control system to track the power curve while maintaining the operational efficiency of the converter. As shown in FIG. 38, according to one embodiment, the second generator control algorithm is configured to not only modulate the drive frequency that the converter is operating at, but to also control the duty cycle of the drive waveform by duty cycle modulation. Accordingly, the drive waveform 890 illustrated in FIG. 38 exhibits two degrees of freedom. Advantages of utilizing the drive waveform 890 modulation include flexibility, improved overall system efficiency, and reduced power dissipation and temperature rise in the amplifier's electronics and passive inductive components, as well as increased battery life due to increased system efficiency.

Figure 39:
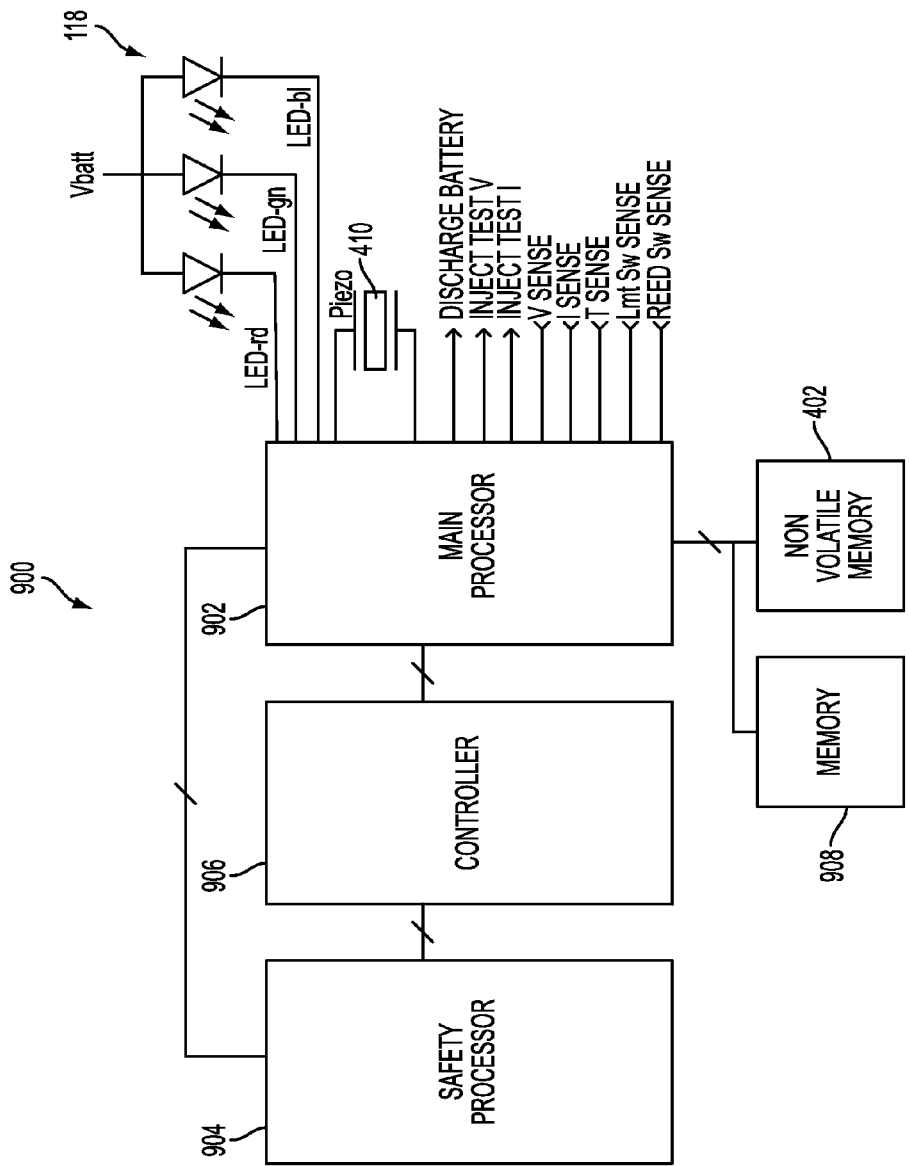
FIG. 39 illustrates a diagram of a digital processing system located on a first substrate, according to one embodiment.

FIG. 39 illustrates a diagram of the digital processing system 900 located on the first substrate 408a, according to one embodiment. The digital processing system 900 comprises a main processor 902, a safety processor 904, a controller 906, a memory 908, and a non-volatile memory 402, among other components that are not shown for clarity of disclosure. The dual processor architecture comprises a first operation processor referred to as the main processor 902, which is the primary processor for controlling the operation of the medical instrument 100. In one aspect, the main processor 902 executes the software instructions to implement the controller 841 shown in FIG. 16. In one embodiment, the main processor 902 also may comprise an analog-to-digital (A/D) converter and pulse width modulators (PWM) for timing control.

The main processor 902 controls various functions of the overall medical instrument 100. In one embodiment, the main processor receives voltage sense (V Sense) and current sense (I Sense) signals measured at the load (represented by the load resistance $R_{load}$ 819 in FIG. 22) corresponding to the impedance of the forceps' jaws and any tissue or vessel gripped by the forceps 108. For example, the main processor 902 receives the V Sense and I Sense signals for the voltage sensing circuitry 843 and current sensing circuitry 845, as shown in FIG. 15. The main processor 902 also receives tissue temperature (T sense) measurement at the load. Using the V Sense, I Sense, and T Sense, the processor 902 can execute a variety of algorithms to detect the state of the tissue based on impedance Z, where Z=V Sense/I Sense. In one embodiment, the medical instrument 100 is frequency agile from about 350 kHz to about 650 kHz. As previously discussed, the controller 841 changes the resonant operating frequency of the RF amplifier sections, controlling the pulse width modulation (PWM), reducing the output voltage (V) to the load, and enhancing the output current (I) to the load as described in connection with FIGS. 22 and 36-38, for example.

Examples of frequency agile algorithms that may be employed to operate the present surgical instrument 100 are described in the following commonly owned U.S. Patent Applications, each of which is incorporated herein by reference in its entirety: (1) U.S. patent application Ser. No. 12/896,351, entitled DEVICES AND TECHNIQUES FOR CUTTING AND COAGULATING TISSUE; (2) U.S. patent application Ser. No. 12/896,479, entitled SURGICAL GENERATOR FOR ULTRASONIC AND ELECTROSURGICAL; (3) U.S. patent application Ser. No. 12/896,345, entitled SURGICAL GENERATOR FOR ULTRASONIC AND ELECTROSURGICAL DEVICES; (4) U.S. patent application Ser. No. 12/896,384, entitled SURGICAL GENERATOR FOR ULTRASONIC AND ELECTROSURGICAL DEVICES; (5) U.S. patent application Ser. No. 12/896,467, entitled SURGICAL GENERATOR FOR ULTRASONIC AND ELECTROSURGICAL DEVICES; (6) U.S. patent application Ser. No. 12/896,451, entitled SURGICAL GENERATOR FOR ULTRASONIC AND ELECTROSURGICAL DEVICES; (7) U.S. patent application Ser. No. 12/896,470, entitled SURGICAL GENERATOR FOR ULTRASONIC AND ELECTROSURGICAL DEVICES; and U.S. patent application Ser. No. 12/503,775, entitled ULTRASONIC DEVICE FOR CUTTING AND COAGULATING WITH STEPPED OUTPUT.

In one embodiment, the main processor 902 also detects the limit switch end of stroke position (Lmt Sw Sense). The limit switch is activated when the knife reaches the end of stroke limit. The signal generated by the limit switch Lmt Sw Sense is provided to the main processor 902 to indicate the end-of-stroke condition of the knife.

In one embodiment, the main processor 902 also senses an actuation signal (Reed Sw Sense) associated with the magnetically operated element 606 located on the electronics system 400. As previously described the magnetically operated element 606 is initially actuated when the initialization clip 600, 650 is removed. When the Reed Sw Sense is detected by the main processor 902, an algorithm is executed to control the operation of the medical instrument 100. One embodiment of such an algorithm is described in more detail hereinbelow. Further, on initial power up, when the magnetically operated element 606 connects the battery 300 supply to the electronics system 400, a low resistance load is applied to the terminals of the battery 300 to check the internal resistance of the battery 300. This enables the main processor 902 to determine the charge state of the battery 300 or in other words, determines the ability of the battery 300 to deliver power to the electronics system 400. In one embodiment, the main processor 902 may simply determine the absolute value of the difference between the unloaded and loaded battery 300. If the main processor 902 determines that the battery 300 does not have enough capacity to deliver a suitable amount of power, the main processor 902 disables the medical instrument 100 and outputs a Discharge Battery signal, as discussed in more detail hereinbelow, to controllably discharge the battery 300 such that it cannot be reused and is classified as an out-of-the box failure.

In one embodiment, as part of the algorithm, the main processor 902 enables one or more visual feedback elements 118. As shown in FIG. 39, the visual feedback elements 118 comprise at least one red LED, at least one green LED, and at least one blue LED. Each of the LEDs are energized based on algorithms associated with the medical instrument 100. The main processor 902 also actuates an audio feedback element 410 based on algorithm associated with the medical instrument 100. In one embodiment, the audio feedback element 410 includes a piezoelectric buzzer operating at 65 dBa at 1 meter at a frequency between about 2.605 kHz to 2.800 kHz, for example. As previously discussed, the visual and audio feedback elements 118, 410 are not limited to the devices disclosed herein and are intended to encompass other visual and audio feedback elements.

In one embodiment, the main processor 902 executes battery shut-off and battery-drain/kill algorithms to shut-off the instrument 100 and/or drain the battery 300 under certain conditions described below. The algorithms monitor instrument usage and battery voltage and trigger shutdown of the instrument 100 and the drain the battery 300 in the event of unrecoverable faults or as a natural way to shutdown the instrument 100 and drain the battery 300.

In one embodiment, an unrecoverable event triggers the medical instrument 100 to shutdown and drain the battery 330. Events that can trigger the medical instrument 100 to shutdown and drain the battery 300 include, without limitation, (1) the detection of five consecutive firing short circuits; (2) activation of RF power when the activation button 114 is not pressed; (3) activation of RF power without activation of the audible feedback; (4) activation of the audible feedback without RF power; (5) the switch is stuck at power up for >30 seconds; (6) the resting voltage of the battery 300 is less than 10.848V after any firing; and (7) three consecutive firings that are over or under the established load curve extremes of +/−20%.

In one embodiment, the medical instrument 100 may be shutdown and the battery 300 drained as a result natural usage of the instrument 100, which includes, without limitation: (1) when the medical instrument 100 completes five firings after detecting a resting voltage of the battery 300 of 11.02V; (2) after the clip 600, 650 has been removed from the medical instrument 100, if the instrument 100 has completed a real firing (more than three joules and the user gets the cycle complete tone3) and if the user replaces the initialization clip 600, 650 on the instrument 100, the instrument 100 will no longer be useable when they clip 600, 650 is once again removed from the instrument 100; (3) when the user depresses the disposal button 120 located on the bottom of the handle 104 of the instrument 100 for four seconds; (4) upon reaching a time limit: (a) after at least eight hours of use and if not used between hours six through eight, the instrument 100 it will shutdown; and (b) if used at least once between hours six and eight, the instrument 100 will extend the time limit to ten hours and then shutdown.

In one embodiment, the main processor 902 provides certain output signals. For example, one output signal is provided to the circuitry to discharge the battery 300 (Discharge Battery) signal. This is explained in more detail with reference to FIG. 40. There may be a need to discharge the battery 300 under several conditions according to algorithms associated with the medical instrument 100. Such conditions and algorithm are discussed in more detail hereinbelow. In one embodiment, the battery 300 used to power the medical instrument 100 has an initial out of the box capacity ranging from about 6 to about 8 hours up to about 10 hours under certain circumstances. After a medical procedure, some capacity will remain in the battery 300. Since the battery 300 is designed as a single use battery and is not rechargeable, the battery 300 is controllably discharged after use to prevent reuse of the medical instrument 100 when the battery 300 has a partial capacity.

In one embodiment, the main processor 902 can verify the output voltage (V) and current (I) sensing function by an artificial injection of voltage and current into the load. The main processor 902 then reads back the voltage and current from the load and determines whether the medical instrument 100 can operate or fail in safe mode. In one embodiment, the test voltage and current are applied to the dummy load via an electronically controlled switch. For example, the electronic switch may comprise a two-pole relay. The main processor 902 verifies the output sensing function once per hour when it is inactive and once prior to every firing. It will be appreciated that these periods may vary based on the particular implementation. To verify the output sensing function, the main processor 902 outputs inject test voltage (Inject Test V) and inject test current (Inject test I) signals to the output sensing test circuit described in connection with FIG. 41 hereinbelow. As previously described, the main processor 902 reads the sensed voltage and current signals V Sense and I Sense to determine the operation of the voltage (V) and current (I) sensing function of the medical instrument 100.

The main processor 902 is also coupled to a memory 908 and the nonvolatile memory 402. The computer program instructions executed by the main processor 902 are stored in the nonvolatile memory 902 (e.g., EEPROM, FLASH memory, and the like). The memory 908, which may be random access memory (RAM) may be used for storing instructions during execution, measured data, variables, among others. The memory 908 is volatile and its contents are erased when the battery 300 is discharged below a predetermine voltage level. The nonvolatile memory 402 is nonvolatile and its contents are not erased when the battery 300 is discharged below a predetermined level. In one embodiment, it may be desirable to erase the contents of the nonvolatile memory 402 to prevent its reuse, for example, when the medical instrument 100 has already been utilized in a procedure, the instrument 100 is determined to be an out-of-the box failure, or when the instrument 100 otherwise fails. In each of these circumstances, the main processor 902 initiates a battery 300 discharge operation. In such circumstances, program instructions in the nonvolatile memory 402 for erasing nonvolatile memory are transferred to the memory 908 where program execution resumes. The instructions executed from the memory 908 then erase the contents of the nonvolatile memory 402.

The safety processor 904 is coupled to the main processor 902 and monitors the operation of the main processor 902. If the safety processor 904 determines a malfunction of the main processor 902, the safety processor 904 can disable the operation of the main processor 902 and shuts down the medical instrument 100 in a safe mode.

The controller 906 is coupled to both the main processor 902 and the safety processor 904. In one embodiment, the controller 906 also monitors the operation of the main processor 902 and if the main processor 902 loses control, the controller 906 enables the safety processor to shut down the RF amplifier section in a safe manner. In one embodiment the controller 906 may be implemented as complex programmable logic device (CPLD), without limitation.

To preserve or extend the life of the battery 300, the main processor 902, the safety processor 904, and/or the controller 906 may be powered down (e.g., placed in sleep mode) when they are not in use. This enables the digital processing system 900 to conserve energy to preserve or extend the life of the battery 300.

In various embodiments, the main processor 902, the safety processor 904, or the controller 906 may comprise several separate functional elements, such as modules and/or blocks. Although certain modules and/or blocks may be described by way of example, it can be appreciated that a greater or lesser number of modules and/or blocks may be used and still fall within the scope of the embodiments. Further, although various embodiments may be described in terms of modules and/or blocks to facilitate description, such modules and/or blocks may be implemented by one or more than one hardware component, e.g., processor, Complex Programmable Logic Device (CPLD), Digital Signal Processor (DSP), Programmable Logic Devices (PLD), Application Specific Integrated Circuit (ASIC), circuits, registers and/or software components, e.g., programs, subroutines, logic and/or combinations of hardware and software components.

In one embodiment, the digital processing system 900 may comprise one or more embedded applications implemented as firmware, software, hardware, or any combination thereof. The digital processing system 900 may comprise various executable modules such as software, programs, data, drivers, application program interfaces (APIs), and so forth. The firmware may be stored in the nonvolatile memory 402 (NVM), such as in bit-masked read-only memory (ROM) or flash memory. In various implementations, storing the firmware in ROM may preserve flash memory. The NVM may comprise other types of memory including, for example, programmable ROM (PROM), erasable programmable ROM (EPROM), electrically erasable programmable ROM (EEPROM), or battery backed random-access memory 908 (RAM) such as dynamic RAM (DRAM), Double-Data-Rate DRAM (DDRAM), and/or synchronous DRAM (SDRAM).

Figure 40:
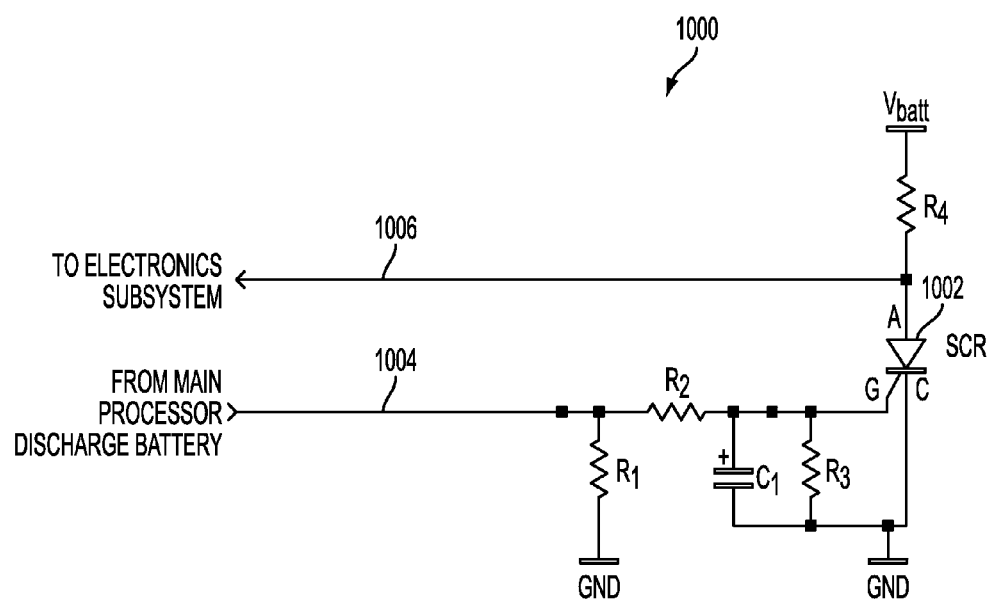
FIG. 40 illustrates a battery discharge circuit, according to one embodiment.

FIG. 40 illustrates a battery discharge circuit 1000, according to one embodiment. Under normal operation line 1004 is held at a low potential and a current control device, such as a silicon controlled rectifier 1002, is in the OFF state and the battery voltage $V_{batt}$ is applied to the electronics system 400 since no current flows from the anode "A" to the cathode "C" of the silicon controlled rectifier 1002. When, a high potential control signal "Discharge Battery" is applied by the main processor 902 on line 1004, the gate "G" of the silicon controlled rectifier 1002 is held high by capacitor $C_1$ and the silicon controlled rectifier 1002 conducts current from the anode "A" to the "C." The discharge current is limited by resistor $R_4$. In alternate embodiments, rather then using the silicon controlled rectifier 1002, the current control device may be implemented using one or more diodes, transistors (e.g., FET, bipolar, unipolar), relays (solid state or electromechanical), optical isolators, optical couplers, among other electronic elements that can be configured to for an electronic switch to control the discharge of current from the battery 300.

FIG. 41 illustrates a RF amplifier section with an output sensing test circuit and magnetic switch element, according to one embodiment. As previously discussed, in one embodiment, the main processor 902 can verify the output current (I)

and output voltage (V) sensing function by injecting a corresponding first test current 1102 and second test current 1104 into a dummy load 1114. The main processor 902 then reads back the corresponding output sense current (I OutSense 1) through current sense terminal 1120 and output sense current (I Out Sense 2) through voltage sense terminal 1122 from the dummy load 1114 and determines whether the medical instrument 100 can operate or fail in safe mode. In one embodiment, the test current and voltage are applied to the dummy load via electronically controlled switches such as FET transistors, solid state relay, two-pole relay, and the like. The main processor 902 verifies the output sensing functions once per hour when it is inactive and once prior to every firing. It will be appreciated that these periods may vary based on the particular implementation.

To verify the output sensing function, the main processor 902 disables the operation of the RF amplifier section 1112 by disabling the driver circuit 1116. Once the RF amplifier section 1112 is disabled, the main processor 902 outputs a first inject test current (Inject Test I) signal and a second inject test voltage (Inject Test V) signal to the output sensing test circuit 1100. As a result a first test current 1102 is injected into resistors that turn ON transistor T1 1106, which turns ON transistor T2 1108 to generate I Out Sense 1 current through the transistor T2 1108. The current I Out Sense 1 flows out of the current sense terminal 1120 and is detected by the main processor 902 as the I Sense signal. A second test current 1104 is applied through the input section of a solid state relay 1110 (SSR). This causes a current I Out Sense 2 to flow through the dummy load 1114. The current I Out Sense 2 flows out of the current sense terminal 1122 and is detected by the main processor 902 as the V Sense signal. The dummy load 1114 load comprises a first voltage divider network comprised of resistors R1-R4 and a second voltage divider network comprised of R5-R8. As previously described, the main processor 902 reads the sensed voltage and current signals V Sense and I Sense to determine the operation of the voltage (V) and current (I) sensing function of the medical instrument 100.

In one embodiment, the magnetically actuated element 606, which works in conjunction with the magnet 602 located in the clip 600, 650. As shown in FIG. 41, in one embodiment, the magnetically operated element 606 may be implemented as a reed switch 1118. The reed switch 1118 electrically disconnects the battery power from the electronics system 400 while it is held in a first state by the magnetic flux generated by the magnet 602. When the magnet 602 is removed and the magnetic flux does not influence the reed switch 1118, battery power is connected to the electronics system 400 and the system undergoes an initialization algorithm, as described hereinbelow.

Before the describing the initialization algorithm, several connection options for the battery 300 are now described with reference to FIGS. 42-47. As previously discussed, the electronics system 400 will not be powered when undergoing sterilization, and will draw no current. In one embodiment, the electronics system 400 is disabled by a magnetically operated element located in the clip 600, 650, one example of which is the reed switch 1118 shown in FIG. 41, and the magnet 602 which is encased in the clip 600 and the tilted magnetic pocket 654 of the clip 650. The clip 600, 650 is fitted to the medical instrument 100 as part of the manufacturing process, and must be removed to enable power from the battery 300. When powered, in the idle condition the load circuit draws an average of about 10 mA, with peaks of up to about 65 mA. When the activation button 114 is pressed, the device draws an average of about 5 A, with peaks of about 15.5 A from the battery 300. When packaged, the jaws are closed and there is no material between them. The voltage generated across the jaws is about 85V rms. This arrangement means there are two methods for preventing the generation of high voltages or currents—the magnetic clip 600, 650 is the primary disabling mechanism, and the activation button 114 is the second.

As previously discussed, certain sections of the hardware circuits may be shut down or placed in sleep mode to conserve energy and thus extend the life of the battery 300. In particular, amplifier circuits associated with the injection of the test current and test voltage and sensing the output sense currents may be placed in sleep mode or periodically shut down to conserve energy.

Figure 42:
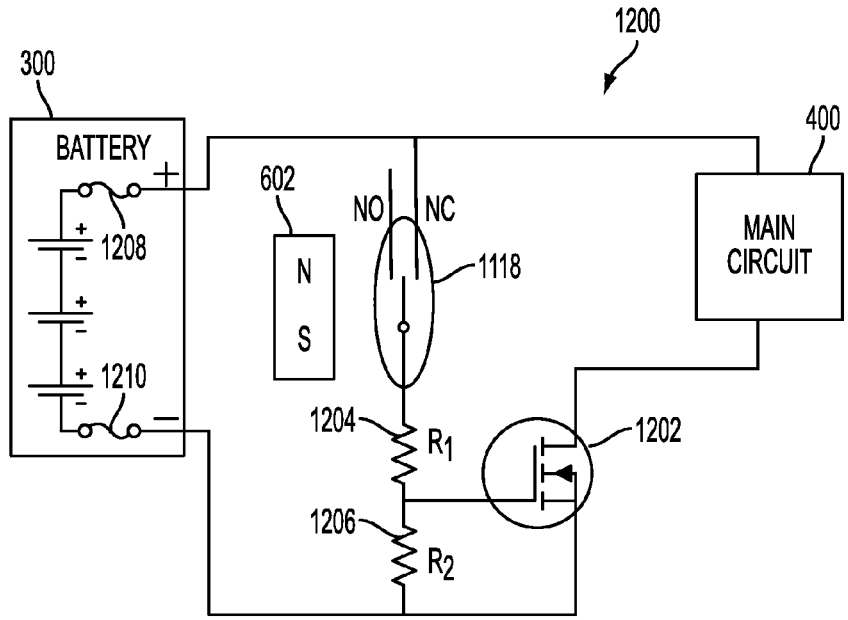
FIG. 42 illustrates a fused battery connected to a substrate-mounted FET, according to one embodiment.

FIG. 42 illustrates a fused battery connected to a substrate-mounted field effect transistor (FET), according to one embodiment. In the embodiment shown in FIG. 42, a battery connection circuit 1200 comprises the battery 300, the magnet 602, the reed switch 1118, an FET 1202, two resistors R1, R2 1204, 1206, and the electronics system 400. In this implementation, when the protective clip 600 is removed, the reed switch 1118 closes, enabling current to flow through the control FET 1202, thus coupling the electronics system 400 to the return (−) terminal of the battery 300. Leakage current through the FET is approximately 1 uA. The battery is coupled to the (+) and (−) terminals via corresponding fuses 1208, 1210.

Figure 43:
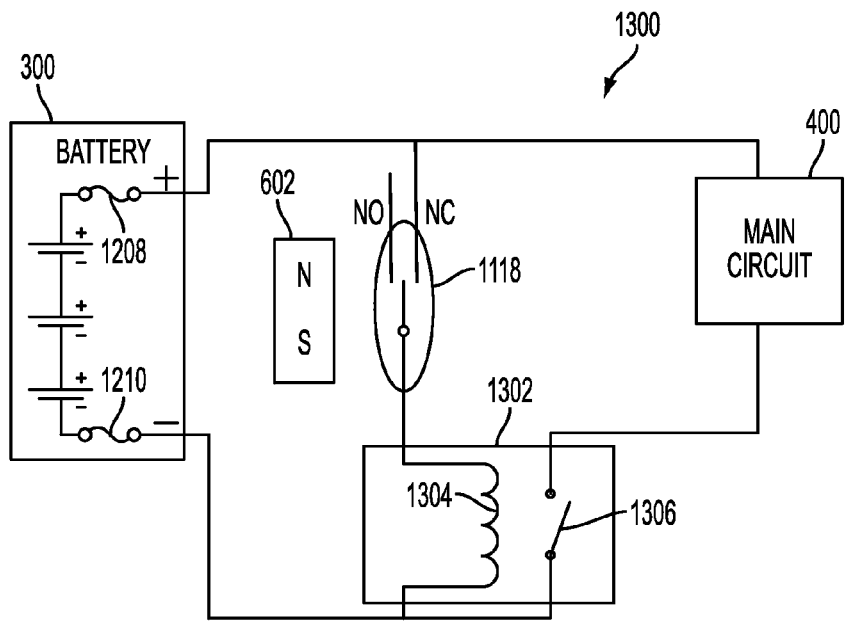
FIG. 43 illustrates a fused battery connected to a substrate-mounted control relay, according to one embodiment.

FIG. 43 illustrates a fused battery connected to a substrate-mounted control relay, according to one embodiment. In the embodiment shown in FIG. 43, a battery connection circuit 1300 comprises the battery 300, the magnet 602, the reed switch 1118, and a control relay 1302 comprising a primary winding 1304 that controls a switch 1306. In this implementation, when the protective clip 600 is removed, the reed switch 1118 closes, energizing the relay 1302 and connecting the electronics system 400 to the return (−) terminal of the battery 300. Leakage current is zero, because the switch 1306 is physically open when the primary winding 1304 in not energized. The operating current, however, to hold the relay 1304 open is approximately 5 mA, which could involve increasing battery size.

Figure 44:
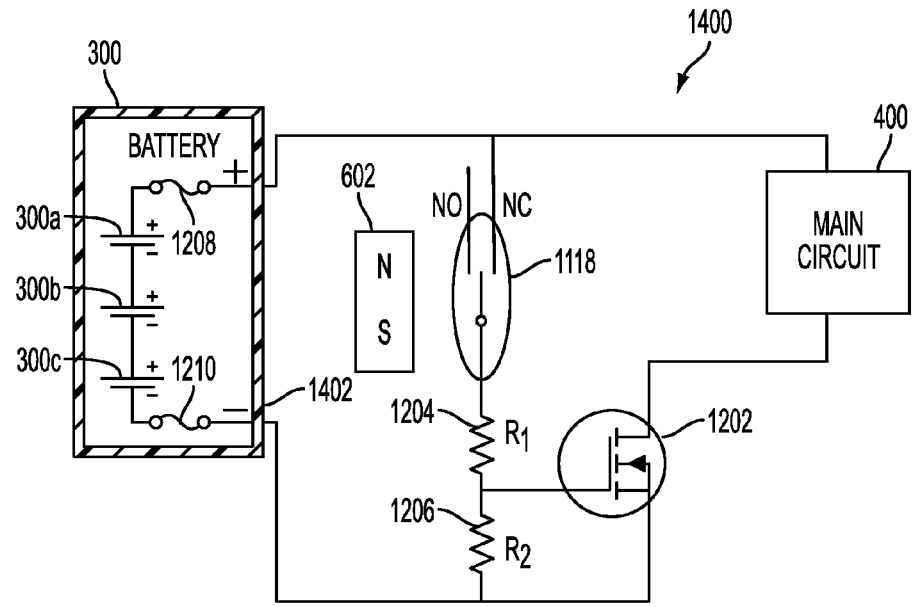
FIG. 44 illustrates a potted fused battery connected to a substrate-mounted FET, according to one embodiment.

FIG. 44 illustrates a potted fused battery connected to a substrate-mounted FET, according to one embodiment. The connection circuit 1400 is similar to the connection circuit 1200 shown in FIG. 42, but with the top of the battery 300 potted in potting compound 1402. Thus, EtO sterilization gas will have no access to the individual battery cells 300*a*, 300*b*, 300*c*, and the first exposed contact is to the fused contacts.

Figure 45:
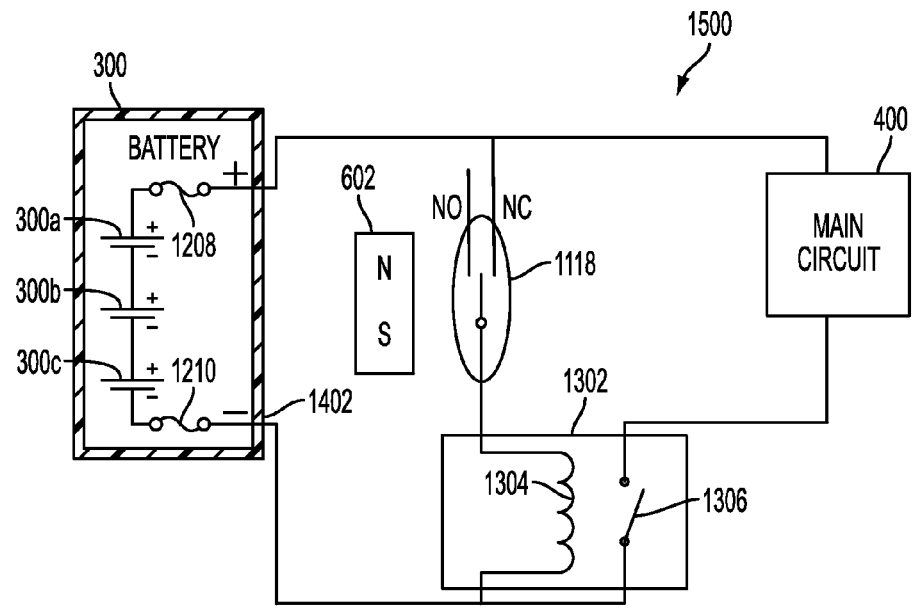
FIG. 45 illustrates a potted fused battery connected to a substrate-mounted control relay, according to one embodiment.

FIG. 45 illustrates a potted fused battery connected to a substrate-mounted control relay, according to one embodiment. The connection circuit 1500 is similar to the connection circuit 1300 shown in FIG. 23, but with the top of the battery 300 potted in potting compound 1402. Thus, EtO sterilization gas will have no access to the individual battery cells 300*a*, 300*b*, 300*c*, and the first exposed contact is to the fused contacts.

Figure 46:
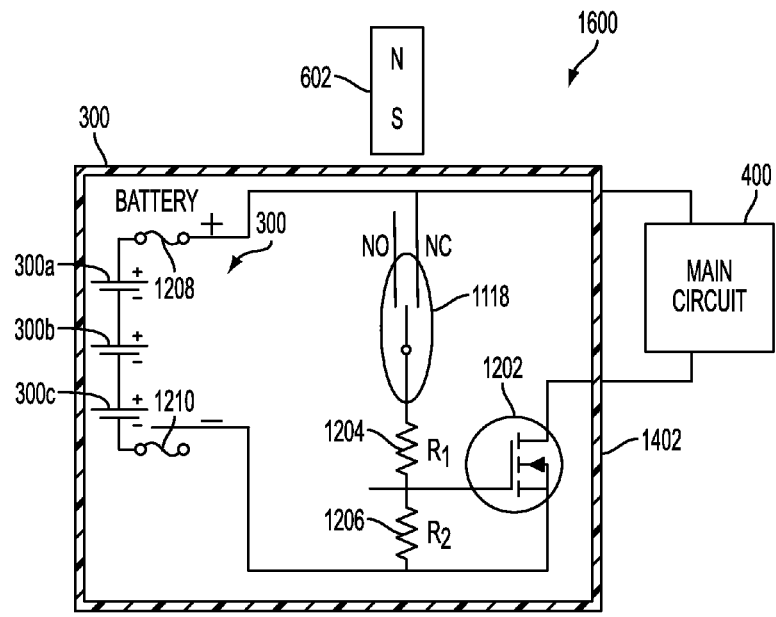
FIG. 46 illustrates a potted fused battery including a reed relay and control FET, according to one embodiment.

FIG. 46 illustrates a potted fused battery including a reed relay and control FET, according to one embodiment. The connection circuit 1600 is similar to the connection circuit 1400 shown in FIG. 24, but with reed relay 1118 and the control FET 1202 included in the potting compound 1402 as well as the top of the battery 300. Thus, EtO sterilization gas will have no access to the individual battery cells 300*a*, 300*b*, 300*c*, the reed relay 1118, and the control FET 1202, and the first exposed contact is to the fused contacts.

Figure 47:
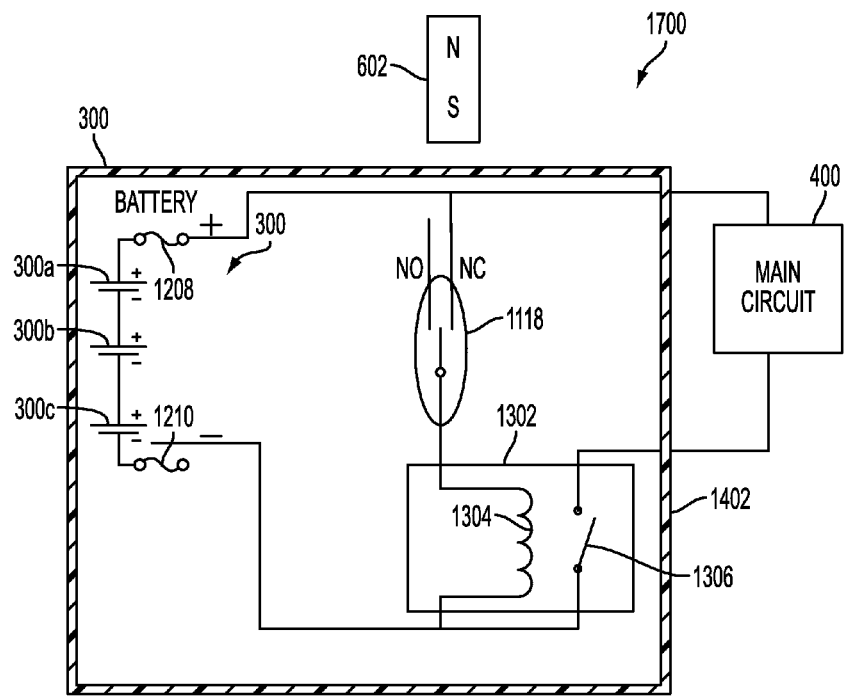
FIG. 47 illustrates a potted fused battery including a reed relay and control relay, according to one embodiment.

FIG. 47 illustrates a potted fused battery including a reed relay and control relay, according to one embodiment. The connection circuit 1700 is similar to the connection circuit 1500 shown in FIG. 45, but with reed relay 1118 and the control relay 1302 included in the potting compound 1402 as well as the top of the battery 300. Thus, EtO sterilization gas will have no access to the individual battery cells 300*a*, 300*b*, 300*c*, the reed relay 1118, and the control relay 1302, and the first exposed contact is to the fused contacts.

Having described various systems associated with the medical instrument 100, the description now turns to a user interface specification of the medical instrument 100, according to one embodiment. Accordingly, in one embodiment, the medical instrument 100 comprises visual feedback elements 118*a*, 118*b*. In one embodiment, the visual feedback elements 118*a*, 118*b* each comprises RED, GREEN, BLUE (RGB) LEDs as shown in FIG. 39.

The state of the medical instrument 100 can be determined by the state of the visual feedback elements 118*a*, 118*b* as follows:

Solid Green: indicates that the medical instrument 100 is ready to be used, everything is functioning normally.

Flashing Green: indicates that medical instrument 100 is ready to be used, but there is only enough energy for a limited, e.g., low, number of operations such as transections remaining (a minimum of 5 transections are left when flashing first begins). In one embodiment, the rate of flashing is 300 ms on, 300 ms off, 300 ms on, 300 ms off.

Solid Blue: indicates that energy is being delivered to the medical instrument 100.

Solid Red: indicates a terminal failure and the medical instrument 100 can no longer be used. Energy is not being delivered to the medical instrument 100. All Solid Red light conditions have a 4 second timeout; after which the LED goes OFF. Power cannot be activated when the LED is Solid Red—can only activate power when LED is Green or Flashing Green.

Flashing Red: indicates a fault that may be recoverable and to wait for the light to change to Green or Red before operation can be resumed. Energy is not being delivered to the medical instrument 100 when the LED is Flashing Red. The rate of flashing is 300 ms on, 300 ms off, 300 ms on, 300 ms off. Power cannot be activated when the LED is Flashing Red—can only activate power when the LED Is Green or Flashing Green.

OFF: If before the plastic clip 600 has been removed, indicates that device has not yet been powered ON by removing the clip 600. If any time after the clip 600 has been removed, indicates that device is permanently powered OFF, and can be disposed of.

In one embodiment, the medical instrument 100 comprises an audio feedback element 410. The state of the medical instrument 100 can be determined by the state of the audio feedback element 410 as follows:

Power ON Tone: indicates that the medical instrument 100 has been powered ON. This occurs when the plastic clip 600 is removed. The audio feedback element 410 emits an audible 2.55 kHz 800 ms beep.

Activation Tone: indicates that energy is being delivered. This occurs when the hand activation button 114 is pressed by the user. The audio feedback element 410 emits an audible 2.55 kHz 150 ms beep, 200 ms pause, 2.55 kHz 150 ms beep, 200 ms pause, an so on. The beeping pattern continues as long as power is being activated and upper impedance limit has not been reached.

Activation Tone2: indicates that the upper impedance threshold has been reached. This occurs when the hand activation button 114 is pressed by user, and the upper impedance limit has been reached. The audio feedback element 410 emits an audible 2.8 kHz 150 ms beep, 200 ms pause, 2.8 kHz 150 ms beep, 200 ms pause, and so on. The Tone2 beeping pattern latches. After it has been reached, it continues as long as power is being activated or until Cycle Complete.

Cycle Complete Tone: indicates that the activation cycle is complete. The audio feedback element 410 emits an audible 2.8 kHz 800 ms beep.

Alert Tone: indicates an alert. The LED visual feedback element 118*a*, 118*b* provides further information. The audio feedback element 410 emits an audible 2.9 kHz 250 ms beep, 50 ms pause, 2.55 kHz 350 ms beep, 200 ms pause, 2.9 kHz 250 ms beep, 50 ms pause 2.55 kHz 350 ms beep, 200 ms pause, 2.9 kHz 250 ms beep, 50 ms pause, 2.55 kHz 350 ms beep. The two-tone beep repeats three times, then does not repeat after that). Power to the medical instrument 100 cannot be activated until "alert" sound has completed.

Timeout: indicates that activation cycle has timed out. Reactivate to continue. The audio feedback element 410 emits an audible 2.8 kHz 50 ms beep, 50 ms pause, 2.8 kHz 50 ms beep.

Solid Tone: indicates that the user disable button is being pressed. The audio feedback element 410 emits an audible continuous 2.55 kHz tone while being held, up to 4 seconds.

TABLE 3 below summarizes one embodiment of a user interface indicating the status (e.g., event/scenario) of the medical instrument 100 and the corresponding visual and audible feedback provided by the user interface.

TABLE 3

| Device Status | LED Feedback | Audible Feedback | Notes |
| --- | --- | --- | --- |
| Power is OFF | No light | None | |
| Turn power ON by removing the initialization Clip. | Solid Green Illuminates immediately when initialization Clip is removed. Indicates device is ready to be used, everything functioning normally. | One long beep immediately when initialization Clip is removed indicates power in ON. | |
| Power is ON but not being activated, device ready, above the "low transections remaining" threshold. | Solid Green Device ready to be used, everything functioning normally. | None | |
| Power ON, device ready, power not being activated, below the "low transections | Flashing Green Indicates that device is ready to be used, but a low number of transections remain; a minimum of five transections are left when | Two tone beeps: Indicates an alert: look at LED indicators for further information. | |

TABLE 3-continued

| Device Status | LED Feedback | Audible Feedback | Notes |
|---|---|---|---|
| remaining" threshold. | flashing first begins. | | |
| Power ON, device ready, power not being activated, "No transactions remaining" | Solid Red Indicates a terminal failure, device can no longer be used. Energy is not being delivered. | Two tone beeps: Indicates an alert: look at LED indicators for further information. | |
| Activating power | Solid Blue Energy is being delivered. | Continuous beeping during power activation. Indicates energy is being delivered. | Feedback for activation power is not affected by the 'low transactions remaining' threshold-behaves the same whether above or below threshold |
| Activation cycle timeout occurs after 25 sec of power activation without reaching Cycle Complete. | Solid Blue until two short beep sound completes, then changes to Solid Green. Indicates device is ready to be used, everything functioning normally. | Two short beeps. Indicates that the activation cycle has timed out. Reactivate to continue. | Upon detection of timeout, activation beeping will be immediately interrupted. After the interruption of activation beeping there will be a 100 ms pause. After the 100 ms pause, there will be the "Timeout" audio feedback. |
| Cycle Complete | Solid Blue until Cycle Complete sound finishes, then changes to Solid Green. | One long beep. Indicates that activation cycle is complete. | Cycle complete sound should occur after the first (200 ms) activation beeping pause following system detection of cycle complete. |
| Short Detected | Flashing Red, while in short circuit mode. LED returns to Solid Green when short circuit mode is cleared, or goes to Solid Red if terminal failure. Flashing Red indicates a fault that may be recoverable: wait for LED to change to Green or Red. Energy is not being detected when LED is Flashing Red. | Two tone beeps. Indicates an alert: look at LED indicators for further information. | There will be a "five strikes and out" approach to this condition: if a short is detected on five consecutive activations, the fifth detection will result in a terminal system failure. Upon detection of short, the activation beeping will be immediately interrupted. After the interruption of activation beeping there will be a 100 ms pause. After the 100 ms pause, there will be the "Alert" audio feedback. |
| Over-temperature condition | Flashing Red, while in over-temperature condition. LED returns to Solid Green when temperature drops below threshold. Flashing Red indicates a fault that may be recoverable: wait for LED to change to Green or Red. Energy is not being delivered when LED is Flashing Red. | Two tone beeps. Indicates an alert: look at LED indicator for further information. | Upon detection of a temporary over-temperature condition during activation, activation/beeping will not be interrupted. After the activation/beeping has been completed, there will be a 100 ms pause. After the 100 ms pause, there will be the 'Alert' audio feedback. |

TABLE 3-continued

| Device Status | LED Feedback | Audible Feedback | Notes |
|---|---|---|---|
| Terminal System failure | Solid Red LED red light stays on for four seconds and then goes off. Indicates a terminal failure, device can no longer be used. Energy is not being delivered when LED is Solid Red. | Two tone beeps. Indicates an alert: look at LED indicator for further information. | Upon detection of terminal system failure, any activation beeping (if applicable) will be immediately interrupted. After the interruption of any activation beeping there will be a 100 ms pause. After the 100 ms pause, there will be the 'Alert' audio feedback. All Solid Red light conditions have a 4 second timeout, after which the LED goes OFF |
| User initiates device disabling before disposal. Note: User can disable the device by pressing and holding User Disable Button on bottom of handle for four continuous seconds. | While User Disable Button is pressed and held continuously up to four seconds, LED is Flashing Red. After four continuous seconds of User Disable Button being held, LED goes to Solid Red. NOTE: LED red light stays on four seconds and then goes off. Indicates a terminal failure, and device can no longer be used. Energy is not being delivered. If User Disable Button is released at any time before four continuous seconds have passed, LED will return to Solid Green or Flashing Green as appropriate. | Solid continuous tone while pressing and holding User Disable Button continuously up to four seconds. After four continuous seconds of pressing User Disable Button, sound changes to two tone beeps. Indicates an alert: look at LED indicators for further information. | |

TABLE 4 below summarizes an additional or alternative embodiment of the status (e.g., event/scenario) of the medical instrument 100 and the corresponding visual and audible feedback provided by the user interface.

TABLE 4

| Device Status | LED Feedback | Audible Feedback | Notes |
|---|---|---|---|
| Power is OFF | No light | None | |
| Incomplete Cycle: user releases activation button prior to cycle complete and before the 15 second activation timeout. | Solid Blue, until activation button is released, then Solid Green | None | |
| Power ON, ready, power not being activated, below the Low Transections Remaining threshold. | Flashing Green | Alert Tone | After the appearance of the Green Flashing LED, there will be 5 transections remaining. Ad If an activation ends with a detection of an activation timeout, short detection, or over-temperature detection-and-the system has also crossed the low-uses remaining threshold after the same activation-then-the 'Alert' |

TABLE 4-continued

| Device Status | LED Feedback | Audible Feedback | Notes |
|---|---|---|---|
| | | | would sound once (as opposed to twice, or multiple times). In terms of alert hierarchy in this scenario in regard to the LED behavior, a short detection or over temperature takes precedence over the low-uses remaining indicator Once either the short or over-temperature condition is cleared by the system, the LED would then go to Flashing Green to indicate the device is ready to be used, but there are a low number of transactions remaining. |
| power ON, ready, power not being activated, No Transections Remaining. | Solid Red | Alert Tone | All Solid Red light conditions have a 4 second timeout, after which the LED goes OFF. |
| User Disables Device before disposal | Flashing Red while pressing & holding user disable button 120 continuously up to 4 seconds. After four continuous seconds of pressing user disable button, the LED goes to Solid Red, then the LED goes OFF after 4 seconds timeout. If user releases user disable button at any time before 4 continuous seconds, the LED will return to Solid Green | Solid Tone Alert Tone | User can disable the device by pressing & holding the user disable button on the bottom of the handle for 4 continuous seconds. The "Solid Tone" audio feedback is a Solid continuous tone that occurs as long as user presses & holds user disable button, up to 4 seconds. If user releases user disable button at any time before 4 continuous seconds, sound goes off. At the end of 4 seconds of continuous pressing, the "Solid Tone" slops, followed by a 100 ms pause, followed by the "Alert" audio feedback. The "Alert" audio feedback is accompanied by the LED changing to Solid Red, then LED goes OFF after 4 second timeout. |
| Activating Power - Tone 2 | Solid Blue | Activation Tone2 | Tone2 indicates that the upper impedance limit has been reached |

TABLE 4-continued

| Device Status | LED Feedback | Audible Feedback | Notes |
| --- | --- | --- | --- |
| | | | during activation, and that the knife is ready to be fully advanced. |

Figure 48A:
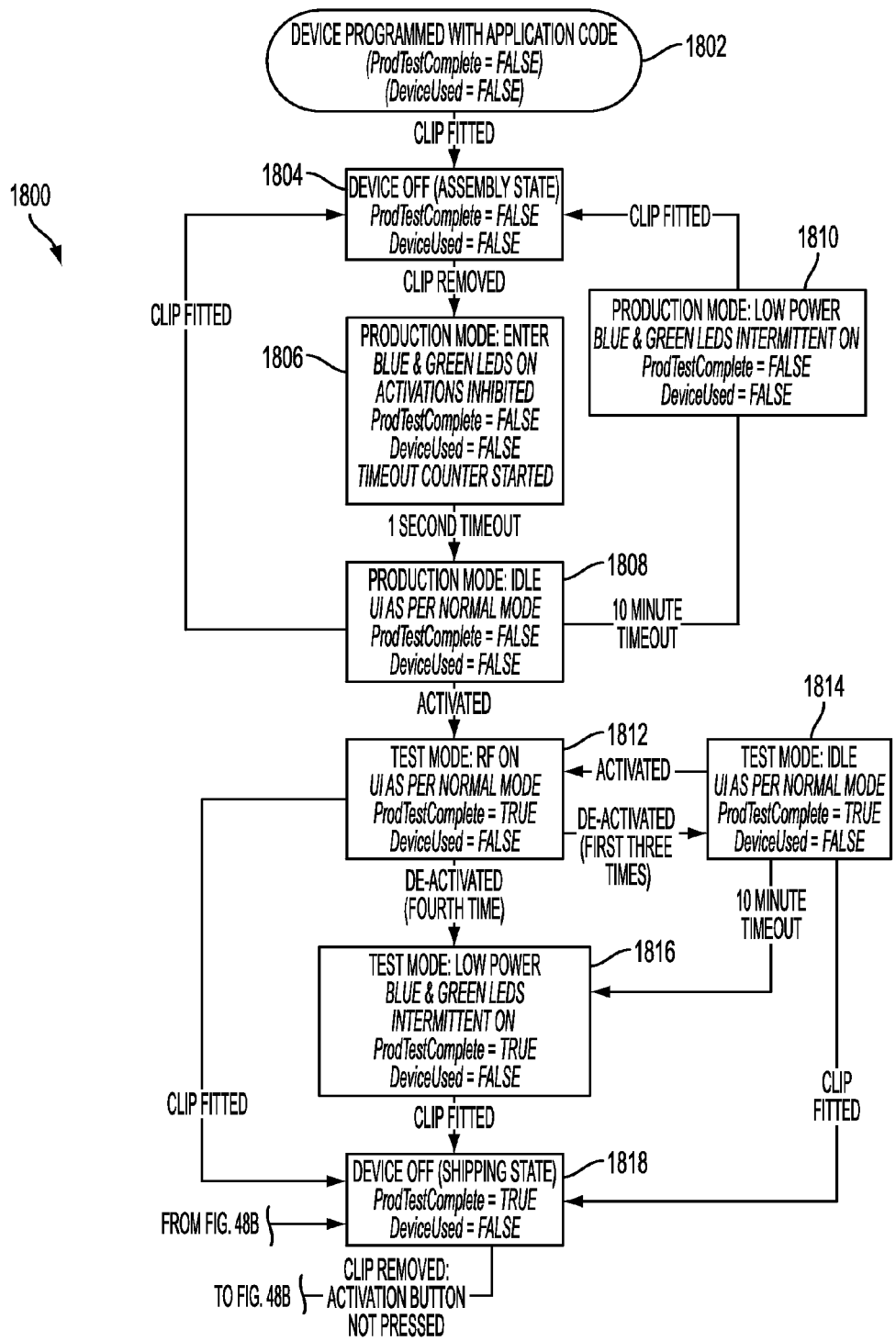
FIGS. 48A and 48B represent a flow diagram of a process for initializing a medical instrument fitted with an initialization clip, according to one embodiment.
Figure 48B:
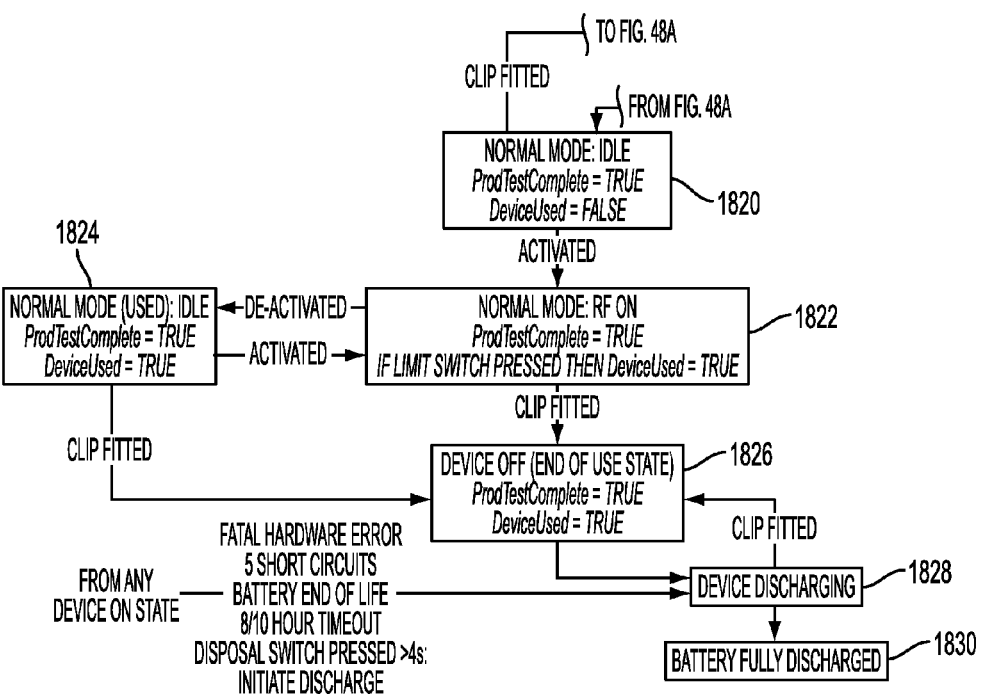

FIGS. 48A and 48B is a flow diagram of a process 1800 for initializing the medical instrument 100 fitted with the initialization clip 600, 650, according to one embodiment. As shown in the process 1800, at 1802 the medical instrument 100 is programmed with an application code. The application code is a set of computer instructions stored in the nonvolatile memory 402 that may be executed by the main processor 902, the safety processor 904, the controller 906, or any combination thereof. The Production Test Complete flag is set to FALSE and the Device Used flag also is set to FALSE.

The instrument 100 is then fitted with the clip 600, 650 and is turned OFF at 1804 and the instrument 100 enters what is referred to as the "assembly state." The Production Test Complete flag remains set to FALSE and the Device Used flag also remains set to FALSE.

At 1806 the instrument 100 is placed in the production mode after the clip 600, 650 is removed. In the production mode, the BLUE and GREEN LEDs 118a, b are turned ON and activation is inhibited. The Production Test Complete flag remains set to FALSE and the Device Used flag also remains set to FALSE. A timeout counter is started.

After a 1 second timeout, at 1808 the instrument 100 is still in the production mode, but remains idle. The user interface operates as per normal mode. From the production mode 1808 the process can continue to 1804 or to 1810. If the clip 600, 650 is fitted on the instrument 100 prior to a ten minute timeout, the process 1800 returns to 1804 were the instrument 100 is turned OFF and is placed in the assembly state. After a ten minute timeout period, the process 1800 continues at 1810. The instrument 100 is still in the production mode, but in a low power consumption state. The BLUE and GREEN LEDs 118a, b are intermittently ON (0.1 s ON and 1.9 s OFF). The clip 600, 650 is fitted back on the instrument 100, which turns the instrument 100 OFF, and the process 1800 returns to 1804. If at 1808 the instrument 100 is activated before the clip 600 is restored or before the ten-minute timeout period, the process continues to test mode at 1812. The Production Test Complete flag remains set to FALSE and the Device Used flag also remains set to FALSE. In test mode activations may be limited to four and timeout may be set to ten minutes. Furthermore, upon entry to test mode, the GREEN and BLUE LEDs 118a, b are illuminated for 1 s. Subsequently, the LEDs 118a, b and the audio feedback element 410 follow the user interface specification.

At 1812, the instrument 100 is placed in test mode where the RF amplifier subsection 800 is turned ON. The user interface operates per normal mode. The Production Test Complete flag is set to TRUE and the Device Used flag remains set to FALSE.

From 1812, the clip 600, 650 may be fitted to the instrument 100 turning the instrument 100 OFF and the process 1800 may continue at 1818 where the instrument 100 is placed in a shipping state. The Production Test Complete flag remains set to TRUE and the Device Used flag remains set to FALSE.

From 1812, the process may continue at 1814 after the instrument 100 is de-activated for the first three times. At 1814 the instrument 100 is placed in idle mode. The UI operates as pre normal. The Production Test Complete flag remains set to TRUE and the Device Used flag remains set to FALSE. The instrument 100 is activated once more and the process 1800 continues to 1812. The instrument 100 is de-activated a fourth time, the clip 600, 650 is fitted to the instrument 100, and the process 1800 continues to 1816 where the instrument 100 is placed in low power mode and the BLUE and GREEN LEDs 118a, b are flashed intermittently ON (0.1 s ON and 1.9 s OFF). The Production Test Complete flag remains set to TRUE and the Device Used flag remains set to FALSE. The clip 600, 650 is fitted back on the instrument 100, which is turned OFF and placed in the shipping state. The instrument 100 enters low power mode after the instrument 100 has been activated twice by pressing the activation button 114 or following expiration of the 10 minute timeout period.

From 1814, rather than activating the instrument 100, a 10 minute timeout period may be allowed to lapse or the clip 600, 650 may be fitted back on the instrument 100. If the 10 minute timeout period is allowed to lapse, the process 1800 continues 1816. If the clip 600, 650 is fitted back on the instrument, the process 1800 continues at 1818.

From 1818, the instrument 100 may be shipped to the user. Before using the instrument 100, the user has to remove the clip 600, 650 from the instrument 100 and then must activate the instrument 100. After the clip 600, 650 is removed from the instrument 100 but before the activation button 114 is pressed, the process continues at 1820 where the instrument is placed in normal mode but is in idle. The Production Test Complete flag remains set to TRUE and the Device Used flag remains set to FALSE. If the clip 600, 650 is fitted back on the instrument 100, the process 1800 continues back to 1818. If the activation button 114 is activated, however, the process 1800 continues 1822 where the instrument is placed in normal mode and the RF section is turned ON. Now Production Test Complete flag remains set to TRUE and the Device Used flag is set to TRUE. The instrument 100 only gets marked for disposal (Device Used Flag is TRUE) if the instrument 100 has been activated and the limit switch is pressed during normal mode. If the instrument 100 is now de-activated, the process 1800 continues to 1824 where the instrument is placed in normal mode idle. From 1824, if the instrument is activated by pressing the activation button 114, the process 1800 continues at 1822. From either 1822 or 1824, if the clip 600, 650 is fitted back on the instrument 100, the process continues to 1826 where the instrument 100 is turned OFF and enters an end of use state. Both the Production Test Complete flag and the Device Used flag remain set to TRUE. The clip 600, 650 should be removed at the end of test as a final check to ensure the GREEN LED 118a, b comes on. If the RED LED 118a, b comes on instead, the instrument 100 has entered self destruct mode.

From 1826, if the clip 600, 650 is removed, the instrument 100 initiates discharging the battery 300 and the process 1800 continues to 1828 where the battery 300 continues discharging until the battery 300 is fully discharged at 1830. From 1828, the clip 600, 650 may be fitted back on the instrument 100, in which case, the process 1800 continues to 1826. If any fatal hardware errors occur from any instrument state such as, five short circuits, battery end of life, 8/10 hour timeout, disposal switch 120 is pressed for more than 4 seconds, or the battery 300 initiates discharge, the process 1800 continues to 1828.

FIG. 49-57 illustrates the ornamental design for a surgical instrument handle assembly as shown and described, according to one embodment.

Figure 49:
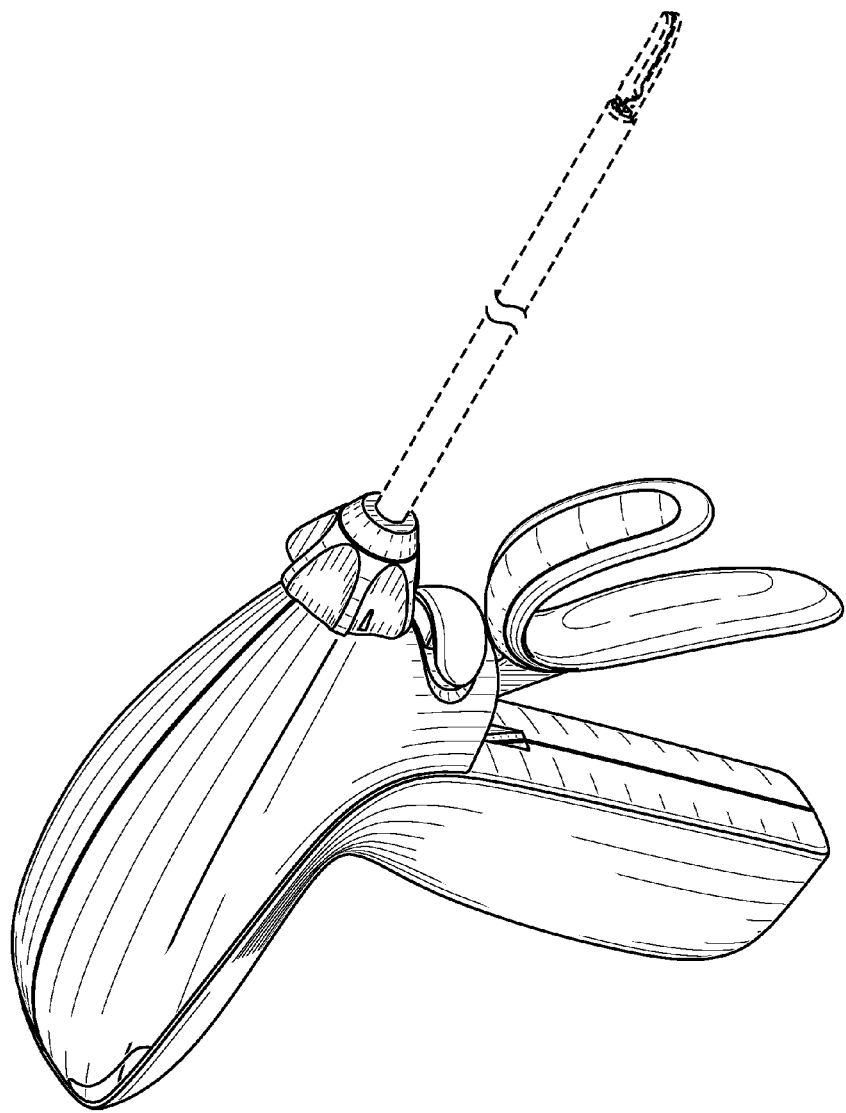

FIG. 49 is a left perspective view of a handle assembly for a surgical instrument.

Figure 50:
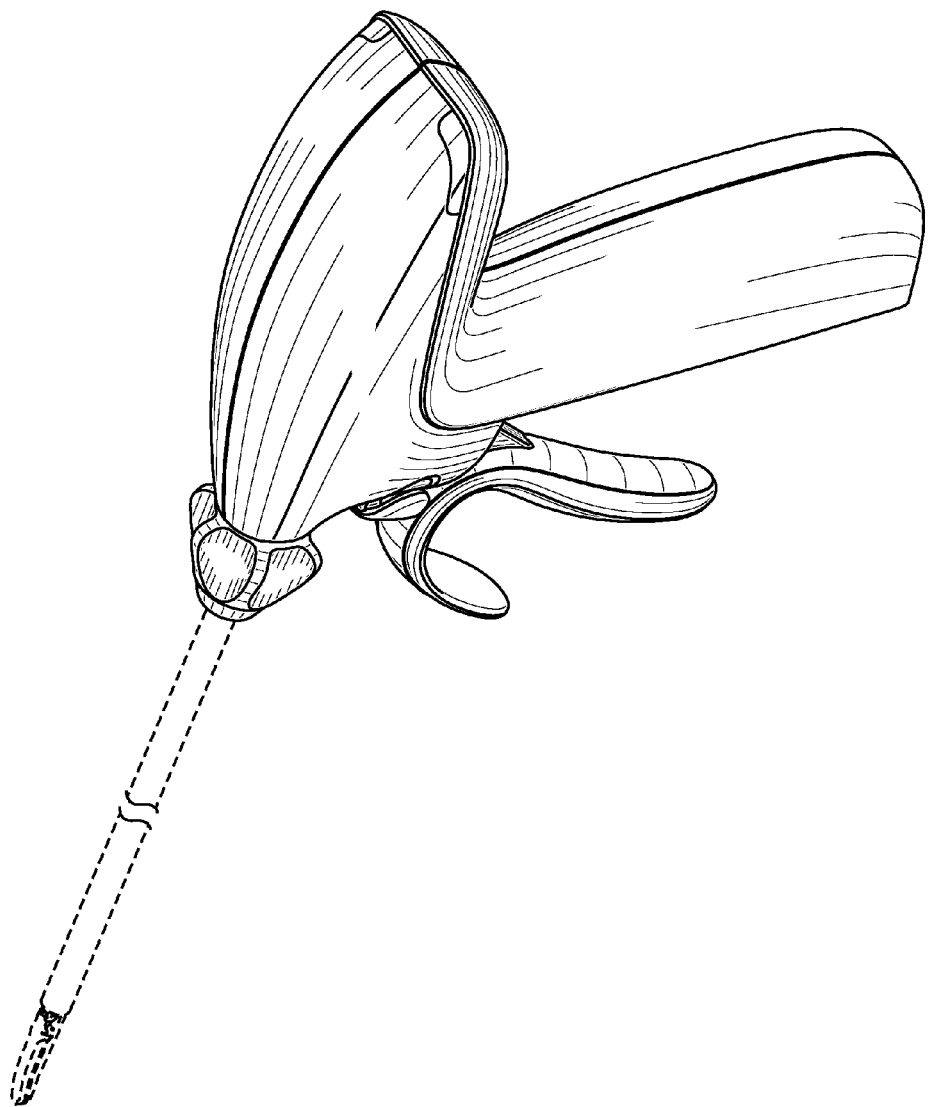

FIG. 50 is a right perspective view thereof.

Figure 51:
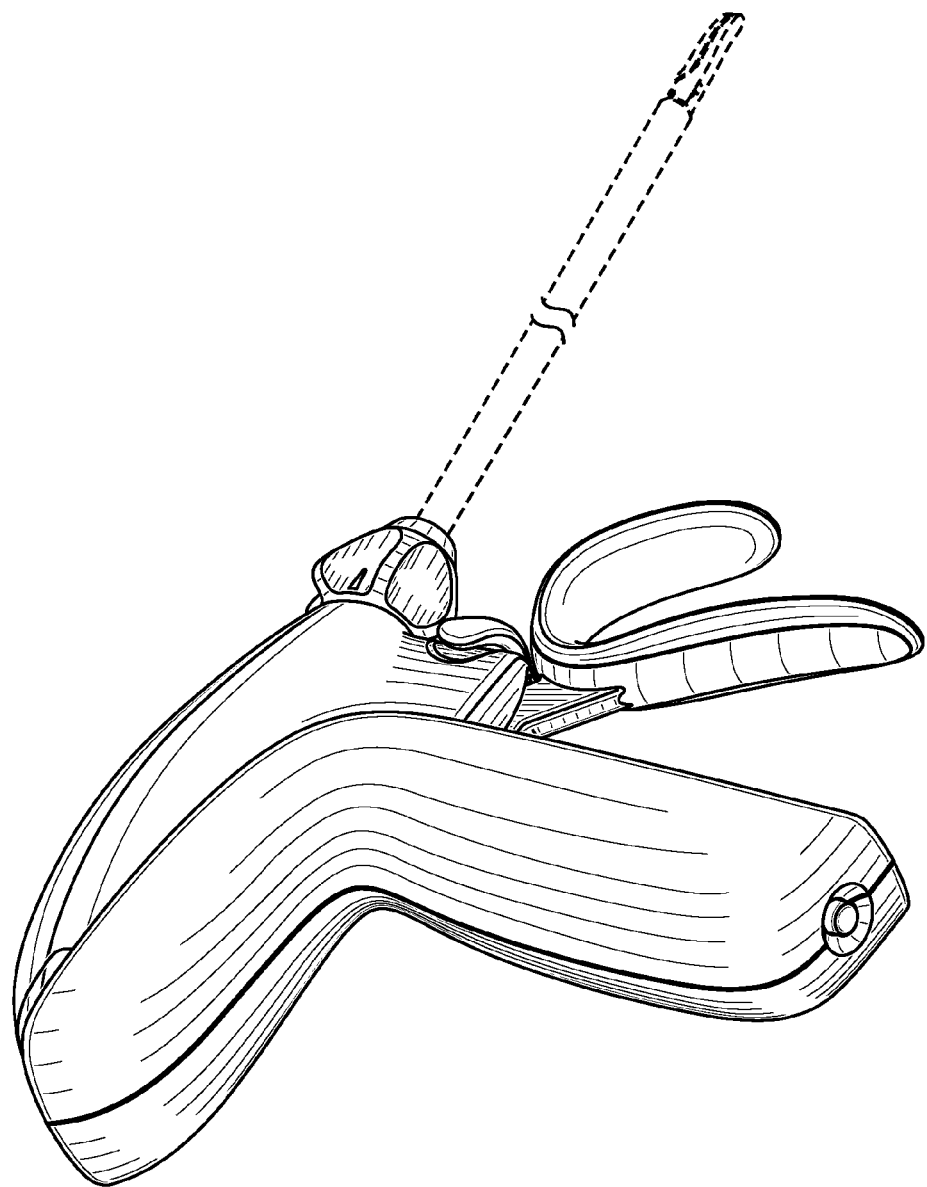

FIG. 51 is a left perspective view thereof.

FIG. 52 is a left view thereof.

FIG. 53 is a front view thereof.

Figure 54:
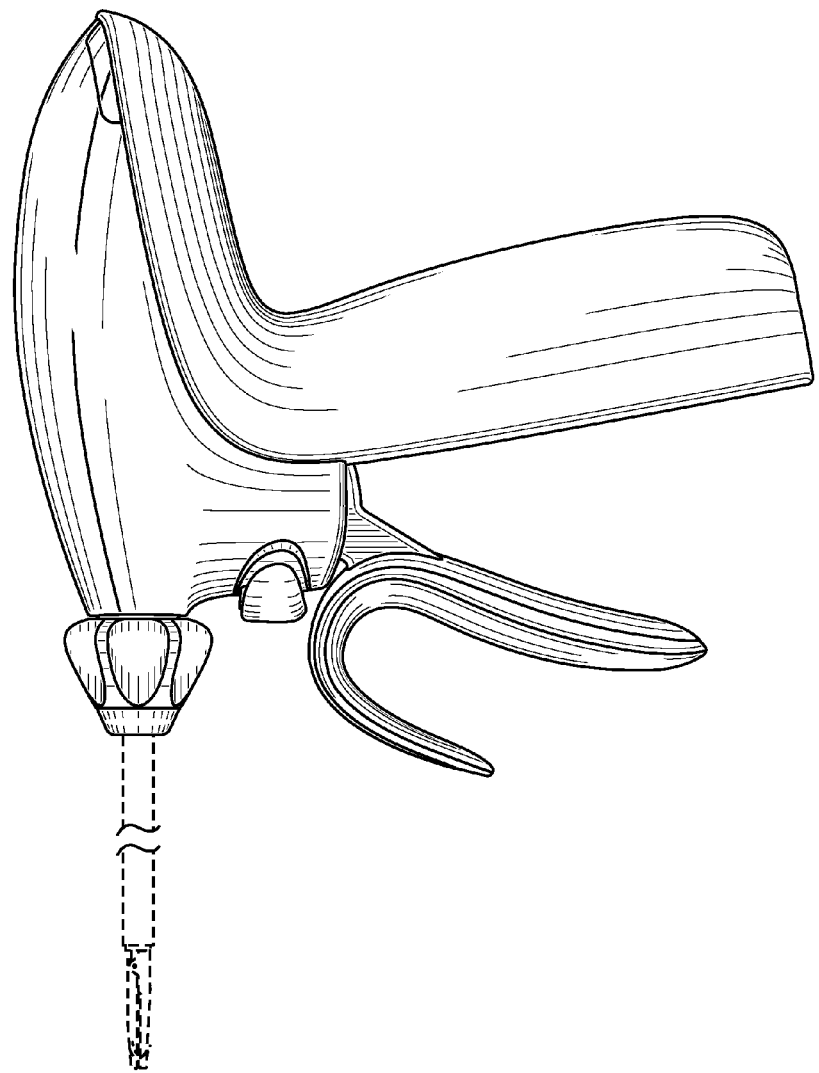

FIG. 54 is a right view thereof.

Figure 55:
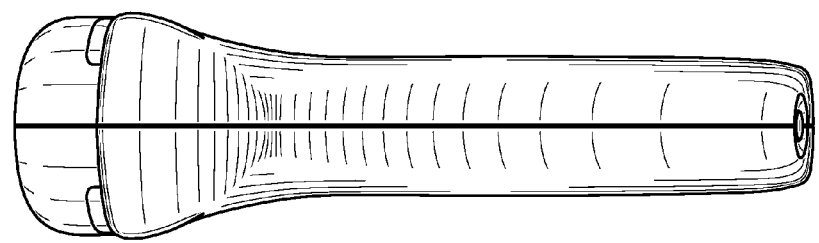

FIG. 55 is a rear view thereof.

Figure 56:
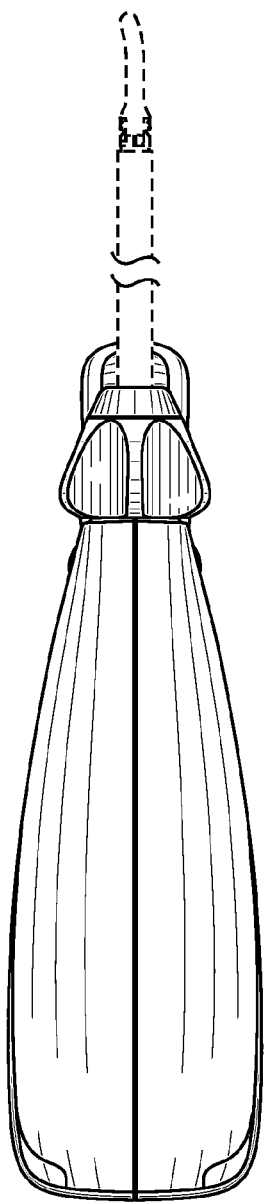

FIG. 56 is a top view thereof.

Figure 57:
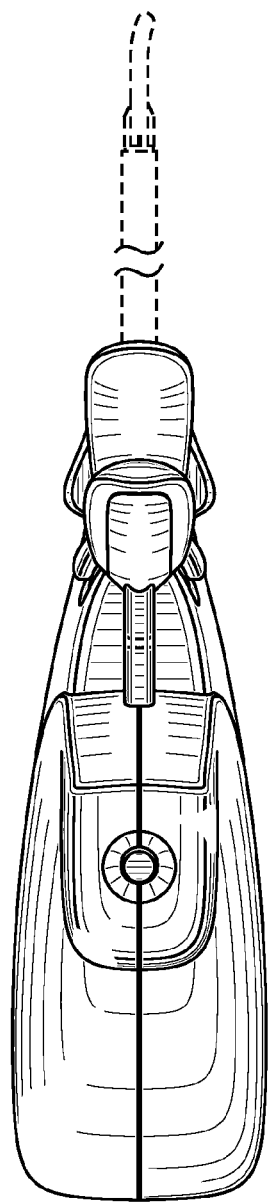

FIG. 57 is a bottom view thereof.

It is worthy to note that any reference to "one aspect" or "an aspect" means that a particular feature, structure, or characteristic described in connection with the aspect is included in at least one aspect. Thus, appearances of the phrases "in one aspect" or "in an aspect" in various places throughout the specification are not necessarily all referring to the same aspect. Furthermore, the particular features, structures or characteristics may be combined in any suitable manner in one or more aspects.

Some aspects may be described using the expression "coupled" and "connected" along with their derivatives. It should be understood that these terms are not intended as synonyms for each other. For example, some aspects may be described using the term "connected" to indicate that two or more elements are in direct physical or electrical contact with each other. In another example, some aspects may be described using the term "coupled" to indicate that two or more elements are in direct physical or electrical contact. The term "coupled," however, also may mean that two or more elements are not in direct contact with each other, but yet still co-operate or interact with each other.

While certain features of the aspects have been illustrated as described herein, many modifications, substitutions, changes and equivalents will now occur to those skilled in the art. It is therefore to be understood that the appended claims are intended to cover all such modifications and changes as fall within the true scope of the disclosed embodiments.

Various aspects of the subject matter described herein are set out in the following numbered clauses:

1. A medical instrument comprising: a handle for gripping by a user, an end effector coupled to the handle and having at least one electrical contact; a radio frequency (RF) generation circuit coupled to the handle and operable to generate an RF drive signal and to provide the RF drive signal to the at least one electrical contact; wherein the RF generation circuit comprises a parallel resonant circuit.

2. The medical instrument according to clause 1, wherein the RF generation circuit comprises switching circuitry that generates a cyclically varying signal, such as a square wave signal, from a direct current (DC) supply and wherein the resonant circuit is configured to receive the cyclically varying signal and wherein the cyclically varying signal is duty cycle modulated.

3. The medical instrument according to clause 1, comprising a battery compartment for holding one or more batteries for providing power to the RF generation circuit for generating said RF drive signal.

4. The medical instrument according to clause 3, wherein the battery compartment is configured to hold a module comprising the one or more batteries and the RF generation circuit.

5. A device according to clause 1, further comprising: battery terminals for connecting to one or more batteries; wherein the RF generation circuit is coupled to the battery terminals; wherein the frequency generation circuit comprises: switching circuitry for generating a cyclically varying signal from a potential difference across the battery terminals; and the resonant circuit, being a resonant drive circuit coupled to the switching circuitry and operable to filter the cyclically varying signal generated by the switching circuitry; and wherein the RF drive signal is controlled by an output from said resonant drive circuit.

6. The medical instrument according to clause 1, comprising a control circuit configured to vary the frequency of the RF drive signal.

7. The medical instrument according to clause 1, comprising a control circuit configured to vary the amplitude of the RF drive signal.

8. The medical instrument according to clause 1, comprising a control circuit configured to vary the duty cycle of the RF drive signal.

9. The medical instrument according to clause 8, wherein the control circuit is operable to receive a measurement of the RF drive signal and is operable to vary the frequency of the of the RF drive signal to control the power, voltage and/or current delivered to the at least one electrical contact of the end effector.

10. The medical instrument according to clause 9, wherein the measurement is obtained from a sampling circuit that samples a sensed voltage or current signal at a sampling frequency that varies in synchronism with the frequency and phase of the RF drive signal.

11. The medical instrument according to clause 10, wherein the frequency at which the sampling circuit is operable to sample the sensed signal is an integer fraction of the frequency of the RF drive signal.

12. The medical instrument according to clause 8, wherein the control circuit is configured to vary the frequency of the RF drive signal around the resonant frequency of the resonant circuit.

13. The medical instrument according to clause 12, wherein the resonant characteristic of the resonant circuit varies with a load connected to the at least one electrical contact and wherein the control circuit is configured to vary the RF drive frequency to track changes in the resonant characteristic of the resonant circuit.

14. The medical instrument according to clause 1, wherein the handle comprises: a control lever to operate the end effector; and an activation button to operate the RF generation circuit and deliver RF energy to the end effector.

15. The medical instrument according to clause 14, comprising a rotation knob coupled to end effector to rotate the end effector about an angle greater than 360°.

16. The medical instrument according to clause 14, comprising at least one visual feedback element to indicate a state of the medical instrument.

17. The medical instrument according to clause 14, comprising an audio feedback element to indicate a state of the medical instrument.

18. The medical instrument according to clause 17, comprising an aperture formed in the handle to provide a path for audio waves to escape an interior portion of the handle.

19. The medical device according to clause 14, comprising a knife lockout mechanism.

20. The medical device according to clause 14, comprising a clip coupled to the control lever.

21. The medical instrument according to clause 20, comprising a magnet located within the clip.

22. The medical instrument according to clause 21, comprising a magnetically operated element coupled to an electronics system of the medical instrument and a battery of the medical instrument, wherein when the magnet is located within the clip and the clip is coupled to the control lever, the magnetically operated element disconnects the battery from the system electronics.

The invention claimed is:

1. A medical instrument comprising:
   a housing and a handle for gripping by a user, an end effector coupled to the handle and having at least one electrical contact;
   a battery;
   a radio frequency (RF) generation circuit coupled to and operated by the battery and operable to generate an RF drive signal having a predetermined frequency and phase and to provide the RF drive signal to the at least one electrical contact, wherein the RF generation circuit is supported by the housing; and
   a sampling circuit;
   wherein the RF generation circuit comprises a resonant circuit comprising at least one inductive element constructed of litz wire;
   wherein the sampling circuit is configured to sample a sensed voltage or current signal at a sampling frequency that varies in synchronism with the frequency and phase of the RF drive signal.

2. The medical instrument of claim 1, wherein the resonant circuit comprises a transformer and an inductor, wherein the transformer comprises a primary coil and a secondary coil constructed of litz wire.

3. The medical instrument of claim 2, wherein the primary coil is constructed of 300 strand 46 gauge litz wire wound at 24 turns per foot (TPF).

4. The medical instrument of claim 3, wherein the primary coil has an inductance of about 270 nH, an AC resistance of less than 46 mΩ, and a DC resistance less than or equal to 5 mΩ.

5. The medical instrument of claim 2, wherein the secondary coil is constructed of 105 strand 44 gauge litz wire wound at 24 TPF.

6. The medical instrument of claim 5, wherein the secondary coil has an inductance of about 22 μH at 430 kHz, an AC resistance of less than 2.5Ω, and a DC resistance less than or equal to 80 mΩ.

7. The medical instrument of claim 2, wherein the inductor comprises a coil constructed of litz wire.

8. The medical instrument of claim 7, wherein the inductor coil is constructed of 300 strand 46 gauge litz wire wound at 24 turns per foot (TPF).

9. The medical instrument of claim 8, wherein the inductor coil has an inductance of about 345 nH at 430 kHz, an AC resistance of less than 50 mΩ, and a DC resistance less than or equal to 7 mΩ.

10. The medical instrument of claim 2, wherein the transformer comprises a ferrite core.

11. The medical instrument of claim 2, wherein the inductor comprises a ferrite core.

12. The medical instrument of claim 2, wherein the inductor and the primary coil of the transformer form a resonant circuit.

13. A medical instrument comprising:
    a battery operated radio frequency (RF) generation circuit operable to generate an RF drive signal of a predetermined frequency and phase and to provide the RF drive signal to at least one electrical contact, wherein the RF generation circuit comprises a resonant circuit comprising at least one inductive element constructed of litz wire; and
    a sampling circuit configured to sample a sensed voltage or current signal at a sampling frequency that varies in synchronism with the frequency and phase of the RF drive signal.

14. The medical instrument according to claim 13, wherein the RF generation circuit comprises switching circuitry that generates a cyclically varying signal from a direct current (DC) supply and wherein the resonant circuit is configured to receive the cyclically varying signal and wherein the cyclically varying signal is duty cycle modulated.

15. The medical instrument according to claim 13, comprising a battery compartment for holding one or more batteries for providing power to the RF generation circuit for generating said RF drive signal.

16. The medical instrument according to claim 13, further comprising:
    battery terminals for connecting to one or more batteries;
    wherein the RF generation circuit is coupled to the battery terminals;
    wherein the frequency generation circuit comprises:
    switching circuitry for generating a cyclically varying signal from a potential difference across the battery terminals; and
    the resonant circuit, being a resonant drive circuit coupled to the switching circuitry and operable to filter the cyclically varying signal generated by the switching circuitry; and
    wherein the RF drive signal is controlled by an output from said resonant drive circuit.

17. The medical instrument according to 13, comprising a control circuit configured to vary the frequency of the RF drive signal.

18. The medical instrument according to claim 13, comprising a control circuit configured to vary the amplitude of the RF drive signal.

19. The medical instrument of claim 13, wherein the resonant circuit comprises a transformer and an inductor, wherein the transformer comprises a primary coil and a secondary coil constructed of litz wire.

20. A medical instrument comprising:
    a battery operated radio frequency (RF) generation circuit operable to generate an RF drive signal and to provide the RF drive signal to the at least one electrical contact; and
    a control circuit configured to vary the duty cycle of the RF drive signal; and
    a sampling circuit coupled to the control circuit;
    wherein the RF generation circuit comprises a resonant circuit comprising at least one inductive element constructed of litz wire;
    wherein the control circuit is operable to receive a measurement of the RF drive signal and from the sampling circuit and is operable to vary the frequency of the RF drive signal to control the power, voltage and/or current delivered to at least one electrical contact of the end effector; and wherein the sampling circuit is configured to sample a sensed voltage or current signal at a sampling frequency that varies in synchronism with the frequency and phase of the RF drive signal.

21. The medical instrument according to claim 20, wherein the frequency at which the sampling circuit is operable to sample the sensed signal is an integer fraction of the frequency of the RF drive signal.

22. The medical instrument according to claim 20, wherein the control circuit is configured to vary the frequency of the RF drive signal around the resonant frequency of the resonant circuit.

23. The medical instrument according to claim 22, wherein the resonant characteristic of the resonant circuit varies with a load connected to the at least one electrical contact and wherein the control circuit is configured to vary the RF drive frequency to track changes in the resonant characteristic of the resonant circuit.

* * * * *